United States Patent
Iriyama et al.

(10) Patent No.: US 11,555,188 B2
(45) Date of Patent: Jan. 17, 2023

(54) SINGLE-STRANDED OLIGONUCLEOTIDE

(71) Applicant: NISSAN CHEMICAL CORPORATION, Tokyo (JP)

(72) Inventors: Yusuke Iriyama, Funabashi (JP); Hiroyuki Nakajima, Shiraoka (JP); Tatsuro Kanaki, Shiraoka (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 0 days.

(21) Appl. No.: 16/633,532

(22) PCT Filed: Jul. 26, 2018

(86) PCT No.: PCT/JP2018/028075
§ 371 (c)(1),
(2) Date: Jan. 23, 2020

(87) PCT Pub. No.: WO2019/022196
PCT Pub. Date: Jan. 31, 2019

(65) Prior Publication Data
US 2020/0224196 A1 Jul. 16, 2020

(30) Foreign Application Priority Data
Jul. 26, 2017 (JP) .............................. JP2017-144575

(51) Int. Cl.
| C07H 21/04 | (2006.01) |
| C12N 15/113 | (2010.01) |
| C12N 15/10 | (2006.01) |
| A61K 31/712 | (2006.01) |

(52) U.S. Cl.
CPC .......... *C12N 15/113* (2013.01); *A61K 31/712* (2013.01); *C12N 15/1024* (2013.01)

(58) Field of Classification Search
CPC .................................................... C07H 21/04
See application file for complete search history.

(56) References Cited

U.S. PATENT DOCUMENTS

| 6,268,490 | B1 | 7/2001 | Imanishi et al. | |
| 9,816,089 | B2* | 11/2017 | Yokota | C12N 15/113 |
| 2006/0166908 | A1 | 7/2006 | Imanishi et al. | |
| 2007/0167387 | A1 | 7/2007 | Imanishi et al. | |
| 2010/0112686 | A1 | 5/2010 | Ge et al. | |
| 2012/0208991 | A1 | 8/2012 | Obika et al. | |
| 2014/0302603 | A1 | 10/2014 | Yokota et al. | |
| 2015/0247141 | A1 | 9/2015 | Uhlmann et al. | |
| 2017/0349896 | A1 | 12/2017 | Albaek et al. | |
| 2019/0119683 | A1 | 4/2019 | Iriyama et al. | |

FOREIGN PATENT DOCUMENTS

| EP | 1115859 A2 | 7/2001 |
| EP | 3584319 A1 | 12/2019 |
| JP | H08-154687 A | 6/1996 |
| JP | H09-110894 A | 4/1997 |
| JP | H11-137260 A | 5/1999 |
| JP | 2002-526072 A | 8/2002 |
| JP | 2012-505657 A | 3/2012 |
| JP | 2015-502134 A | 1/2015 |
| JP | 2015-529469 A | 10/2015 |
| JP | 2017-505623 A | 2/2017 |
| WO | WO 1998/039352 A1 | 9/1998 |
| WO | WO 2000/017346 A2 | 3/2000 |
| WO | WO 2005/021570 A1 | 3/2005 |
| WO | WO 2003/068795 A1 | 8/2006 |
| WO | WO 2011/052436 A1 | 5/2011 |
| WO | WO 2011/156202 A1 | 12/2011 |
| WO | WO 2013/089283 A1 | 6/2013 |
| WO | WO 2014/179620 A1 | 11/2014 |
| WO | WO 2014/192310 A1 | 12/2014 |
| WO | WO 2015/105083 A1 | 7/2015 |
| WO | WO 2017/131124 A1 | 8/2017 |
| WO | WO 2018/143475 A1 | 8/2018 |

OTHER PUBLICATIONS

Hamazaki et al., "Inhibition of Influenza Virus Replication in MDCK Cells by Circular Dumbbell RNA/DNA Chimeras with Closed Alkyl Loop Structures," *Helv. Chim. Acta,* 85(7): 2183-2194 (2002).
Nishina et al., "DNA/RNA heteroduplex oligonucleotide for highly efficient gene silencing," *Nat. Commun.,* 6: 7969 (2015).
Park et al., "Inhibition of HIV-1 Replication by a New Type of Circular Dumbbell RNA/DNA Chimeric Oligonucleotides," *Biochem. Biophys. Res. Commun.,* 270(3): 953-960 (2000).
Subramanian et al., "Enhancing antisense efficacy with multimers and multi-targeting oligonucleotides (MTOs) using cleavable linkers," *Nucleic Acids Res.,* 43(19): 9123-9132 (2015).
Japanese Patent Office, International Search Report in International Patent Application No. PCT/JP2018/028075 (dated Oct. 23, 2018).

* cited by examiner

*Primary Examiner* — Kimberly Chong
(74) *Attorney, Agent, or Firm* — Leydig, Voit & Mayer, Ltd.

(57) ABSTRACT

The invention provides a single-stranded oligonucleotide represented by the formula $[Xz-Lx]_m-X-Y-[Ly-Yz]_n$, wherein X is represented by Xa-Xb, Xa is coupled with Y, and Xb and Y hybridize. Xa is composed of 1 to 40 nucleotides and contains at least one modified-nucleotide. Xb is composed of 4 to 40 nucleotides and contains at least one modified-nucleotide. Y is composed of 4 to 40 nucleotides and contains at least one ribonucleotide. Xz and Yz are composed of 5 to 40 nucleotides and contain at least one modified-nucleotide. Nucleotide sequences X, Xz and Yz have an antisense sequence capable of hybridizing with a target RNA. Lx and Ly are composed of 0 to 20 nucleotides.

28 Claims, 4 Drawing Sheets
Specification includes a Sequence Listing.

| Lane No. | |
|---|---|
| 1 | ss-DNA size marker (15mer, 20mer, 30mer, 40mer, 60mer, 80mer) |
| 2 | Example No. 1 (before) |
| 3 | Example No. 1 (after) |
| 4 | ds-RNA size marker (17bp, 21bp, 25bp, 29bp) | even # SINGLE-STRANDED OLIGONUCLEOTIDE

CROSS-REFERENCE TO RELATED APPLICATIONS

This patent application is the U.S. national phase of International Patent Application No. PCT/JP2018/028075, filed on Jul. 26, 2018, which claims the benefit of Japanese Patent Application No. 2017-144575, filed on Jul. 26, 2017, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 8,176 bytes ASCII (Text) file named "747417SequenceListing.txt," created Jan. 21, 2020.

TECHNICAL FIELD

The present invention relates to a single-stranded oligonucleotide.

BACKGROUND ART

Antisense oligonucleotides (ASO) are single-stranded DNA, RNA and/or structural analogues thereof composed of about 8 to 30 bases that are complementary oligonucleotides to the mRNA or mRNA precursor of a target gene or ncRNA (non-coding RNA) such as ribosomal RNA, transfer RNA or miRNA. ASO suppress the function of mRNA, mRNA precursors or ncRNA by forming a double strand with mRNA, mRNA precursor or ncRNA targeted by the antisense oligonucleotide.

However, practical application of ASO is difficult since they are easily degraded by nucleases in the living body and their uptake efficiency into target cells is low. In order to overcome these two major problems, research has been conducted for many years on chemical modification of the active ingredient in the form of the oligonucleotide per se as well as on drug delivery systems (DDS) capable of delivering an oligonucleotide into a target cell.

Known examples of chemical modification of ASO per se include S-oligo (phosphorothioate), in which the phosphate moiety has been modified, and 2',4'-BNA (bridged nucleic acid)/LNA (locked nucleic acid), in which the sugar moiety has been modified (see Patent Documents 1 to 5).

Known examples of DDS include methods utilizing carriers such as cationic liposomes or polymeric micelles. In addition, Patent Document 6 describes an ASO in which a GalNAc (N-acetylgalactosamine) derivative, which is a sugar derivative having the ability to interact with asialoglycoprotein receptors, is bound via a linker, and that expression of a target gene in the liver is suppressed following administration of this ASO.

Patent Document 7 and Non-Patent Document 1 describe that, by bonding tocopherol (Toc) to a double-stranded oligonucleotide (HDO) containing an RNA oligonucleotide complementary to ASO, the HDO is delivered and concentrated in the liver more efficiently than ASO and expression of a target gene in the liver is suppressed in mice. Patent Document 8 describes an ASO in which a GalNAc derivative is bound to an HDO via a linker, and that expression is suppressed more efficiently than tocopherol (Toc) modification when the antisense oligonucleotide is administered subcutaneously.

Patent Document 9 describes that an oligonucleotide (HCDO), in which an ASO is bound to the end of an RNA strand of a double-stranded oligonucleotide unit consisting of DNA and RNA, suppresses a target RNA more efficiently than the ASO.

PRIOR ART DOCUMENTS

Non-Patent Documents

Non-Patent Document 1: Nature Communications, Vol. 6, Article No: 7969 (2015)

Patent Documents

Patent Document 1: International Publication No. WO 98/39352
Patent Document 2: International Publication No. WO 2005/021570
Patent Document 3: International Publication No. WO 2003/068795
Patent Document 4: International Publication No. WO 2011/052436
Patent Document 5: International Publication No. WO 2011/156202
Patent Document 6: International Publication No. WO 2014/179620
Patent Document 7: International Publication No. WO 2013/089283
Patent Document 8: International Publication No. WO 2015/105083
Patent Document 9: International Publication No. WO 2014/192310

DISCLOSURE OF THE INVENTION

Problems to be Solved by the Invention

There is a desire for novel nucleic acid pharmaceuticals capable of efficiently suppressing the expression of a target gene when indicated for use as pharmaceuticals in mammals, including humans, in the clinical setting. In addition, in the case of producing double-stranded oligonucleotides (such as the above-mentioned HDO or HCDO), a step is required for separately synthesizing the antisense strand and complementary RNA strand followed by hybridizing these strands. Moreover, when administering to animals or cells, it is necessary that the double-stranded oligonucleotide be inhibited from dissociating into single strands, and it can be presumed that there are cases in which considerable effort is required to set up the handling conditions.

An object of the present invention is to provide a novel oligonucleotide capable of suppressing expression of a target gene with high efficiency. In addition, an object of the present invention is to provide an oligonucleotide that can be more easily produced than double-stranded oligonucleotides.

Means for Solving the Problems

In order to accomplish the above-mentioned objects, the inventors of the present invention found that, a single-stranded oligonucleotide in which an oligonucleotide strand (X strand) containing an antisense sequence and an oligonucleotide strand (Y strand) containing RNA are coupled, where the single-stranded oligonucleotide has a structure in which the above-mentioned X strand comprises Xa strand which couples with the above-mentioned Y strand and Xb strand which does not couple therewith, and the above-mentioned Y strand and the above-mentioned Xb strand are partially intramolecular hybridized shows an antisense effect equal to or more than that of a double-stranded oligonucleotide. Further, since the single-stranded oligonucleotide consists of a single strand, there is no hybridizing step for forming a double strand, so that it can be produced efficiently. The present invention includes the aspects indicated below.

1. A single-stranded oligonucleotide represented by the formula (I):

[Formula 1]

$$[Xz\text{-}Lx]_m\text{-}X\text{-}Y\text{-}[Ly\text{-}Yz]_n \quad (I)$$

{wherein,
Y represents a group derived from an oligonucleotide Y composed of 4 to 40 nucleotides containing at least one ribonucleotide that are independently selected from the group consisting of deoxyribonucleotides, ribonucleotides and sugar-modified nucleotides, X represents a group derived from an oligonucleotide X composed of 5 to 80 nucleotides represented by the formula:

Xb-Xa [Formula 2]

(wherein, Xb represents a group derived from an oligonucleotide Xb composed of 4 to 40 nucleotides containing at least one sugar-modified nucleotides that are independently selected from the group consisting of deoxyribonucleotides, ribonucleotides and sugar-modified nucleotides, Xa represents a group derived from an oligonucleotide Xa composed of 1 to 40 nucleotides containing at least one sugar-modified nucleotides that are independently selected from the group consisting of deoxyribonucleotides, ribonucleotides and sugar-modified nucleotides, and Xa is bonded with the oligonucleotide Y and the oligonucleotide Xb at both ends respectively), Xz represents a group derived from an oligonucleotide Xz composed of 5 to 40 nucleotides containing at least one sugar-modified nucleotides that are independently selected from the group consisting of deoxyribonucleotides, ribonucleotides and sugar-modified nucleotides, Yz represents a group derived from an oligonucleotide Yz composed of 5 to 40 nucleotides containing at least one sugar-modified nucleotides that are independently selected from the group consisting of deoxyribonucleotides, ribonucleotides and sugar-modified nucleotides, Lx represents a group derived from an oligonucleotide Lx composed of 0 to 20 nucleotides that are independently selected from the group consisting of deoxyribonucleotides, ribonucleotides and sugar-modified nucleotides, and is bonded with the Xb, Ly represents a group derived from an oligonucleotide Ly composed of 0 to 20 nucleotides that are independently selected from the group consisting of deoxyribonucleotides, ribonucleotides and sugar-modified nucleotides, m represents 0 or 1,
when m represents 0, n represents 0 or 1,
when m represents 1, n represents 0,
the oligonucleotide X has a nucleotide sequence X, the oligonucleotide Xa has a nucleotide sequence Xa, the oligonucleotide Xb has a nucleotide sequence Xb, the oligonucleotide Y has a nucleotide sequence Y, the oligonucleotide Xz has a nucleotide sequence Xz, the oligonucleotide Yz has a nucleotide sequence Yz, the oligonucleotide Lx has a nucleotide sequence Lx, and the oligonucleotide Ly has a nucleotide sequence Ly, the nucleotide sequence Xb is complementary to the nucleotide sequence Y, the nucleotide sequence X contains an antisense sequence that is capable of hybridizing with a target RNA, when m represents 1 and n represents 0,
the nucleotide sequence Xz contains an antisense sequence that is capable of hybridizing with a target RNA, when m represents 0 and n represents 1,
the nucleotide sequence Yz contains an antisense sequence that is capable of hybridizing with a target RNA, and in the case of having two or more of the antisense sequences, the target RNA hybridized by each antisense sequence portion may each be the same or different}, and Xb and Y hybridize.

2. The single-stranded oligonucleotide described in 1., wherein Xb bonds to Xa on the 3'-side and Y bonds to Xa on the 5'-side.

3. The single-stranded oligonucleotide described in 1., wherein Xb bonds to Xa on the 5'-side and Y bonds to Xa on the 3'-side.

4. The single-stranded oligonucleotide described in any one of 1. to 3., wherein the antisense sequence is a sequence each independently containing at least four contiguous nucleotides recognized by RNase H, or
a sequence containing at least one sugar-modified nucleotide, and not containing four contiguous deoxyribonucleotides.

5. The single-stranded oligonucleotide described in 4., wherein at least one of the antisense sequence is a sequence containing at least four contiguous nucleotides recognized by RNase H, and the antisense sequence portion contains a sugar-modified nucleotide bound adjacent to the 5'-side and the 3'-side of the sequence portion containing the at least four contiguous nucleotides recognized by RNase H.

6. The single-stranded oligonucleotide described in any one of 1. to 5., wherein the antisense sequence portion contains a phosphorothioate bond.

7. The single-stranded oligonucleotide described in any one of 1. to 6., wherein the antisense sequence is a sequence composed of 10 to 30 nucleotides containing at least one deoxyribonucleotide.

8. The single-stranded oligonucleotide described in any one of 1. to 7., wherein the nucleotide sequence Y is a sequence containing at least four contiguous nucleotides cleaved by RNase H.

9. The single-stranded oligonucleotide described in any one of 1. to 8., wherein the oligonucleotide Y contains one or a plurality of sugar-modified nucleotides on at least one of the 5'-side and the 3'-side of the oligonucleotide Y.

10. The single-stranded oligonucleotide described in any one of 1. to 9., wherein m is 0 and n is 0.

11. The single-stranded oligonucleotide described in any one of 1. to 9., wherein m is 0 and n is 1.

12. The single-stranded oligonucleotide described in 11., wherein the nucleotides contained in the oligonucleotide Ly are mutually coupled through a phosphodiester bond.

13. The single-stranded oligonucleotide described in 11. or 12., wherein the oligonucleotide Ly is DNA or RNA.

14. The single-stranded oligonucleotide described in any one of 1. to 9., wherein m is 1 and n is 0.

15. The single-stranded oligonucleotide described in 14., wherein the nucleotides contained in the oligonucleotide Lx are mutually coupled through a phosphodiester bond.

16. The single-stranded oligonucleotide described in 14. or 15., wherein the oligonucleotide Lx is DNA or RNA.

17. The single-stranded oligonucleotide described in any one of 1. to 16., which further contains a group derived from a functional molecule having at least one function selected from the group consisting of a labeling function, a purifying function and a target site delivery function.

18. The single-stranded oligonucleotide described in 17., wherein the functional molecule is selected from the group consisting of sugars, lipids, peptides, proteins and a derivative thereof.

19. The single-stranded oligonucleotide described in 17. or 18., wherein the functional molecule is a lipid selected from the group consisting of cholesterol, tocopherol and tocotrienol.

20. The single-stranded oligonucleotide described in 17. or 18., wherein the functional molecule is a sugar derivative that interacts with an asialoglycoprotein receptor.

21. The single-stranded oligonucleotide described in 17. or 18., wherein the functional molecule is a peptide or protein selected from the group consisting of receptor ligands and antibodies.

22. A pharmaceutical composition containing the single-stranded oligonucleotide described in any one of 1. to 21., and a pharmacologically acceptable carrier.

23. A method for controlling a function of a target RNA, including a step for contacting the single-stranded oligonucleotide described in any one of 1. to 21. with a cell.

24. A method for controlling a function of a target RNA in a mammal, including a step for administering a pharmaceutical composition containing the single-stranded oligonucleotide described in any one of 1. to 21. to the mammal.

25. A method for controlling expression of a target gene, including a step for contacting the single-stranded oligonucleotide described in any one of 1. to 21. with a cell.

26. A method for controlling expression of a target gene in a mammal, including a step for administering a pharmaceutical composition containing the single-stranded oligonucleotide described in any one of 1. to 21. to the mammal.

27. A method for producing the single-stranded oligonucleotide described in any one of 1. to 21., including a step for elongating the nucleotide strand at the 3'-end or 5'-end of an oligonucleotide containing at least one of X and Y.

Effects of the Invention

According to the present invention, an oligonucleotide can be provided that is able to control a target RNA with high efficiency.

The single-stranded oligonucleotide of the present invention is able to effectively control expression of a target gene by its constituent antisense oligonucleotide, and is useful as a nucleic acid pharmaceutical.

Figure 1:
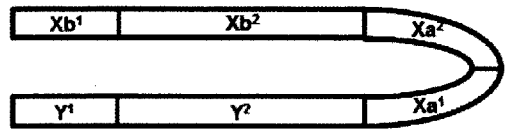
FIG. 1 is a conceptual diagram representing one aspect in which Xb and Y of an example of the present embodiment in the form of a single-stranded oligonucleotide hybridize within the molecule thereof.

The terms used in the present description are used in the sense in which they are ordinarily used in the art unless specifically indicated otherwise. The following provides an explanation of terms used in the present description. Furthermore, the terms used in the present description have the same meaning both in the case they are used alone and in the case they are used in conjunction with other terms unless specifically indicated otherwise.

"Antisense effect" refers to controlling the function of a target RNA by hybridizing a target RNA selected corresponding to a target gene and, for example, an oligonucleotide having a sequence complementary to a partial sequence thereof. For example, in the case the target RNA is mRNA, an antisense effect refers to translation of the above-mentioned target RNA being inhibited by hybridization, an effect that converts a splicing function such as exon skipping, or the above-mentioned target RNA being degraded as a result of recognition of a hybridized portion.

Although examples of oligonucleotides in which the above-mentioned antisense effect is demonstrated include DNA and oligodeoxyribonucleotides, oligonucleotides in which an antisense effect is demonstrated are not limited thereto, but rather may be RNA, oligoribonucleotides or oligonucleotides that have been designed to normally demonstrate an antisense function.

"Target RNA" refers to mRNA, mRNA precursor or ncRNA, and includes mRNA transcribed from genomic DNA encoding a target gene, mRNA not subjected to base modification, and mRNA precursor or ncRNA that have not been subjected to splicing. There are no particular limitations on the "target RNA" for which the function thereof is controlled by an antisense effect, and examples thereof include RNA associated with genes for which expression increases in various diseases. The "target RNA" may be any RNA synthesized by DNA-dependent RNA polymerase, and is preferably mRNA or mRNA precursor. It is more preferably mammal mRNA or mRNA precursor and even more preferably human mRNA or mRNA precursor.

"Hybridize" refers to the act of forming a double-strand between oligonucleotides containing complementary sequences or groups derived from those oligonucleotides, and constitutes a phenomenon in which oligonucleotides containing complementary sequences or groups derived from those oligonucleotides form a double strand.

"Complementary" refers to that two nucleic acid bases are able to form a Watson-Crick base pair (naturally-occurring base pair) or non-Watson-Crick base pair (such as a Hoogsteen base pair) via hydrogen bonds. Two oligonucleotides or groups derived from those oligonucleotides are able to "hybridize" in the case their sequences are complementary. Although it is not necessary for sequences to be completely complementary in order for two oligonucleotides or groups derived from those oligonucleotides to hybridize, complementarity for two oligonucleotides or groups derived from those oligonucleotides to hybridize is preferably 70% or more, more preferably 80% or more and even more preferably 90% or more (such as 95%, 96%, 97%, 98% or 99% or more). Sequence complementarity can be determined by using a computer program that automatically identifies the partial sequences of oligonucleotides. One example of software used for that purpose is OligoAnalyzer available from Integrated DNA Technologies. This program can also be accessed online from a Web site. A person with ordinary skill in the art is able to easily determine conditions (such as temperature or salt concentration) for enabling hybridization of two oligonucleotides or groups derived from those oligonucleotides. In addition, a person with ordinary skill in the art can easily design an antisense oligonucleotide complementary to target RNA by, for example, using software such as the BLAST program based on information of the nucleotide sequence data of the target RNA. With respect to the BLAST program, literature such as Proceedings of the National Academy of Science of the United States of America (1990, Vol. 87, pp. 2264-2268; 1993, Vol. 90, pp. 5873-5877) and the Journal of Molecular Biology (1990, Vol. 215, p. 403) can be referred to.

A "nucleotide" indicates a molecule capable of serving as a structural unit of a nucleic acid (oligonucleotide), and normally has a base as constituents thereof. A nucleotide is composed of, for example, a sugar, a base and a phosphoric acid. Nucleotides include ribonucleotides, deoxyribonucleotides and sugar-modified nucleotides mentioned later.

An "oligonucleotide" refers to a molecule having a structure in which one or more above-mentioned nucleotides are polymerized. When the "oligonucleotide" is composed of one nucleotide, that oligonucleotide can also be referred to as a "nucleotide".

Nucleotides contained in the "single-stranded oligonucleotide" molecule of the present invention are each independently coupled to each other by a phosphodiester bond or a modified phosphodiester bond mentioned later. The nucleotide at the 3'-end of the single-stranded oligonucleotide molecule of the present invention preferably has a hydroxyl group or a phosphate group at the 3'-position, more preferably has a hydroxyl group, and usually has a hydroxyl group. The nucleotide at the 5'-end of the single-stranded oligonucleotide molecule preferably has a hydroxyl group or a phosphate group at the 5'-position, more preferably has a hydroxyl group, and usually has a hydroxyl group.

A "group derived from an oligonucleotide" refers to the partial structure of an oligonucleotide formed by removing a hydrogen atom or hydroxyl group and the like from at least one of the hydroxyl groups on the 3'-end or 5'-end of the above-mentioned oligonucleotide, and coupled with the other group (for example, a linking group, or other groups derived from an oligonucleotide) by forming a phosphodiester bond or a modified phosphodiester bond indirectly through a covalent bond. The above-mentioned hydroxyl group at the 3'-end or 5'-end refers to a hydroxyl group possessed by a phosphate group. For example, a group in which a hydrogen atom is removed from the hydroxyl group at the 3'-end of the oligonucleotide and a group in which a hydroxyl group is removed from the phosphate group at the 5'-end of another oligonucleotide forms a phosphodiester bond or a modified phosphodiester bond.

A "nucleotide sequence" refers to the base sequence of nucleotides that compose an oligonucleotide.

A "nucleotide sequence portion" refers to a partial structure of a region having the above-mentioned nucleotide sequence in an oligonucleotide strand.

In the present description, a "nucleotide sequence" containing or not containing a predetermined nucleotide or oligonucleotide strand has the same meaning as the corresponding "sequence portion containing nucleotide" containing or not containing the nucleotide or the oligonucleotide strand.

A "sequence portion" refers to a partial structure of an oligonucleotide strand. For example, a sequence portion containing nucleotides is a partial structure of a region of an oligonucleotide strand that contains the nucleotides.

A nucleotide sequence being a sequence of selected from predetermined nucleotides and the predetermined nucleotides being contiguous nucleotides has the same meaning as the corresponding nucleotide sequence portion being a sequence portion selected from those nucleotides and the nucleotides being a contiguous sequence portion, respectively.

A "deoxyribonucleotide" refers to a molecule in which among the above-mentioned "nucleotides", the sugar is 2'-deoxyribose, a base is bound to a carbon atom at the 1'-position of 2'-deoxyribose, and a phosphate group is bound to the 3'-position or 5'-position. The deoxyribonucleotide in the present invention may be a naturally-occurring deoxyribonucleotide or a deoxyribonucleotide in which the base moiety or phosphodiester bond portion of the naturally-occurring deoxyribonucleotide is modified. The modification of the base moiety and the modification of the phosphodiester bond portion may be performed in combination of two or more kinds on single deoxyribonucleotide. The above-mentioned modified deoxyribonucleotide is described in, for example, the Journal of Medical Chemistry (2016, Vol. 59, No. 21, pp. 9645-9667), Medical Chemistry Communications (2014, Vol. 5, pp. 1454-1471) and Future Medicinal Chemistry (2011, Vol. 3, No. 3, pp. 339-365).

When the above-mentioned "deoxyribonucleotide" composes the single-stranded oligonucleotide molecule of the present invention, normally the 3'-position of the deoxyribonucleotide is coupled to another nucleotide through a phosphodiester bond or a modified phosphodiester bond (for example, a phosphorothioate bond), and the 5'-position of the deoxyribonucleotide is coupled to another nucleotide through a phosphodiester bond or a modified phosphodiester bond (for example, a phosphorothioate bond). The deoxyribonucleotide at the 3'-end of the single-stranded oligonucleotide molecule of the present invention preferably has a hydroxyl group or a phosphate group at the 3'-position, and the 5'-position is as previously described. The deoxyribonucleotide at the 5'-end of the single-stranded oligonucleotide molecule preferably has a hydroxyl group or a phosphate group at the 5'-position, and the 3'-position is as previously described.

An "oligodeoxyribonucleotide" refers to an oligonucleotide that is composed of the above-mentioned deoxyribonucleotides. Deoxyribonucleotides composing the oligodeoxyribonucleotide may each be the same or different.

"DNA" refers to an oligonucleotide that is composed of naturally-occurring deoxyribonucleotides. The naturally-occurring deoxyribonucleotides that compose the DNA may each be the same or different.

A "ribonucleotide" refers to a molecule in which a sugar is ribose in the above-mentioned "nucleotide", a base is bound to a carbon atom at the 1'-position of the ribose, and a phosphate group is possessed at the 2'-position, 3'-position or 5'-position. The ribonucleotide in the present invention may be a naturally-occurring ribonucleotide or a ribonucleotide in which a base moiety of the naturally-occurring ribonucleotide or a phosphodiester bond portion is modified. Modification of the base moiety or modification of the phosphodiester bond portion may be carried out on a combination of a plurality of types of modifications on a single ribonucleotide. The above-mentioned modified ribonucleotide is described in, for example, the Journal of Medical Chemistry (2016, Vol. 59, No. 21, pp. 9645-9667), Medical Chemistry Communications (2014, Vol. 5, pp. 1454-1471) and Future Medicinal Chemistry (2011, Vol. 3, No. 3, pp. 339-365).

When the above-mentioned "ribonucleotide" composes a single-stranded oligonucleotide molecule of the present invention, typically the 3'-position of the ribonucleotide is coupled to another nucleotide through a phosphodiester bond or a modified phosphodiester bond (for example, a phosphorothioate bond), and the 5'-position of the ribonucleotide is coupled to another nucleotide through a phosphodiester bond or a modified phosphodiester bond (for example, a phosphorothioate bond). The ribonucleotide at the 3'-end of the single-stranded oligonucleotide molecule of the present invention preferably has a hydroxyl group or a phosphate group at the 3'-position thereof, and the 5'-position is as previously described. The ribonucleotide at the 5'-end of the single-stranded oligonucleotide molecule preferably has a hydroxyl group or a phosphate group at the 5'-position thereof, and the 3'-position is as previously described.

An "oligoribonucleotide" refers to an oligonucleotide that is composed of the above-mentioned ribonucleotide. The ribonucleotide that compose the oligoribonucleotide may each be the same or different.

"RNA" refers to an oligonucleotide that is composed of naturally-occurring ribonucleotides. The naturally-occurring ribonucleotides that compose the RNA may each be the same or different.

"Sugar-modified nucleotide" refers to a nucleotide in which the sugar moiety of the above-mentioned deoxyribonucleotide or ribonucleotide is partially substituted with one or more substituents, the entire sugar backbone thereof has been replaced with a sugar backbone differing from ribose and 2'-deoxyribose (for example, a 5- or 6-membered sugar backbone such as hexitol and threose), the entire sugar backbone thereof or a portion of the ring of the sugar backbone has been replaced with a 5- to 7-membered saturated or unsaturated ring (for example, cyclohexane, cyclohexene, morpholine, and the like) or with a partial structure (for example, peptide structure) that allows the formation of a 5- to 7-membered ring by hydrogen bonding, or the ring of the sugar moiety is ring-opened, or further, the ring-opened portion is modified. A base moiety of a "sugar-modified nucleotide" may be a naturally-occurring base or a modified base. In addition, a phosphodiester bond moiety of a "sugar-modified nucleotide" may be a phosphodiester bond or a modified phosphodiester bond. Modification of a base moiety or modification of a phosphodiester bond portion on a single sugar-modified nucleotide may be carried out on a combination of a plurality of types of modifications. Modification of the above-mentioned ring-opened portion may include, for example, halogenation, alkylation (for example, methylation, and ethylation), hydroxylation, amination, and thionation as well as demethylation.

A "sugar-modified nucleotide" may be a bridged nucleotide or non-bridged nucleotide. Examples of sugar-modified nucleotides include nucleotides disclosed as being preferable for use in an antisense method in, for example, Japanese Unexamined Patent Publication No. H10-304889, International Publication No. WO 2005/021570, Japanese Unexamined Patent Publication No. H10-195098, Japanese Translation of PCT Application No. 2002-521310, International Publication No. WO 2007/143315, International Publication No. WO 2008/043753, International Publication No. WO 2008/029619 or International Publication No. 2008/049085 (these documents are to be collectively referred to as "antisense method-related documents"). The above-mentioned documents disclose nucleotides such as hexitol nucleotides (HNA), cyclohexene nucleotides (CeNA), peptide nucleic acids (PNA), glycol nucleic acids (GNA), threose nucleotides (TNA), morpholino nucleic acids, tricyclo-DNA (tcDNA), 2'-O-methyl nucleotides, 2'-O-methoxyethyl (2'-MOE) nucleotides, 2'-O-aminopropyl (2'-AP) nucleotides, 2'-fluoronucleotides, 2'-F-arabinonucleotides (2'-F-ANA), bridged nucleotides (BNA (Bridged Nucleic Acid)) and 2'-O-{(N-methylcarbamoyl)ethyl} (2'-MCE) nucleotides. In addition, sugar-modified nucleotides are also disclosed in the literature such as the Journal of Medical Chemistry (2016, Vol. 59, No. 21, pp. 9645-9667), Medicinal Chemistry Communications (2014, Vol. 5, 1454-1471) or Future Medicinal Chemistry (2011, Vol. 3, No. 3, pp. 339-365).

When the above-mentioned "sugar-modified nucleotide" composes the single-stranded oligonucleotide molecule of the present invention, for example, the 3'-position of the sugar-modified nucleotide is coupled to another nucleotide through a phosphodiester bond or modified phosphodiester bond (for example, a phosphorothioate bond), and the 5'-position of the sugar-modified nucleotide is coupled to another nucleotide through a phosphodiester bond or modified phosphodiester bond (for example, a phosphorothioate bond). A sugar-modified nucleotide on the 3'-end of the single-stranded oligonucleotide molecule of the present invention preferably has, for example, a hydroxyl group or a phosphate group at the 3'-position thereof, and the 5'-position is as previously described. A sugar-modified nucleotide on the 5'-end of the single-stranded oligonucleotide preferably has, for example, a hydroxyl group or a phosphate group at the 5'-positon thereof and the 3'-position is as previously described.

The base moieties in a deoxyribonucleotide, ribonucleotide and sugar-modified nucleotide are preferably at least one type selected from the group consisting of adenine (A), guanine (G), thymine (T), cytosine (C), uracil (U) and 5-methyl-cytosine (5-me-C).

Examples of modifications of a base moiety in a deoxyribonucleotide, ribonucleotide and sugar-modified nucleotide include halogenation, methylation, ethylation, n-propylation, isopropylation, cyclopropylation, n-butylation, isobutylation, s-butylation, t-butylation, cyclobutylation, hydroxylation, amination, thionation and demethylation. Specific examples include 5-methylation, 5-fluorination, 5-bromination, 5-iodination and N4-methylation of cytosine, 2-thionation, 5-demethylation, 5-fluorination, 5-bromination and 5-iodination of thymine, 2-thionation, 5-fluorination, 5-bromination and 5-iodination of uracil, N6-methylation and 8-bromination of adenine, and N2-methylation and 8-bromination of guanine. In addition, examples of modification of sugar moieties in nucleotides are disclosed in the Journal of Medicinal Chemistry (2016, Vol. 59, No. 21, pp. 9645-9667), Medicinal Chemistry Communications (2014, Vol. 5, 1454-1471) and Future Medicinal Chemistry (2011, Vol. 3, No. 3, pp. 339-365), and these can be used in the base moieties of deoxyribonucleotides, ribonucleotides and sugar-modified nucleotides.

Examples of modification of a phosphodiester bond moiety in deoxyribonucleotides, ribonucleotides and sugar-modified nucleotides include phosphorothioation, methylphosphonation (including chiral-methylphosphonation), methylthio-phosphonation, phosphorodithioation, phosphoroamidation, phosphorodiamidation, phosphoroamidothioation and boranophosphorylation. In addition, examples of the modification of the phosphodiester bond moiety in nucleotides are described in, for example, the Journal of Medicinal Chemistry (2016, Vol. 59, No. 21, pp. 9645-9667), Medicinal Chemistry Communications (2014, Vol. 5, pp. 1454-1471) and Future Medicinal Chemistry (2011, Vol. 3, No. 3, pp. 339-365), and these can be used at the phosphodiester bond moiety in deoxyribonucleotides, ribonucleotides and sugar-modified nucleotides.

Examples of modifications in which a sugar moiety of a deoxyribonucleotide or ribonucleotide is partially substituted with a single substituent include 2'-O-methylation, 2'-O-methoxyethylation (2'-MOE), 2'-O-aminopropylation (2'-AP), 2'-fluorination and 2'-O-{(N-methylcarbamoyl)ethyl}ation (2'-MCE).

A "bridged nucleotide" refers to a sugar-modified nucleotide in which a bridging unit has been substituted by substitutions at two locations in a sugar moiety, and an example thereof includes nucleotide that has been bridged at the 2'-position and 4'-position.

A nucleotide that has been bridged at the 2'-position and 4'-position (2',4'-BNA) is only required to be a nucleotide having a sugar moiety in which the carbon atom at the 2'-position and the carbon atom at the 4'-position are bridged with two or more atoms, and examples thereof include nucleotides having a sugar moiety that has been bridged at a $C_{2-6}$ alkylene group (wherein the alkylene group is either unsubstituted or substituted with one or more substituents selected from the group consisting of a halogen atom, an oxo group and a thioxo group, and one or two methylene groups of the alkylene group are not replaced or are independently replaced with a group selected from the group consisting of —O—, —NR$^1$— (wherein, R$^1$ represents a hydrogen atom, a $C_{1-6}$ alkyl group or a halo-$C_{1-6}$ alkyl group) and —S—).

The group bridged at the 2'-position and 4'-position of 2',4'-BNA by combining the above-mentioned substitutions and replacements may contain a group represented by —C(=O)—O—, —O—C(=O)—NR$^1$— (R$^1$ represents a hydrogen atom, a $C_{1-6}$ alkyl group or a halo-$C_{1-6}$ alkyl group), —C(=O)—NR$^1$— (R$^1$ represents a hydrogen atom, a $C_{1-6}$ alkyl group or a halo-$C_{1-6}$ alkyl group), —C(=S)—NR$^1$— (R$^1$ represents a hydrogen atom, a $C_{1-6}$ alkyl group or a halo-$C_{1-6}$ alkyl group), and the like.

Examples of such a BNA include Locked Nucleic Acid® also referred to as LNA, α-L-methyleneoxy(4'-CH$_2$—O-2') BNA or β-D-methyleneoxy(4'-CH$_2$—O-2')BNA, ethyleneoxy(4'-(CH$_2$)$_2$—O-2')BNA also referred to as ENA, β-D-thio(4'-CH$_2$—S-2')BNA, aminoxy(4'-CH$_2$—O—N(R$^{11}$)-2') BNA (wherein, R$^{11}$ represents H or CH$_3$), oxyamino(4'-CH$_2$—N(R$^{12}$)—O-2')BNA also referred to as 2',4'-BNA$^{NC}$ (wherein, R$^{12}$ represents H or CH$_3$), 2',4'-BNA$^{COC}$, 3'-amino-2',4'-BNA, 5'-methyl BNA, (4'-CH(CH$_3$)—O-2') BNA also referred to as cEt-BNA, (4'-CH(CH$_2$OCH$_3$)—O-2')BNA also referred to as cMOE-BNA, amide-type BNA (4'-C(=O)—N(R$^{13}$)-2')BNA (wherein, R$^{13}$ represents H or CH$_3$) also referred to as AmNA, and other BNA known among persons with ordinary skill in the art.

A "nucleotide of which at least one of a sugar moiety, base moiety and phosphate moiety has been modified" refers to a deoxyribonucleotide, in which at least one of the base moiety and phosphate moiety of a naturally-occurring deoxyribonucleotide has been modified, a ribonucleotide in which at least one of a base moiety and phosphate moiety of a naturally-occurring ribonucleotide has been modified, or a sugar-modified nucleotide.

"n-" refers to normal, "s-" secondary, and "t-" tertiary.

A "halogen atom" refers to a fluorine atom, a chlorine atom, a bromine atom or an iodine atom.

A "$C_{1-6}$ alkyl group" refers to a linear or branched saturated hydrocarbon group having 1 to 6 carbon atoms, and examples thereof include a methyl group, an ethyl group, an n-propyl group, an isopropyl group, an n-butyl group, an isobutyl group, a s-butyl group, a t-butyl group, an n-pentyl group, an isopentyl group, a neopentyl group, an n-hexyl group and an isohexyl group.

A "halo-$C_{1-6}$ alkyl group" refers to a group in which a hydrogen atom at an optional position of the above-mentioned "$C_{1-6}$ alkyl group" is substituted by one or more of the above-mentioned "halogen atom(s)".

A "$C_{1-6}$ alkylene group" refers to a divalent group in which one hydrogen atom at an optional position is removed from a linear or branched saturated hydrocarbon group having 1 to 6 carbon atoms, and examples thereof include a methylene group, an ethylene (ethanediyl) group, a propane-1,3-diyl group, a propane-2,2-diyl group, a 2,2-dimethylpropane-1,3-diyl group, a hexane-1,6-diyl group and a 3-methylbutane-1,2-diyl group.

A "$C_{2-6}$ alkylene group" refers to a linear or branched divalent group having 2 to 6 carbon atoms among the above-mentioned "$C_{1-6}$ alkylene group", and examples thereof are the same as the above-mentioned "$C_{1-6}$ alkylene group" except for the methylene group.

A "$C_{2-20}$ alkylene group" refers to a divalent group in which one hydrogen atom at an optional position is removed from a linear or branched saturated hydrocarbon group having 2 to 20 carbon atoms. Similarly, a "$C_{8-12}$ alkylene group" refers to a divalent group in which one hydrogen atom at an optional position is removed from a linear or branched saturated hydrocarbon group having 8 to 12 carbon atoms.

A "$C_{2-20}$ alkenylene group" refers to a divalent group in which one hydrogen atom at an optional position is removed from a linear or branched unsaturated hydrocarbon group having 2 to 20 carbon atoms containing at least one double bond.

An "oxo group" indicates a group in which an oxygen atom is substituted via a double bond (=O). In the case an oxo group is substituted for a carbon atom, the oxo group forms a carbonyl group together with the carbon atom.

A "thioxo group" indicates a group in which a sulfur atom is substituted via a double bond (=S). In the case a thioxo group is substituted for a carbon atom, the thioxo group forms a thiocarbonyl group together with the carbon atom.

The sugar-modified nucleotide is not limited to that exemplified here. Numerous sugar-modified nucleotides are known in this field of the art, and sugar-modified nucleotides described in, for example, U.S. Pat. No. 8,299,039 of Tachas, et al. (and particularly columns 17 to 22), or the Journal of Medicinal Chemistry (2016, Vol. 59, No. 21, 9645-9667), Medicinal Chemistry Communications (2014, Vol. 5, pp. 1454-1471) or Future Medicinal Chemistry (2011, Vol. 3, No. 3, pp. 339-365), can also be used as embodiments of the present invention.

A person with ordinary skill in the art is able to suitably select and use a sugar-modified nucleotide from among such sugar-modified nucleotides in consideration of viewpoints such as antisense effect, affinity for a partial sequence of a target RNA or resistance to nuclease.

"RNase H" is generally known to be a ribonuclease that recognizes a double strand obtained by hybridizing DNA and RNA and cleaves the RNA to form single-stranded DNA. RNase H is able to recognize not limited only to a double strand obtained by hybridizing DNA and RNA, but also a double strand in which at least one of the base moiety, phosphodiester bond moiety or sugar moiety of at least one of DNA and RNA has been modified. For example, it can also recognize a double strand obtained by hybridizing an oligodeoxyribonucleotide and an oligoribonucleotide.

Accordingly, DNA can be recognized by RNase H when hybridizing with RNA. This applies similarly in the case at least one of the base moiety, phosphodiester bond moiety and sugar moiety has been modified in at least one of DNA and RNA. For example, a typical example thereof is an oligonucleotide in which a phosphodiester moiety of DNA has been modified to phosphorothioate.

RNA can be cleaved by RNase H when hybridizing with DNA. This applies similarly in the case at least one of the base moieties, phosphodiester bond moiety and sugar moiety has been modified in at least one of DNA and RNA.

Examples of modifying DNA and/or RNA able to be recognized by RNase H are described in the literature, examples of which include Nucleic Acids Research (2014, Vol. 42, No. 8, pp. 5378-5389), Bioorganic and Medicinal Chemistry Letters (2008, Vol. 18, pp. 2296-2300), Molecular Biosystems (2009, Vol. 5, pp. 838-843), Nucleic Acid Therapeutics (2015, Vol. 25, pp. 266-274) and The Journal of Biological Chemistry (2004, Vol. 279, No. 35, pp. 36317-36326).

The RNase H used in the present invention is preferably mammal RNase H, more preferably human RNase H, and particularly preferably human RNase H1.

Although there are no particular limitations on "at least four contiguous nucleotides recognized by RNase H" as long as they include four or more contiguous nucleotides and are recognized by RNase H, the contiguous nucleotides are preferably independently selected from deoxyribonucleotides and sugar-modified nucleotides, and are more preferably independently selected from deoxyribonucleotides. These contiguous nucleotides may each be the same or different.

Although there are no particular limitations on "at least four contiguous nucleotides cleaved by RNase H" as long as they include four contiguous nucleotides and are cleaved by RNase H, they include at least one ribonucleotide. In addition, the four contiguous nucleotides preferably include an oligonucleotide and more preferably include RNA. The contiguous nucleotides are more preferably independently selected from ribonucleotides. In addition, the contiguous nucleotides are more preferably mutually coupled through phosphodiester bonds. These contiguous nucleotides may each be the same or different.

Next, the following provides an explanation of an antisense sequence and an antisense sequence portion as used in the present invention.

An "antisense sequence" refers to a base sequence of nucleotides that compose an oligonucleotide capable of hybridizing with a target RNA.

An "antisense sequence portion" refers to a partial structure of an oligonucleotide strand in a region having the above-mentioned antisense sequence.

Furthermore, in the present description, an "antisense sequence" containing or not containing a predetermined nucleotide or oligonucleotide strand has the same meaning as the corresponding "antisense sequence portion" containing or not containing the nucleotide or the oligonucleotide strand.

The above-mentioned antisense sequence portion is not required to hybridize with the entire target RNA, but rather is only required to hybridize with at least a portion of the target RNA, and normally hybridizes with at least a portion of the target RNA. For example, expression of a target gene is controlled by hybridizing an oligonucleotide having an antisense sequence complementary to the partial sequence of the target RNA (such as DNA, an oligodeoxyribonucleotide or an oligonucleotide designed so as to normally demonstrated an antisense effect) with at least a portion of the target RNA. In addition, although it is not necessary to hybridize with the entire antisense sequence portion and may not hybridize with a portion thereof, hybridization with the entire antisense sequence portion is preferable.

Complementarity between the above-mentioned antisense sequence and partial sequence of target RNA is preferably 70% or more, more preferably 80% or more and even more preferably 90% or more (such as 95%, 96%, 97%, 98% or 99% or more). Although the sequences are not required to be completely complementary in order for the antisense sequence portion to hybridize with at least a portion of the target RNA, the sequences are more preferably completely complementary.

The above-mentioned antisense sequence is preferably a sequence that contains "at least four contiguous nucleotides recognized by RNase H when hybridizing with a target RNA", or a sequence "that contains at least one sugar-modified nucleotide but does not contain four contiguous deoxyribonucleotides".

A person with ordinary skill in the art is able to easily determine a base sequence compatible with an antisense sequence "able to hybridize with target RNA" by using the BLAST program and the like. This applies similarly to a nucleotide sequence compatible with "at least four contiguous nucleotides recognized by RNase H when hybridizing with a target RNA".

"At least four contiguous nucleotides recognized by RNase H when hybridizing with a target RNA" are normally 4 to 30 contiguous nucleotides, preferably 4 to 20 contiguous nucleotides, more preferably 5 to 16 contiguous nucleotides, even more preferably 6 to 12 contiguous nucleotides, and particularly preferably 8 to 10 contiguous nucleotides. The above-mentioned contiguous nucleotides are preferably independently selected from deoxyribonucleotides and sugar-modified nucleotides, and are more preferably independently selected from deoxyribonucleotides. The above-mentioned contiguous nucleotides are particularly preferably 8 to 10 contiguous deoxyribonucleotides. These contiguous nucleotides may each be the same or different.

In addition, from the viewpoint of superior pharmacokinetics, at least one of the nucleotides among the contiguous nucleotides is preferably phosphorothioated. More preferably, at least one of the nucleotides on the 3'-end and 5'-end of these contiguous nucleotides is phosphorothioated, and further preferably, both of the 3'-end and 5'-end are phosphorothioated. Even more preferably, 80% of nucleotides among these contiguous nucleotides are phosphorothioated, and still more preferably, 90% of the nucleotides are phosphorothioated. Particularly preferably, all of the contiguous nucleotides are phosphorothioated.

In the case the antisense sequence is a sequence that contains "at least four contiguous nucleotides recognized by RNase H when hybridizing with a target RNA", 1 to 10 sugar-modified nucleotides are preferably bound adjacent to at least one of the 3'-side and 5'-side of the "at least four contiguous nucleotides recognized by RNase H when hybridizing with a target RNA" from the viewpoint of increasing affinity for a partial sequence of the target RNA or increasing resistance to nuclease, more preferably 2 to 5 sugar-modified nucleotides are bound adjacent to at least one of the 3'-side and 5'-side, and more preferably 2 to 3 sugar-modified nucleotides are bound adjacent to at least one of the 3'-side and 5'-side. Here, although one or a plurality of deoxyribonucleotides, ribonucleotides or both may be contained between a plurality of sugar-modified nucleotides at least on one of the 3'-side and 5'-side, the plurality of sugar-modified nucleotides are preferably contiguous. In addition, the one or a plurality of sugar-modified nucleotides are preferably bound adjacent to both the 3'-side and 5'-side of the "at least four contiguous nucleotides recognized by RNase H when hybridizing with a target RNA". In the case a plurality of sugar-modified nucleotides are bound adjacent to at least one of the 3'-side and 5'-side of the "at least four contiguous nucleotides recognized by RNase H when hybridizing with a target RNA", "a plurality of sugar-modified nucleotides are bound adjacent to" refers to that the plurality of sugar-modified nucleotides and an oligonucleotide strand composed of deoxyribonucleotides and ribonucleotides contained between the plurality of sugar-modified nucleotides are bound adjacent. In the case a plurality of sugar-modified nucleotides are bound adjacent to at least one of the 3'-side and 5'-side, each sugar-modified nucleotide may each be the same or different.

Although a sugar-modified nucleotide portion bound adjacent to at least one of the 3'-side and 5'-side of the above-mentioned "at least four contiguous nucleotides recognized by RNase H when hybridizing with a target RNA" may or may not hybridize with the target RNA, the sugar-modified nucleotide portion preferably hybridizes with the target RNA from the same viewpoint as previous described. In the case where the antisense sequence portion contains the "at least four contiguous nucleotides recognized by RNase H when hybridizing with a target RNA", one or a plurality of sugar-modified nucleotides are bound adjacent to at least one of the 3'-side and 5'-side and the sugar-modified nucleotide portion hybridizes with the target RNA, the one or a plurality of the sugar-modified nucleotide portion is also a part of the antisense sequence portion. That is, the "at least four contiguous nucleotides recognized by RNase H when hybridizing with a target RNA", and the one or a plurality of the sugar-modified nucleotide bound adjacent to the 3'-side and the 5'-side constitute the antisense sequence portion. The antisense sequence portion is called a gapmer.

In addition, from the viewpoint of superior pharmacokinetics, at least one sugar-modified nucleotide portion bound adjacent to at least one of the 3'-side and 5'-side of the above-mentioned "at least four contiguous nucleotides recognized by RNase H when hybridizing with a target RNA" is preferably phosphorothioated, more preferably at least one sugar-modified nucleotide portion adjacent to the 3'-side and at least one sugar-modified nucleotide portion adjacent to the 5'-side are phosphorothioated, even more preferably 50% are phosphorothioated, and still more preferably 80% are phosphorothioated. In addition, preferably all are phosphorothioated. In the case a plurality of sugar-modified nucleotides are adjacent to the 3'-side, bonds between the nucleotides are preferably phosphorothioated, and this applies similarly to the case a plurality of sugar-modified nucleotides are adjacent to the 5'-side.

The gapmer is preferably an oligonucleotide in which an oligonucleotide composed of 1 to 10 sugar-modified nucleotides, an oligodeoxyribonucleotide composed of 4 to 30 deoxyribonucleotides, and an oligonucleotide composed of 1 to 10 sugar-modified nucleotides are coupled in this order, more preferably an oligonucleotide in which an oligonucleotide composed of 2 to 5 sugar-modified nucleotides, deoxyribonucleotides composed of 4 to 20 oligodeoxyribonucleotides, and an oligonucleotide composed of 2 to 5 sugar-modified nucleotides are coupled in this order, further preferably an oligonucleotide in which an oligonucleotide composed of 2 or 3 sugar-modified nucleotides, an oligodeoxyribonucleotide composed of 5 to 15 deoxyribonucleotides, and an oligonucleotide composed of 2 or 3 sugar-modified nucleotides are coupled in this order, and particularly preferably an oligonucleotide in which an oligonucleotide composed of 2 or 3 sugar-modified nucleotides, an oligodeoxyribonucleotide composed of 8 to 12 deoxyribonucleotides, and an oligonucleotide composed of 2 or 3 sugar-modified nucleotides are coupled in this order. As the other embodiment, it is particularly preferably an oligonucleotide in which an oligonucleotide composed of 4 or 5 sugar-modified nucleotides, an oligodeoxyribonucleotide composed of 8 to 12 deoxyribonucleotides, and an oligonucleotide composed of 4 or 5 sugar-modified nucleotides are coupled in this order.

In the case the antisense sequence is a sequence that "contains at least one sugar-modified nucleotide but does not contain four contiguous deoxyribonucleotides", although the antisense sequence portion may contain or may not contain a ribonucleotide and may contain or may not contain a deoxyribonucleotide, it does contain at least one sugar-modified nucleotide, but does not contain four contiguous deoxyribonucleotides. The antisense sequence portion is called a mixmer. The antisense sequence portion is preferably a partial structure of an oligonucleotide that is composed of nucleotides independently selected from deoxyribonucleotides and sugar-modified nucleotides, and the content percentage of sugar-modified nucleotides is, for example, 25% or more. The content percentage of sugar-modified nucleotides is more preferably 30% or more and even more preferably 50% or more from the viewpoint of increasing affinity to a partial sequence of a target RNA or increasing resistance to nuclease. From the same viewpoint, at least one of the nucleotide on the 3'-side and the nucleotide on the 5'-side of this antisense sequence portion is preferably a sugar-modified nucleotide, and the nucleotide on the 3'-side and the nucleotide on the 5'-side are more preferably sugar-modified nucleotides.

In another aspect, the content percentage of the sugar-modified nucleotides of the above-mentioned antisense sequence portion is preferably 100%.

The antisense sequence portion that "contains at least one sugar-modified nucleotide but does not contain four contiguous deoxyribonucleotides" more preferably does not contain three contiguous deoxyribonucleotides.

The antisense sequence portion (mixmer) that "contains at least one sugar-modified nucleotide but does not contain four contiguous deoxyribonucleotides" is normally 4 to 30 contiguous nucleotides, preferably 8 to 25 contiguous nucleotides, and more preferably 10 to 20 contiguous nucleotides. These contiguous nucleotides may each be the same or different.

In addition, from the viewpoint of superior pharmacokinetics, among the nucleotides composing the antisense sequence portion (mixmer) that "contains at least one sugar-modified nucleotide but does not contain four contiguous deoxyribonucleotides", at least one of the nucleotides is preferably phosphorothioated. More preferably, at least one of the nucleotides on the 3'-end and 5'-end of the antisense sequence portion is phosphorothioated. Among the bonds between nucleotides contained in the antisense sequence portion, more preferably 80% are phosphorothioated, even more preferably 90% are phosphorothioated, and particularly preferably all are phosphorothioated.

Although the "sugar-modified nucleotide" contained in the antisense sequence portion is only required to be a nucleotide for which affinity to a partial sequence of target RNA has been increased or resistance to nuclease has been increased as a result of substitution and the like, it is preferably a 2'-O-methyl nucleotide, 2'-O-methoxyethyl (2'-MOE) nucleotide, 2'-O-aminopropyl (2'-AP) nucleotide, 2'-fluoronucleotide, 2'-F-arabinonucleotide (2'-F-ANA), bridged nucleotide (BNA (Bridged Nucleic Acid)) or 2'-O-methylcarbamoylethyl (2'-MCE) nucleotide, and more preferably BNA or 2'-O-methyl nucleotide, still more preferably LNA containing a partial structure represented by the following formula (II) or 2'-O-methyl nucleotide, and particularly preferably LNA. The "sugar-modified nucleotide" contained in the antisense sequence portion is particularly preferably 2'-MOE-ated nucleotide and 2'-MCE-ated nucleotide in addition to the above-mentioned bridged nucleotide.

[Formula 3]

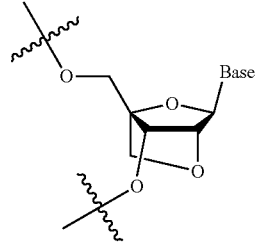

(I)

In the above formula, Base represents a base moiety and is a purin-9-yl group or 2-oxopyrimidin-1-yl group, and the purin-9-yl group and 2-oxopyrimidin-1-yl group may or may not be modified. Here, the 2-oxopyrimidin-1-yl group has the same meaning as a 2-oxo-1H-pyrimidin-1-yl group. In addition, the purin-9-yl group and the 2-oxopyrimidin-1-yl group respectively include tautomers thereof.

The types, numbers and locations of sugar-modified nucleotides, deoxyribonucleotides and ribonucleotides in the antisense sequence portion can have an effect on the antisense effect and the like demonstrated by the single-stranded oligonucleotide disclosed herein. Although the types, numbers and locations thereof are unable to be unconditionally defined since they differ according to the sequence and so forth of the target RNA, a person with ordinary skill in the art is able to determine a preferable aspect thereof while referring to the above-mentioned descriptions in the literature relating to antisense methods. In addition, if the antisense effect demonstrated by the single-stranded oligonucleotide following modification of a base moiety, sugar moiety or phosphodiester bond moiety is measured and the resulting measured value is not significantly lower than that of the single-stranded oligonucleotide prior to modification (such as if the measured value of the single-stranded oligonucleotide following modification is 30% or more of the measured value of the single-stranded oligonucleotide prior to modification), then that modification can be evaluated as a preferable aspect. As is indicated in, for example, the examples to be subsequently described, measurement of antisense effect can be carried out by introducing a test oligonucleotide into a cell and the like, and measuring the expression level of target RNA, expression level of cDNA associated with the target RNA or the amount of a protein associated with the target RNA, which is controlled by the antisense effect demonstrated by the test oligonucleotide optionally using a known technique such as northern blotting, quantitative PCR or western blotting.

Two nucleotides at least on one side of the 3'-side and 5'-side of the antisense sequence portion that "contains at least one sugar-modified nucleotide but does not contain four contiguous deoxyribonucleotides" are preferably sugar-modified nucleotides, and the sugar-modified nucleotides are preferably bridged nucleotides and particularly preferably LNA. When two nucleotides on the 3'-side of the antisense sequence portion are sugar-modified nucleotides, two or more of the three nucleotides on the 5'-side are preferably sugar-modified nucleotides and are preferably coupled in any order indicated below in order starting from an end side of the antisense sequence portion. When two nucleotides on the 5'-side of the antisense sequence portion are sugar-modified nucleotides, two or more of the three nucleotides on the 3'-side are preferably sugar-modified nucleotides and are preferably coupled in any order indicated below in order starting from an end side of the antisense sequence portion. Furthermore, in these orders, the left side indicates the end side of the antisense sequence portion, while the right side indicates the inside of the antisense sequence portion. The sugar-modified nucleotide is preferably a bridged nucleotide and particularly preferably LNA.

Sugar-modified nucleotide-sugar-modified nucleotide-sugar-modified nucleotide

Sugar-modified nucleotide-sugar-modified nucleotide-deoxyribonucleotide

Sugar-modified nucleotide-deoxyribonucleotide-sugar-modified nucleotide

Next, the following provides an explanation of the single-stranded oligonucleotide molecule in the present invention. The single-stranded oligonucleotide of the present invention contains X and Y. Examples of the embodiment of the single-stranded oligonucleotides of the present invention include an embodiment wherein both of Xz and Lx, and Yz and Ly are not contained (in the above-mentioned formula (I), m is 0, and n is 0), an embodiment wherein Xz and Lx are not contained, and Yz and Ly are contained (in the above-mentioned formula (I), m is 0, and n is 1), and an embodiment wherein Xz and Lx are contained, and Yz and Ly are not contained (in the above-mentioned formula (I), m is 1, and n is 0).

The following provides an explanation of Xa, Xb, X, Y, Xz and Yz in the present invention. Although the present invention has several embodiments, an explanation is first provided of commonalities there between.

Xa represents a group derived from an oligonucleotide Xa composed of 1 to 40 nucleotides independently selected from the group consisting of deoxyribonucleotides, ribonucleotides and sugar-modified nucleotides, and the deoxyribonucleotides, ribonucleotides and sugar-modified nucleotides are each independently not modified, or modified at least one of a base moiety and phosphate moiety. The oligonucleotide Xa contains at least one sugar-modified nucleotide. The oligonucleotide Xa has a nucleotide sequence Xa. Xa does not hybridize with Y so that the nucleotide sequence Xa preferably does not contain a sequence that is complementary to the nucleotide sequence Y.

The nucleotide sequence Xa is a base sequence of nucleotides that compose the oligonucleotide Xa.

The number of nucleotides contained in Xa is 1 to 40, preferably 2 to 20, more preferably 3 to 10, further preferably 4 to 8, still more preferably 4 or 5, and particularly preferably 5. The number of nucleotides contained in Xa is normally selected depending on the other factors such as the strength of the antisense effect on the above-mentioned target RNA, stability of the structure hybridized within a molecule thereof, costs, and synthesis yield.

Xb represents a group derived from an oligonucleotide Xb composed of 4 to 40 nucleotides independently selected from the group consisting of deoxyribonucleotides, ribonucleotides and sugar-modified nucleotides, and the deoxyribonucleotides, ribonucleotides and sugar-modified nucleotides are each independently not modified, or modified at least one of a base moiety and phosphate moiety. The oligonucleotide Xb contains at least one sugar-modified nucleotide. The oligonucleotide Xb has a nucleotide sequence Xb and the nucleotide sequence Xb contains a sequence that is complementary to the nucleotide sequence Y.

The nucleotide sequence Xb is a base sequence of nucleotides that compose the oligonucleotide Xb.

The number of nucleotides contained in Xb is 4 to 40, preferably 6 to 25, more preferably 8 to 16, further preferably 9 to 13, and particularly preferably 9 to 11. The number of nucleotides contained in Xb is normally selected depending on the other factors such as the strength of the antisense effect on the above-mentioned target RNA, stability of the structure hybridized within a molecule thereof, costs, and synthesis yield.

The oligonucleotide X is an oligonucleotide in which one end of the above-mentioned oligonucleotide Xa and one end of the above-mentioned oligonucleotide Xb are each coupled through a covalent bond, and the 5'-position of the nucleotide at the 5'-end of Xa and the 3'-position of the nucleotide at the 3'-end of Xb are coupled by forming a phosphodiester bond or a modified phosphodiester bond, or the 5'-position of the nucleotide at the 5'-end of Xb and the 3'-position of the nucleotide at the 3'-end of Xa are coupled by forming a phosphodiester bond or a modified phosphodiester bond.

X is a group derived from an oligonucleotide X composed of 5 to 80 nucleotides independently selected from the group consisting of deoxyribonucleotides, ribonucleotides and sugar-modified nucleotides, and the deoxyribonucleotides, ribonucleotides and sugar-modified nucleotides are each independently not modified, or modified at least one of a base moiety and phosphate moiety. The oligonucleotide X contains at least two sugar-modified nucleotides. The oligonucleotide X has a nucleotide sequence X.

The nucleotide sequence X is a base sequence of nucleotides that compose the oligonucleotide X. The nucleotide sequence X has the same meaning as that of the nucleotide sequence (Xb-Xa).

The number of nucleotides contained in X is 5 to 80, preferably 8 to 45, more preferably 11 to 26, further preferably 13 to 21, and particularly preferably 13 to 16. The number of nucleotides contained in X is normally selected depending on the other factors such as the strength of the antisense effect on the above-mentioned target RNA, stability of the structure hybridized within a molecule thereof, costs, and synthesis yield.

Y is a group derived from an oligonucleotide Y composed of 4 to 40 nucleotides independently selected from the group consisting of deoxyribonucleotides, ribonucleotides and sugar-modified nucleotides, and the deoxyribonucleotides, ribonucleotides and sugar-modified nucleotides are each independently not modified, or modified at least one of a base moiety and phosphate moiety. The oligonucleotide Y contains at least one ribonucleotide. The oligonucleotide Y has a nucleotide sequence Y, and the nucleotide sequence Y contains a sequence complimentary to the nucleotide sequence Xb.

The nucleotide sequence Y is a base sequence of nucleotides that compose an oligonucleotide Y.

The number of nucleotides contained in Y is 4 to 40, preferably 6 to 25, more preferably 8 to 16, and particularly preferably 10 to 13. The number of nucleotides contained in Y may be the same as or different from that of the number of nucleotides contained in Xb. The number of nucleotides contained in Y is normally selected depending on the other factors such as the strength of the antisense effect on the above-mentioned target RNA, stability of the structure hybridized within a molecule thereof, costs, and synthesis yield. The difference between the number of nucleotides contained in Y and the number of nucleotides contained in Xb is preferably within 10, more preferably within 5, further preferably within 4, still more preferably within 2, and particularly preferably 0.

Xz is a group derived from an oligonucleotide Xz composed of 5 to 40 nucleotides independently selected from the group consisting of deoxyribonucleotides, ribonucleotides and sugar-modified nucleotides, and the deoxyribonucleotides, ribonucleotides and sugar-modified nucleotides are each independently not modified, or modified at least one of a base moiety and phosphate moiety. The oligonucleotide Xz contains at least one sugar-modified nucleotide. The oligonucleotide Xz has a nucleotide sequence Xz.

The nucleotide sequence Xz is a base sequence of nucleotides that compose an oligonucleotide Xz.

The number of nucleotides contained in Xz is 5 to 40, preferably 8 to 30, more preferably 11 to 25, further more preferably 12 to 21 bases, and particularly preferably 13 to 14 bases. The number of nucleotides contained in Xz is normally selected depending on the other factors such as the strength of the antisense effect on the above-mentioned target RNA, stability of the structure of the X and Y hybridized within a molecule thereof, costs, and synthesis yield.

Yz is a group derived from an oligonucleotide Yz composed of 5 to 40 nucleotides independently selected from the group consisting of deoxyribonucleotides, ribonucleotides and sugar-modified nucleotides, and the deoxyribonucleotides, ribonucleotides and sugar-modified nucleotides are each independently not modified or at least one of a base moiety and phosphate moiety is modified. The oligonucleotide Yz contains at least one sugar-modified nucleotide. The oligonucleotide Yz has a nucleotide sequence Yz.

The nucleotide sequence Yz is a base sequence of nucleotides that compose an oligonucleotide Yz.

The number of nucleotides contained in Yz is 5 to 40, preferably 8 to 30, more preferably 11 to 25, further more preferably 12 to 21 bases, and particularly preferably 13 to 14 bases. The number of nucleotides contained in Yz is normally selected depending on the other factors such as the strength of the antisense effect on the above-mentioned target RNA, stability of the structure of the X and Y hybridized within a molecule thereof, costs, and synthesis yield.

X and Y are coupled in the order of Xb-Xa-Y. When Xb is bound to Xa at the 3'-side, Y is bound to Xa at the 5'-side. When Xb is bound to Xa at the 5'-side, Y is bound to Xa at the 3'-side.

Xa and Y are coupled through a covalent bond, and the 5'-position of the nucleotide at the 5'-end of Xa and the 3'-position of the nucleotide at the 3'-end of Y are coupled by forming a phosphodiester bond or a modified phosphodiester bond, or the 5'-position of the nucleotide at the 5'-end of Y and the 3'-position of the nucleotide at the 3'-end of Xa are coupled by forming a phosphodiester bond or a modified phosphodiester bond. Xa and Y are preferably coupled through a phosphodiester bond.

Xa may contain or may not contain a partially complementary sequence in the group derived from the oligonucleotide of Xa.

Xb and Y hybridize within a molecule.

Although the nucleotide sequence Xb and the nucleotide sequence Y are not required to be completely complementary in order for Xb and Y to hybridize, complementarity is preferably 70% or more, more preferably 80% or more and even more preferably 90% or more (such as 95%, 96%, 97%, 98%, 99% or more). The nucleotide sequence Xb and the nucleotide sequence Y may also be completely complementary.

Although it is not necessary that the entire of Y hybridize with Xb which is a part of the antisense sequence portion, and a part of Y may not hybridize, but preferably all are hybridized.

When Y partially hybridizes with Xb which is a part of the antisense sequence portion, at least the end at the Xa side in Y is preferably hybridized with Xb. The number of nucleotides which partially hybridize is normally selected depending on the other factors such as stability of the structure hybridized between molecules or within a molecule thereof, the strength of the antisense effect on the above-mentioned target RNA, costs, and synthesis yield.

The nucleotide sequence X contains an antisense sequence. Among the nucleotide sequence X, the ratio occupied by the antisense sequence is preferably 70% or more, further preferably 90% or more, and particularly preferably 100%. The antisense sequence contained in the nucleotide sequence X is a sequence containing "at least four contiguous nucleotides recognized by RNase H when hybridizing with a target RNA" or a sequence which contains a sequence "containing at least one sugar-modified nucleotide and does not contain four contiguous deoxyribonucleotide", and the preferred embodiment and the like are as mentioned in the antisense sequence and the antisense sequence portion.

Xb is a part of the antisense sequence portion contained in X and hybridizes in the molecule, and Xa is a part of the antisense sequence portion contained in X and does not hybridize within a molecule. In the case the antisense sequence portion contained in X is a sequence containing "at least four contiguous nucleotides recognized by RNase H when hybridizing with a target RNA", it is preferable that a part of the "at least four contiguous nucleotides recognized by RNase H when hybridizing with a target RNA" is contained in Xb and hybridizes in the molecule, and a part thereof is contained in Xa and does not hybridize within a molecule. As the other embodiment, all of the "at least four contiguous nucleotides recognized by RNase H when hybridizing with a target RNA" is preferably contained in Xb and hybridizes. In the sugar-modified nucleotide sequence portion bound adjacent to at least one of the 3'-side and the 5'-side of the "at least four contiguous nucleotides recognized by RNase H when hybridizing with a target RNA", it is preferable that the portion contained in Xb hybridizes in the molecule, and the portion contained in Xa does not hybridize within a molecule.

In the oligonucleotide X, the oligonucleotide strand composed of 1 to 10 nucleotides independently selected from the group consisting of deoxyribonucleotides, ribonucleotides and sugar-modified nucleotides may bind or may not bind adjacent to the Xb side of the antisense sequence portion contained in the oligonucleotide X, and preferably it does not bind. In the case it binds, the oligonucleotide strand comprising a nucleotide independently selected from deoxyribonucleotides and ribonucleotides are preferably bound adjacent to the end of the Xb side of the antisense sequence portion. In the case the oligonucleotide strand composed of 1 to 10 nucleotides are bound adjacent to the Xb side of the antisense sequence portion, the Xb side of the antisense sequence portion and the above-mentioned oligonucleotide strand are preferably coupled through a phosphodiester bond.

The nucleotide sequence Xz contains an antisense sequence, and among the nucleotide sequence Xz, a ratio occupied by the antisense sequence is preferably 70% or more, further preferably 90% or more, and particularly preferably 100%. The antisense sequence contained in the nucleotide sequence Xz is a sequence containing "at least four contiguous nucleotides recognized by RNase H when hybridizing with a target RNA" or a sequence containing a sequence "containing at least one sugar-modified nucleotide and does not contain four contiguous deoxyribonucleotide", and the preferred embodiments are those as mentioned in the antisense sequence and the antisense sequence portion.

The antisense sequence portion contained in Xz does not hybridize within a molecule.

In the oligonucleotide Xz, the oligonucleotide strand composed of 1 to 10 nucleotides independently selected from the group consisting of deoxyribonucleotides, ribonucleotides and sugar-modified nucleotides may bind or may not bind adjacent to the terminal at the side to which it does not bind to Lx of the antisense sequence portion contained in the oligonucleotide Xz, and preferably it does not bind. In the case it binds, the oligonucleotide strand comprising a nucleotide independently selected from deoxyribonucleotides and ribonucleotides are preferably bound adjacent to the side to which it does not bind to Lx of the antisense sequence portion contained in Xz. In the case the oligonucleotide strand composed of 1 to 10 nucleotides are bound adjacent to the end of the side to which it does not bind to Lx of the antisense sequence portion, the antisense sequence portion and the above-mentioned oligonucleotide strand are preferably coupled through a phosphodiester bond.

The nucleotide sequence Yz contains an antisense sequence, and among the nucleotide sequence Yz, a ratio occupied by the antisense sequence is preferably 70% or more, further preferably 90% or more, and particularly preferably 100%. The antisense sequence contained in the nucleotide sequence Yz is a sequence containing "at least four contiguous nucleotides recognized by RNase H when hybridizing with a target RNA" or a sequence containing a sequence "containing at least one sugar-modified nucleotide and does not contain four contiguous deoxyribonucleotide", and the preferred embodiments are those as mentioned in the antisense sequence and the antisense sequence portion.

The antisense sequence portion contained in Yz does not hybridize within a molecule.

In the oligonucleotide Yz, the oligonucleotide strand composed of 1 to 10 nucleotides independently selected from the group consisting of deoxyribonucleotides, ribonucleotides and sugar-modified nucleotides may bind or may not bind adjacent to the terminal at the side to which it does not bind to Ly of the antisense sequence portion contained in the oligonucleotide Yz, and preferably it does not bind. In the case it binds, the oligonucleotide strand comprising a nucleotide independently selected from deoxyribonucleotides and ribonucleotides are preferably bound adjacent to the side to which it does not bind to Ly of the antisense sequence portion contained in Yz. In the case the oligonucleotide strand composed of 1 to 10 nucleotides are bound adjacent to at least one of the 3'-side and the 5'-side of the antisense sequence portion, the antisense sequence portion and the above-mentioned oligonucleotide strand are preferably coupled through a phosphodiester bond.

The type, number and modified location of the sugar-modified nucleotides, deoxyribonucleotides and ribonucleotides in the oligonucleotide X may have an effect on the antisense effect and the like demonstrated by the single-stranded oligonucleotide. Although preferable aspects thereof are unable to be unconditionally defined since they differ according to the types, sequences and the like of nucleotides targeted for modification, preferable aspects can be specified by measuring the antisense effects possessed by a single-strand oligonucleotide following modification in the same manner as the above-mentioned antisense sequence portion. Xz and Yz are the same as in the oligonucleotide X.

In the case the oligonucleotides X and Xz hybridize with the same target RNA, the antisense sequences possessed thereby may each be the same or different. The oligonucleotides X and Xz may each separately hybridize with the different target RNA.

In the case the oligonucleotides X and Yz hybridize with the same target RNA, the antisense sequences possessed thereby may each be the same or different. The oligonucleotides X and Yz may each separately hybridize with the different target RNA.

The type, number and modified location of sugar-modified nucleotides, deoxyribonucleotides and ribonucleotides in Y may have an effect on the antisense effect demonstrated by the single-stranded oligonucleotide. Although preferable aspects thereof are unable to be unconditionally defined since they differ according to the types, sequences and the like of nucleotides targeted for modification, preferable aspects can be specified by measuring the antisense effects possessed by a single-strand oligonucleotide following modification in the same manner as in the above-mentioned antisense sequence portion. The nucleotide sequence Y preferably contains "at least four contiguous nucleotides cleaved by RNase H", and preferably contains at least one ribonucleotide from the viewpoint of facilitating the formation of an oligonucleotide containing an antisense sequence portion and demonstrating an antisense effect as a result of Y being degraded by a nuclease such as RNase H within a specific cell. These contiguous nucleotides are more preferably selected independently from ribonucleotides. In addition, these the contiguous nucleotides are further preferably coupled through a phosphodiester bond with each other. These contiguous nucleotides may each be the same or different. In addition, the nucleotide sequence Y preferably contains oligoribonucleotide, and more preferably contains RNA.

The "at least four contiguous nucleotides cleaved by RNase H" more preferably contain 4 to 25 contiguous nucleotides.

Next, the respective embodiments of [A] a case where both of Xz and Lx, and Yz and Ly are not contained, [B] a case where Xz and Lx are not contained, and Yz and Ly are contained and [C] a case where Xz and Lx are contained, and Yz and Ly are not contained are explained in this order.

[A] Case where Both of Xz and Lx, and Yz and Ly are not Contained (m=0, n=0)

The nucleotide sequence Y preferably contains at least four contiguous nucleotides cleaved by RNase H, and more preferably contains 4 to 25 contiguous nucleotides. These contiguous nucleotides each may each be the same or different from each other. Y preferably contains an oligoribonucleotide, and more preferably contains RNA. Among the nucleotides at the 5'-side and the 3'-side of the oligonucleotide Y, at least one of which is preferably phosphorothioated. When Xb bonds to Xa on the 3'-side and Y bonds to Xa on the 5'-side, the 3'-side of the oligonucleotide Y is preferably phosphorothioated. When Xb bonds to Xa on the 5'-side and Y bonds to Xa on the 3'-side, the 5'-side of the oligonucleotide Y is preferably phosphorothioated. When Xb bonds to Xa on the 3'-side and Y bonds to Xa on the 5'-side, the 3'-side of the oligonucleotide Y preferably contains 1 to 10 sugar-modified nucleotides, more preferably contains 2 to 5 sugar-modified nucleotides, and further preferably contains 2 or 3 sugar-modified nucleotides. When Xb bonds to Xa on the 5'-side and Y bonds to Xa on the 3'-side, the 5'-side of the oligonucleotide Y preferably contains 1 to 10 sugar-modified nucleotides, more preferably contains 2 to 5 sugar-modified nucleotides, and further preferably contains 2 or 3 sugar-modified nucleotides. The above-mentioned plurality of the sugar-modified nucleotides are preferably coupled through a phosphorothioate bond. Here, between a plurality of the sugar-modified nucleotides on at least one of the 3'-side and the 5'-side, a plurality of the deoxyribonucleotides or ribonucleotides or both of them may be contained, and the plurality of the sugar-modified nucleotides are preferably contiguous. In the case a plurality of sugar-modified nucleotides are contained in at least one of the 3'-side and the 5'-side of sugar-modified nucleotide the oligonucleotide Y, each sugar-modified nucleotide may each be the same or different.

The sugar-modified nucleotide contained in at least one of the 3'-side and the 5'-side of the oligonucleotide Y is preferably a 2'-O-methyl nucleotide, 2'-MOE (2'-O-methoxyethyl) nucleotide, 2'-AP (2'-O-aminopropyl) nucleotide, 2'-fluoronucleotide, 2'-F-arabinonucleotide (2'-F-ANA), bridged nucleotide (BNA (Bridged Nucleic Acid)) or 2'-O-methylcarbamoylethyl nucleotide (MCE), more preferably BNA or 2'-O-methyl nucleotide, further more preferably LNA containing a partial structure represented by the following formula (II) or 2'-O-methyl nucleotide, and particularly preferably a 2'-O-methyl nucleotide.

[Formula 4]

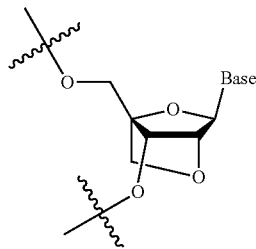

(I)

In the formula, Base represents a base moiety and is a purin-9-yl group or 2-oxo-pyrimidin-1-yl group, and the purin-9-yl group and 2-oxo-pyrimidin-1-yl group may not be modified or may be modified.

As the other embodiment, the nucleotide contained in Y is preferably selected independently from the ribonucleotides. Also, the nucleotides contained in Y are preferably coupled with each other through a phosphodiester bond.

[B] Case where Xz and Lx are not Contained, and Yz and Ly are Contained (m=0, n=1)

The nucleotide sequence Y preferably contains at least four contiguous nucleotides cleaved by RNase H, and more preferably contains 4 to 25 contiguous nucleotides. These contiguous nucleotides each may each be the same or different from each other. The oligonucleotide Y preferably contains an oligoribonucleotide, more preferably contains RNA, and particularly preferably is a group derived from RNA. The nucleotide contained in Y preferably selected independently from the ribonucleotides. The nucleotides contained in Y are preferably coupled to each other through a phosphodiester bond.

[C] Case where Xz and Lx are Contained, and Yz and Ly are not Contained (m=1, n=0)

Preferred embodiment of the nucleotide sequence Y is the same as the above-mentioned [A] case where both of Xz and Lx, and Yz and Ly are not contained.

Next, Lx, Ly and the functional molecule are explained. The following are common in the above-mentioned some embodiments.

Lx is a group derived from an oligonucleotide Lx composed of 0 to 20 nucleotides independently selected from the group consisting of deoxyribonucleotides, ribonucleotides and sugar-modified nucleotides, and is a linker to couple with the above-mentioned Xb and Xz. Lx couples with the above-mentioned Xb and Xz in the order of Xz-Lx-Xb.

When m is 1, and the oligonucleotide Lx comprises 0 nucleotide, Xb and Xz are directly coupled.

Ly represents a group derived from an oligonucleotide Ly composed of 0 to 20 nucleotides that are independently selected from the group consisting of deoxyribonucleotides, ribonucleotides and sugar-modified nucleotides, and is a linker to couple with the above-mentioned Y and Yz. Ly couples with the above-mentioned Y and Yz in the order of Y-Ly-Yz.

When n is 1, and the oligonucleotide Ly comprises 0 nucleotide, Y and Yz are directly coupled.

Lx and Xb are coupled through a covalent bond and, for example, an oxygen atom in which a hydrogen atom is removed from a hydroxyl group of sugar moieties (in the sugar-modified nucleotide, it includes a partial structure replaced with a sugar skeleton) of the terminal nucleotide of Xb is preferably coupled with the sugar moieties of the terminal nucleotide of Lx through a phosphodiester bond or a modified phosphodiester bond. Lx and Xz are preferably coupled through a covalent bond and, for example, an oxygen atom in which a hydrogen atom is removed from a hydroxyl group of sugar moieties (in the sugar-modified nucleotide, it includes a partial structure replaced with a sugar skeleton) of the terminal nucleotide of Xz is preferably coupled with the sugar moieties of the terminal nucleotide of Lx through a phosphodiester bond or a modified phosphodiester bond.

Also, similarly, Ly and Y are preferably coupled at the sugar moieties of the terminal nucleotide of Ly and the sugar moieties of the terminal nucleotide of Y, and Ly and Yz are preferably coupled at the sugar moieties of the terminal nucleotide of Ly and the sugar moieties of the terminal nucleotide of Yz. When Xb and Xz are directly coupled, it is similarly preferable that the sugar moieties of the terminal nucleotide of Xb and the sugar moieties of the terminal nucleotide of Xz are preferably coupled through a phosphodiester bond or a modified phosphodiester bond, and more preferably coupled through a phosphodiester bond. When Y and Yz are directly coupled, it is similarly preferable that the sugar moieties of the terminal nucleotide of Y and the sugar moieties of the terminal nucleotide of Yz are preferably coupled through a phosphodiester bond or a modified phosphodiester bond, and more preferably coupled through a phosphodiester bond. When the above-mentioned terminal nucleotide is a sugar-modified nucleotide, the above-mentioned sugar moieties contains a partial structure replaced with a sugar skeleton.

When Xb is coupled to Xa at the 3'-side, Y is coupled to Xa at the 5'-side. Further, when m is 1, Xb is coupled to Lx at the 5'-side, and Xz is coupled to Lx at the 3'-side. Moreover, when Xb is coupled to Xa at the 3'-side, Y is coupled to Xa at the 5'-side, and further n is 1, Y is coupled to Ly at the 3'-side, and Yz is coupled to Ly at the 5'-side.

When Xb is coupled to Xa at the 5'-side, Y is coupled to Xa at the 3'-side. Further, when m is 1, Xb is coupled to Lx at the 3'-side, and Xz is coupled to Lx at the 5'-side. Moreover, when Xb is coupled to Xa at the 5'-side, Y is coupled to Xa at the 3'-side, and further n is 1, Y is coupled to Ly at the 5'-side, and Yz is coupled to Ly at the 3'-side.

Lx and Ly are desirably decomposed rapidly than the above-mentioned antisense sequence portion.

The above-mentioned oligonucleotide Lx is preferably an oligonucleotide that is degraded under physiological conditions.

The above-mentioned oligonucleotide Ly is preferably an oligonucleotide that is degraded under physiological conditions.

Here, an "oligonucleotide degraded under physiological conditions" may be any oligonucleotide that is degraded by enzymes such as various DNase (deoxyribonuclease) and RNase (ribonuclease) under physiological conditions, and a base moiety, sugar moiety or phosphate bond may or may not be chemically modified in all or a portion of the nucleotides that compose the oligonucleotide.

The above-mentioned oligonucleotide Lx is preferably an oligonucleotide coupled with a phosphodiester bond, more preferably oligodeoxyribonucleotide or oligoribonucleotide, even more preferably DNA or RNA, and still more preferably RNA. The oligonucleotide Ly is the same as the oligonucleotide Lx.

The oligonucleotide Lx may contain or may not contain a partially complementary sequence in the oligonucleotide Lx, and the oligonucleotide Lx is preferably an oligonucleotide which does not contain a partially complementary sequence in the oligonucleotide Lx. Examples of groups derived from such an oligonucleotide include $(N)_k$ (each N independently represents adenosine, uridine, cytidine, guanosine, 2'-deoxyadenosine, thymidine, 2'-deoxycytidine or 2'-deoxyguanosine, and k is an integer of 1 to 20 (a repeating number)) coupled through a phosphodiester bond. Among them, k is preferably 1 to 12, more preferably 1 to 8, further preferably 1 to 5, and further more preferably 1 to 3. The oligonucleotide Ly is the same as the oligonucleotide Lx.

A functional molecule may be bound directly or indirectly to X (including Xa and Xb), Y, Xz, Yz, Lx and Ly. In the above-mentioned [A] case where both of Xz and Lx, and Yz and Ly are not contained, the functional molecule is preferably bound to the oligonucleotide Y. In the above-mentioned [B] case where Xz and Lx are not contained, and Yz and Ly are contained, the functional molecule is preferably bound to the oligonucleotide Xb or the oligonucleotide Y. In the above-mentioned [C] case where Xz and Lx are contained, and Yz and Ly are not contained, the functional molecule is preferably bound to the oligonucleotide Y. The bonding between the functional molecule and the oligonucleotide Y or the oligonucleotide Xb may be bound directly or indirectly through the other substance, and the oligonucleotide Y or the oligonucleotide Xb and a functional molecule are preferably bound through a covalent bond, an ionic bond or a hydrogen bond. From the viewpoint of high bond stability, they are more preferably bound directly through a covalent bond or bound covalently through a linker (a linking group).

In the case the above-mentioned functional molecule is bound to the single-stranded oligonucleotide by a covalent bond, the above-mentioned functional molecule is preferably bound directly or indirectly to the 3'-end or 5'-end of the single-stranded oligonucleotide molecule. Bonding between the above-mentioned linker or a functional molecule and the terminal nucleotide of the single-stranded oligonucleotide molecule is selected according to the functional molecule.

The above-mentioned linker or functional molecule and the terminal nucleotide of the single-stranded oligonucleotide molecule are preferably coupled through a phosphodiester bond or a modified phosphodiester bond, and more preferably coupled through a phosphodiester bond.

The above-mentioned linker or functional molecule may be directly coupled with an oxygen atom at the 3'-position possessed by the nucleotide at the 3'-end of the single-stranded oligonucleotide molecule or an oxygen atom at the 5'-position possessed by the nucleotide at the 5'-end.

There are no particular limitations on the structure of the "functional molecule", and a desired function is imparted to the single-stranded nucleotide as a result of bonding therewith. Examples of desired functions include a labeling function, purifying function and delivery function to a target site. Examples of molecules that impart a labeling function include fluorescent proteins and compounds such as luciferase. Examples of molecules that impart a purifying function include compounds such as biotin, avidin, His-tag peptide, GST-tag peptide or FLAG-tag peptide.

In addition, from the viewpoint of efficiently delivering a single-stranded oligonucleotide to a target site (such as a target cell) with high specificity and extremely effectively suppressing expression of a target gene with the single-stranded oligonucleotide, a molecule having a function that causes the single-stranded oligonucleotide to be delivered to a target site is preferably bound as a functional molecule. The molecules having such a delivery function can be referred to publications such as European Journal of Pharmaceuticals and Biopharmaceutics, Vol. 107, pp. 321-340 (2016), Advanced Drug Delivery Reviews, Vol. 104, pp. 78-92 (2016), and Expert Opinion on Drug Delivery, Vol. 11, pp. 791-822 (2014).

Examples of molecules that impart a delivery function to target RNA include lipids and sugars from the viewpoint of, for example, being able to efficiently deliver a single-stranded oligonucleotide to the liver and the like with high specificity. Examples of such lipids include cholesterol; fatty acids; fat-soluble vitamins such as vitamin E (tocopherols, tocotrienols), vitamin A, vitamin D and vitamin K; intermediate metabolites such as acylcarnitine and acyl CoA; glycolipids; glycerides; and derivatives thereof. Among these, cholesterol and vitamin E (tocopherols, tocotrienols) are preferable from the viewpoint of higher safety. Among these, tocopherols are more preferable, tocopherol is even more preferable, and α-tocopherol is particularly preferable. Examples of sugars include sugar derivatives that interact with asialoglycoprotein receptors.

"Asialoglycoprotein receptors" are present on the surface of liver cells and have an action that recognizes a galactose residue of an asialoglycoprotein and incorporates the molecules into the cell where they are degraded. "Sugar derivatives that interact with asialoglycoprotein receptors" are preferably compounds that have a structure that resembles a galactose residue and are incorporated into cells due to interaction with asialoglycoprotein receptors, and examples thereof include GalNAc (N-acetylgalactosamine) derivatives, galactose derivatives and lactose derivatives. In addition, from the viewpoint of being able to efficiently deliver the single-stranded oligonucleotide of the present invention to the brain with high specificity, examples of the "functional molecules" include sugars (such as glucose and sucrose). In addition, from the viewpoint of being able to efficiently deliver the single-stranded oligonucleotide to various organs with high specificity by interacting with various proteins on the cell surface of those organs, examples of the "functional molecules" include receptor ligands, antibodies, and peptides or proteins of fragments thereof.

Since the linker used to intermediate bonding between a functional molecule and X (including Xa and Xb), Y, Xz, Yz, Lx or Ly is only required to be able to demonstrate the function possessed by the functional molecule as a single-stranded oligonucleotide, there are no particular limitations on the linker provided it stably bonds the functional molecule and the oligonucleotide. Examples of the linker include a group derived from oligonucleotides having a number of the nucleotides of 2 to 20, a group derived from polypeptides having a number of the amino acids of 2 to 20, an alkylene group having 2 to 20 carbon atoms and an alkenylene group having 2 to 20 carbon atoms. The above-mentioned group derived from oligonucleotides having a number of the nucleotides of 2 to 20 is a group in which a hydroxyl group or a hydrogen atom is removed from the oligonucleotides having a number of the nucleotides of 2 to 20. The above-mentioned group derived from polypeptides having a number of the amino acids of 2 to 20 is a group in which a hydroxyl group, a hydrogen atom or an amino group is removed from the polypeptides having a number of the amino acids of 2 to 20.

The linker is preferably a $C_{2-20}$ alkylene group or a $C_{2-20}$ alkenylene group (methylene groups contained in the alkylene group and the alkenylene group are each independently unsubstituted or substituted with one or two substituents selected from the group consisting of a halogen atom, a hydroxyl group, a protected hydroxyl group, an oxo group and a thioxo group. In addition, the methylene groups of the alkylene group and the alkenylene group are each independently are not replaced, or replaced with —O—, —NR$^B$— (R$^B$ represents a hydrogen atom, a $C_{1-6}$ alkyl group or a halo-$C_{1-6}$ alkyl group), —S—, —S(=O)— or —S(=O)$_2$—). Here, by combining the above-mentioned substitutions and replacements, the linker may also contain a group represented by —C(=O)—O—, —O—C(=O)—NR$^1$— (R$^1$ represents a hydrogen atom, a $C_{1-6}$ alkyl group or a halo-$C_{1-6}$ alkyl group), —C(=O)—NR$^1$— (R$^1$ represents a hydrogen atom, a $C_{1-6}$ alkyl group or a halo-$C_{1-6}$ alkyl group), —C(=S)—NR$^1$— (R$^1$ represents a hydrogen atom, a $C_{1-6}$ alkyl group or a halo-$C_{1-6}$ alkyl group) or —NR$^1$—C(=O)—NR$^1$— (R$^1$ each independently represents a hydrogen atom, a $C_{1-6}$ alkyl group or a halo-$C_{1-6}$ alkyl group).

The linker is more preferably a $C_{2-20}$ alkylene group (methylene groups of the alkylene group are each independently not replaced, or replaced with —O—. The methylene groups not replaced are each independently unsubstituted, or substituted by a hydroxyl group or a protected hydroxyl group), further preferably a $C_{8-12}$ alkylene group (methylene groups of the alkylene group are each independently not replaced, or replaced with —O—. The methylene groups not replaced are each independently unsubstituted, or substituted by a hydroxyl group), and particularly preferably a 1,8-octylene group. In addition, as another aspect thereof, the linker is particularly preferably a group represented by the following formula (III).

[Formula 5]

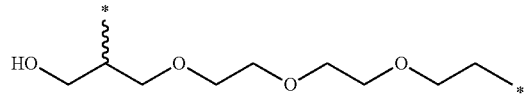

(III)

In the formula, one asterisk (*) represents a bonding site (an atom that composes a nucleotide) with a group derived from an oligonucleotide, while the other asterisk (*) represents a bonding site (an atom that composes a group derived from a functional molecule) with a group derived from a functional molecule.

As another aspect thereof, the linker is more preferably a $C_{2-20}$ alkylene group (methylene groups of the alkylene group are each independently not replaced, or replaced with —O— or —NR$^B$— (R$^B$ is a hydrogen atom or a $C_{1-6}$ alkyl group). The methylene groups not replaced are each independently unsubstituted, or substituted by an oxo group), and further preferably a group represented by the following formula:

[Formula 6]

—N(H)C(=O)—(CH$_2$)$_e$—N(H)C(=O)—(CH$_2$)$_e$—C(=O)—     [Formula 6]

(wherein, e each independently represents an integer of 1 to 6), and particularly preferably a group represented by the following formula:

[Formula 7]

—N(H)C(=O)—(CH$_2$)$_e$—N(H)C(=O)—(CH$_2$)$_e$—C(=O)—     [Formula 7]

A protective group of the above-mentioned "protected hydroxyl group" is not particularly limited since it may be stable at the time of bonding the functional molecule and the oligonucleotide. The linker is not particularly limited and may be mentioned an optional protective group described in, for example, PROTECTIVE GROUPS IN ORGANIC SYNTHESIS, 3$^{rd}$ Edition, published by JOHN WILLY & SONS (1999) and the like. Specifically, there may be mentioned a methyl group, a benzyl group, a p-methoxybenzyl group, a tert-butyl group, a methoxymethyl group, a methoxyethyl group, a 2-tetrahydropyranyl group, an ethoxyethyl group, a cyanoethyl group, a cyanoethoxymethyl group, a phenylcarbamoyl group, a 1,1-dioxothiomorpholin-4-thiocarbamoyl group, an acetyl group, a pivaloyl group, a benzoyl group, a trimethylsilyl group, a triethylsilyl group, a triisopropylsilyl group, a tert-butyldimethylsilyl group, a [(triisopropylsilyl)oxy]methyl group (Tom group), a 1-(4-chlorophenyl)-4-ethoxypiperidin-4-yl group (Cpep group), a triphenylmethyl group (trityl group), a monomethoxytrityl group, a dimethoxytrityl group (DMTr group), a trimethoxytrityl group, a 9-phenylxanthen-9-yl group (Pixyl group), a 9-(p-methoxyphenyl)xanthen-9-yl group (MOX group) and the like. A protective group of the "protected hydroxyl group" is preferably a benzoyl group, a trimethylsilyl group, a triethylsilyl group, a triisopropylsilyl group, a tert-butyldimethylsilyl group, a triphenylmethyl group, a monomethoxytrityl group, a dimethoxytrityl group, a trimethoxytrityl group, a 9-phenylxanthen-9-yl group or a 9-(p-methoxyphenyl)xanthen-9-yl group, more preferably a monomethoxytrityl group, a dimethoxytrityl group or a trimethoxytrityl group, and further more preferably a dimethoxytrityl group.

The following lists examples of preferable single-stranded oligonucleotides used in nucleic acid pharmaceuticals.
1) A single-stranded oligonucleotide represented by the formula (I)

[Formula 8]

$$[Xz\text{-}Lx]_m\text{-}X\text{-}Y\text{-}[Ly\text{-}Yz]_n \quad (I)$$

{wherein,

Y represents a group derived from an oligonucleotide Y composed of 4 to 40 nucleotides containing at least one ribonucleotide that are independently selected from the group consisting of deoxyribonucleotides, ribonucleotides and sugar-modified nucleotides, X represents a group derived from an oligonucleotide X composed of 5 to 80 nucleotides represented by the formula:

[Formula 9]

$$Xb\text{-}Xa$$

(wherein, Xb represents a group derived from an oligonucleotide Xb composed of 4 to 40 nucleotides containing at least one sugar-modified nucleotides that are independently selected from the group consisting of deoxyribonucleotides, ribonucleotides and sugar-modified nucleotides, Xa represents a group derived from an oligonucleotide Xa composed of 1 to 40 nucleotides containing at least one sugar-modified nucleotides that are independently selected from the group consisting of deoxyribonucleotides, ribonucleotides and sugar-modified nucleotides, and Xa is respectively bonded with the oligonucleotide Y and the oligonucleotide Xb at both ends thereof), Xz represents a group derived from an oligonucleotide Xz composed of 5 to 40 nucleotides containing at least one sugar-modified nucleotides that are independently selected from the group consisting of deoxyribonucleotides, ribonucleotides and sugar-modified nucleotides, Yz represents a group derived from an oligonucleotide Yz composed of 5 to 40 nucleotides containing at least one sugar-modified nucleotides that are independently selected from the group consisting of deoxyribonucleotides, ribonucleotides and sugar-modified nucleotides, Lx represents a group derived from an oligonucleotide Lx composed of 0 to 20 nucleotides that are independently selected from the group consisting of deoxyribonucleotides, ribonucleotides and sugar-modified nucleotides, Ly represents a group derived from an oligonucleotide Ly composed of 0 to 20 nucleotides that are independently selected from the group consisting of deoxyribonucleotides, ribonucleotides and sugar-modified nucleotides, m represents 0 or 1, when m represents 0, n represents 0 or 1, when m represents 1, n represents 0, the oligonucleotide X has a nucleotide sequence X, the oligonucleotide Xa has a nucleotide sequence Xa, the oligonucleotide Xb has a nucleotide sequence Xb, the oligonucleotide Y has a nucleotide sequence Y, the oligonucleotide Xz has a nucleotide sequence Xz, the oligonucleotide Yz has a nucleotide sequence Yz, the oligonucleotide Lx has a nucleotide sequence Lx, and the oligonucleotide Ly has a nucleotide sequence Ly, the nucleotide sequence Xb is complementary to the nucleotide sequence Y, the nucleotide sequence X contains an antisense sequence that is capable of hybridizing with a target RNA, when m represents 1 and n represents 0, the nucleotide sequence Xz contains an antisense sequence that is capable of hybridizing with a target RNA, when m represents 0 and n represents 1, the nucleotide sequence Yz contains an antisense sequence that is capable of hybridizing with a target RNA, and in the case of having two or more antisense sequences, the target RNA hybridized by each antisense sequence portion may each be the same or different} and Xb and Y hybridize.

2) The single-stranded oligonucleotide described in 1), wherein Xb bonds to Xa on the 3'-side and Y bonds to Xa on the 5'-side.

3) The single-stranded oligonucleotide described in 1), wherein Xb bonds to Xa on the 5'-side and Y bonds to Xa on the 3'-side.

4) The single-stranded oligonucleotide described in any one of 1) to 3), wherein complementarity of the antisense sequence and the sequence of the target RNA is 70% or more.

5) The single-stranded oligonucleotide described in any one of 1) to 4), wherein complementarity of the nucleotide sequence Xb and the nucleotide sequence Y is 70% or more.

6) The single-stranded oligonucleotide described in any one of 1) to 5), wherein each nucleotide contained in the single-stranded oligonucleotide represented by the formula (I) is mutually coupled through at least one kind each independently selected from the group consisting of a phosphodiester bond, phosphorothioate bond, methylphosphonate bond, methylthiophosphonate bond, phosphorodithioate bond and phosphoroamidate bond.

7) The single-stranded oligonucleotide described in any one of 1) to 6), wherein each nucleotide contained in the single-stranded oligonucleotide represented by the formula (I) is mutually coupled through at least one kind each independently selected from a phosphodiester bond and a phosphorothioate bond.

8) The single-stranded oligonucleotide described in any one of 1) to 7), wherein the antisense sequence portion contained in X contains a phosphorothioate bond.

9) The single-stranded oligonucleotide described in any one of 1) to 8), wherein the antisense sequence contained in the nucleotide sequence X is a sequence containing nucleotides mutually coupled through a phosphorothioate bond.

10) The single-stranded oligonucleotide described in any one of 1) to 9), wherein the nucleotides contained in the oligonucleotide X are mutually coupled through a phosphorothioate bond.

11) The single-stranded oligonucleotide described in any one of 1) to 10), wherein at least one of the nucleotide at the 3'-side and the nucleotide at the 5'-side of the antisense sequence portion contained in the oligonucleotide X is a sugar-modified nucleotide.

12) The single-stranded oligonucleotide described in any one of 1) to 11), wherein the 3'-side nucleotide and the 5'-side nucleotide at the antisense sequence portion contained in the oligonucleotide X are sugar-modified nucleotides.

13) The single-stranded oligonucleotide described in any one of 1) to 12), wherein the antisense sequence contained in the above-mentioned nucleotide sequence X is a sequence composed of 11 to 26 nucleotides independently selected from sugar-modified nucleotides and deoxyribonucleotides.

14) The single-stranded oligonucleotide described in any one of 1) to 13), wherein the antisense sequence contained in the above-mentioned nucleotide sequence X is a sequence composed of 11 to 26 nucleotides containing at least one deoxyribonucleotide.

15) The single-stranded oligonucleotide described in any one of 1) to 14), wherein the antisense sequence contained in the above-mentioned nucleotide sequence X is a sequence containing at least four contiguous nucleotides recognized by RNase H when hybridized with the target RNA.

16) The single-stranded oligonucleotide described in 15), wherein the above-mentioned antisense sequence portion contains a sugar-modified nucleotide bound adjacent to the 5'-side and the 3'-side of the "sequence portion containing the above-mentioned at least four contiguous nucleotides recognized by RNase H".

17) The single-stranded oligonucleotide described in any one of 15) or 16), wherein the above-mentioned "sequence containing at least four contiguous nucleotides recognized by RNase H when hybridized with the target RNA" is a sequence composed of 4 to 20 nucleotides containing at least one deoxyribonucleotide.

18) The single-stranded oligonucleotide described in any one of 1) to 14), wherein the antisense sequence portion contained in the above-mentioned nucleotide sequence X contains at least one sugar-modified nucleotide and does not contain four contiguous deoxyribonucleotides.

19) The single-stranded oligonucleotide described in any one of 1) to 13), wherein the antisense sequence contained in the above-mentioned nucleotide sequence X is a sequence composed of 4 to 30 sugar-modified nucleotides.

20) The single-stranded oligonucleotide described in any one of 1) to 19), wherein the nucleotide sequence Y is a sequence containing at least four contiguous nucleotides cleaved by RNase H.

21) The single-stranded oligonucleotide described in any one of 1) to 20), wherein the nucleotide sequence Y is a sequence composed of 6 to 25 ribonucleotides.

22) The single-stranded oligonucleotide described in any one of 1) to 21), wherein the oligonucleotide Y contains one or more sugar-modified nucleotides on at least one of the 5'-side and the 3'-side of the oligonucleotide Y.

23) The single-stranded oligonucleotide described in any one of 1) to 22), wherein the oligonucleotide Y contains a phosphodiester bond.

24) The single-stranded oligonucleotide described in any one of 1) to 23), wherein at least one of the 5'-side and the 3'-side of Y is coupled with an adjacent nucleotide through a phosphodiester bond.

25) The single-stranded oligonucleotide described in any one of 1) to 24), wherein the oligonucleotide Xa is composed of 3 to 10 nucleotides independently selected from the group consisting of deoxyribonucleotide and sugar-modified nucleotide, and the oligonucleotide Xb is composed of 8 to 16 nucleotides independently selected from the group consisting of deoxyribonucleotide and sugar-modified nucleotide.

26) The single-stranded oligonucleotide described in any one of 1) to 25), wherein m is 0 and n is 0.

27) The single-stranded oligonucleotide described in 26), wherein among the nucleotides on the 5'-side and the 3'-side of Y, at least one of which is phosphorothioated.

28) The single-stranded oligonucleotide described in any one of 1) to 25), wherein m is 1 and n is 0.

29) The single-stranded oligonucleotide described in 28), wherein the antisense sequence portion contained in Xz contains a phosphorothioate bond.

30) The single-stranded oligonucleotide described in 28) or 29), wherein the antisense sequence contained in the nucleotide sequence Xz is a sequence containing nucleotides coupled through a phosphorothioate bond.

31) The single-stranded oligonucleotide described in any one of 28) to 30), wherein the nucleotides contained in the oligonucleotide Xz are mutually coupled through a phosphorothioate bond.

32) The single-stranded oligonucleotide described in any one of 28) to 31), wherein at least one of the nucleotide at the 3'-side and the nucleotide at the 5'-side of the antisense sequence portion contained in the oligonucleotide Xz is a sugar-modified nucleotide.

33) The single-stranded oligonucleotide described in any one of 28) to 32), wherein the nucleotide at the 3'-side and the nucleotide at the 5'-side of the antisense sequence portion contained in the oligonucleotide Xz are sugar-modified nucleotides.

34) The single-stranded oligonucleotide described in any one of 33) to 34), wherein the antisense sequence contained in the above-mentioned nucleotide sequence Xz is a sequence composed of 11 to 26 nucleotides independently selected from sugar-modified nucleotides and deoxyribonucleotides.

35) The single-stranded oligonucleotide described in any one of 28) to 34), wherein the antisense sequence contained in the above-mentioned nucleotide sequence Xz is a sequence composed of 11 to 26 nucleotides containing at least one deoxyribonucleotide.

36) The single-stranded oligonucleotide described in any one of 28) to 35), wherein the antisense sequence contained in the above-mentioned nucleotide sequence Xz is a sequence at least four contiguous nucleotides recognized by RNase H when hybridized with the target RNA.

37) The single-stranded oligonucleotide described in 36), wherein the above-mentioned antisense sequence portion contains sugar-modified nucleotides bound adjacent to the 5'-side and the 3'-side of "the above-mentioned sequence portion containing at least four contiguous nucleotides recognized by RNase H".

38) The single-stranded oligonucleotide described in 36) or 37), wherein the above-mentioned "sequence containing at least four contiguous nucleotides recognized by RNase H when hybridized with the target RNA" is a sequence composed of 4 to 20 nucleotides containing at least one deoxyribonucleotide.

39) The single-stranded oligonucleotide described in any one of 28) to 35), wherein the antisense sequence portion contained in the above-mentioned nucleotide sequence Xz contains at least one sugar-modified nucleotide and does not contain four contiguous deoxyribonucleotides.

40) The single-stranded oligonucleotide described in any one of 28) to 34), wherein the antisense sequence contained in the above-mentioned nucleotide sequence Xz is a sequence composed of 4 to 30 sugar-modified nucleotides.

41) The single-stranded oligonucleotide described in any one of 28) to 40), wherein the oligonucleotide Lx is composed of 0 nucleotide, and Xb and Xz are coupled through a phosphodiester bond.

42) The single-stranded oligonucleotide described in any one of 28) to 40), wherein Lx is a group derived from an oligonucleotide Lx composed of 1 to 20 nucleotides independently selected from the group consisting of deoxyribonucleotides, ribonucleotides and sugar-modified nucleotides.

43) The single-stranded oligonucleotide described in 42), wherein the oligonucleotide Lx contains a phosphodiester bond.

44) The single-stranded oligonucleotide described in any one of 42) or 43), wherein the nucleotides contained in the oligonucleotide Lx are mutually coupled through a phosphodiester bond.

45) The single-stranded oligonucleotide described in any one of 42) to 44), wherein the oligonucleotide Lx is composed of 1 to 8 nucleotides independently selected from the group consisting of deoxyribonucleotides and ribonucleotides.

46) The single-stranded oligonucleotide described in any one of 42) to 45), wherein the oligonucleotide Lx is an oligodeoxyribonucleotide or oligoribonucleotide.

47) The single-stranded oligonucleotide described in any one of 42) to 46), wherein the oligonucleotide Lx is DNA or RNA.

48) The single-stranded oligonucleotide described in any one of 42) to 46), wherein the oligonucleotide Lx is RNA.

49) The single-stranded oligonucleotide described in any one of 28) to 48), wherein among the nucleotides at the 5'-side and the 3'-side of the oligonucleotide Y, at least one of which is phosphorothioated.

50) The single-stranded oligonucleotide described in any one of 1) to 25), wherein m is 0, n is 1.

51) The single-stranded oligonucleotide described in 50), wherein the antisense sequence portion contained in Yz contains a phosphorothioate bond.

52) The single-stranded oligonucleotide described in 50) or 51), wherein the antisense sequence contained in the nucleotide sequence Yz is a sequence containing mutually coupled nucleotides through a phosphorothioate bond.

53) The single-stranded oligonucleotide described in any one of 50) to 52), wherein the nucleotides contained in the oligonucleotide Yz are mutually coupled through a phosphorothioate bond.

54) The single-stranded oligonucleotide described in any one of 50) to 53), wherein at least one of the nucleotide at the 3'-side and the nucleotide at the 5'-side of the antisense sequence portion contained in the oligonucleotide Yz is a sugar-modified nucleotide.

55) The single-stranded oligonucleotide described in any one of 50) to 54), wherein the nucleotide at the 3'-side and the nucleotide at the 5'-side of the antisense sequence portion contained in the oligonucleotide Yz are sugar-modified nucleotides.

56) The single-stranded oligonucleotide described in any one of 50) to 55), wherein the antisense sequence contained in the nucleotide sequence Yz is a sequence composed of 11 to 26 nucleotides independently selected from sugar-modified nucleotides and deoxyribonucleotides.

57) The single-stranded oligonucleotide described in any one of 50) to 56), wherein the antisense sequence contained in the nucleotide sequence Yz is a sequence composed of 11 to 26 nucleotides containing at least one deoxyribonucleotide.

58) The single-stranded oligonucleotide described in any one of 50) to 57), wherein the antisense sequence contained in the nucleotide sequence Yz is a sequence containing at least four contiguous nucleotides recognized by RNase H when hybridized with the target RNA.

59) The single-stranded oligonucleotide described in 58), wherein the antisense sequence portion contains a sugar-modified nucleotide bound adjacent to the 5'-side and the 3'-side of the above-mentioned "sequence portion containing at least four contiguous nucleotides recognized by RNase H".

60) The single-stranded oligonucleotide described in 58) or 59), wherein the "sequence containing at least four contiguous nucleotides recognized by RNase H when hybridized with the target RNA" is a sequence composed of 4 to 20 nucleotides containing at least one deoxyribonucleotide.

61) The single-stranded oligonucleotide described in any one of 50) to 57), wherein the antisense sequence portion contained in the above-mentioned nucleotide sequence Yz contains at least one sugar-modified nucleotide and does not contain four contiguous deoxyribonucleotides.

62) The single-stranded oligonucleotide described in any one of 50) to 56), wherein the antisense sequence contained in the above-mentioned nucleotide sequence Yz is a sequence composed of 4 to 30 sugar-modified nucleotides.

63) The single-stranded oligonucleotide described in any one of 50) to 62), wherein the oligonucleotide Ly is composed of 0 nucleotide, and Y and Yz are coupled through a phosphodiester bond.

64) The single-stranded oligonucleotide described in any one of 50) to 62), wherein Ly is a group derived from an oligonucleotide Ly composed of 1 to 20 nucleotides independently selected from the group consisting of deoxyribonucleotides, ribonucleotides and sugar-modified nucleotides.

65) The single-stranded oligonucleotide described in 64), wherein the oligonucleotide Ly contains a phosphodiester bond.

66) The single-stranded oligonucleotide described in 64) or 65), wherein the nucleotides contained in the oligonucleotide Ly are mutually coupled through a phosphodiester bond.

67) The single-stranded oligonucleotide described in any one of 64) to 66), wherein the oligonucleotide Ly is composed of 1 to 8 nucleotides independently selected from the group consisting of deoxyribonucleotides and ribonucleotides.

68) The single-stranded oligonucleotide described in any one of 64) to 67), wherein the oligonucleotide Ly is an oligodeoxyribonucleotide or oligoribonucleotide.

69) The single-stranded oligonucleotide described in any one of 64) to 68), wherein the oligonucleotide Ly is DNA or RNA.

70) The single-stranded oligonucleotide described in any one of 64) to 69), wherein the oligonucleotide Ly is RNA.

71) The single-stranded oligonucleotide described in any one of 1) to 70), wherein the sugar-modified nucleotide each independently represents a 2'-O-methyl nucleotide, 2'-O-methoxyethyl nucleotide, 2'-O-aminopropyl nucleotide, 2'-fluoronucleotide, 2'-F-arabinonucleotide, bridged nucleotide or 2'-O-methylcarbamoylethyl nucleotide.

72) The single-stranded oligonucleotide described in any one of 1) to 71), wherein the sugar-modified nucleotide each independently represents a 2'-O-methyl nucleotide or LNA.

73) The single-stranded oligonucleotide described in any one of 1) to 72), which further contains a group derived from a functional molecule having at least one function selected from the group consisting of a labeling function, a purifying function or delivery function to a target RNA.

74) The single-stranded oligonucleotide described in 73), wherein the above-mentioned group derived from a functional molecule is directly or indirectly bound to the nucleotide at the 5'-end of the single-stranded oligonucleotide represented by the formula (I).

75) The single-stranded oligonucleotide described in 73), wherein the above-mentioned group derived from a functional molecule is directly or indirectly bound to the nucleotide at the 3'-end of the single-stranded oligonucleotide represented by the formula (I).

76) The single-stranded oligonucleotide described in any one of 73) to 75), wherein the above-mentioned group derived from a functional molecule is bound to the single-stranded oligonucleotide represented by the formula (I) through a $C_{2-20}$ alkylene group or a $C_{2-20}$ alkenylene group (the methylene groups contained in the alkylene group and the alkenylene group are each independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are each independently not replaced, or replaced with —O—, —$NR^B$— ($R^B$ represents a hydrogen atom, a $C_{1-6}$ alkyl group or a halo-$C_{1-6}$ alkyl group), —S—, —S(=O)— or —S(=O)$_2$—), or by a covalent bond directly.

77) The single-stranded oligonucleotide described in any one of 73) to 75), wherein the $C_{2-20}$ alkylene group or the $C_{2-20}$ alkenylene group coupled to the above-mentioned group derived from a functional molecule and the nucleotide at the 5'-end or 3'-end of the single-stranded oligonucleotide represented by the formula (I) are coupled through a phosphodiester bond or a modified phosphodiester bond.

78) The single-stranded oligonucleotide described in any one of 73) to 75), wherein the $C_{2-20}$ alkylene group or the $C_{2-20}$ alkenylene group coupled to the above-mentioned group derived from a functional molecule and the nucleotide at the 5'-end or 3'-end of the single-stranded oligonucleotide represented by the formula (I) are coupled through a phosphodiester bond.

79) The single-stranded oligonucleotide described in any one of 73) to 78), wherein the above-mentioned functional molecule is selected from the group consisting of sugars, lipids, peptides, proteins and derivatives thereof.

80) The single-stranded oligonucleotide described in any one of 73) to 79), wherein the above-mentioned functional molecule is a lipid selected from the group consisting of cholesterol, fatty acids, fat-soluble vitamins, glycolipids and glycerides.

81) The single-stranded oligonucleotide described in any one of 73) to 80), wherein the above-mentioned functional molecule is a lipid selected from the group consisting of cholesterol, tocopherol and tocotrienol.

82) The single-stranded oligonucleotide described in any one of 73) to 75), wherein the above-mentioned functional molecule is a tocopherol, and the hydroxyl group of the tocopherol is bound to the nucleotide at the 5'-end or 3'-end of the single-stranded oligonucleotide represented by the formula (I) through a $C_{2-20}$ alkylene group (the methylene groups of the alkylene group are each independently not replaced, or replaced with —O—. The methylene groups not replaced are each independently unsubstituted or substituted by a hydroxyl group).

83) The single-stranded oligonucleotide described in any one of 73) to 75), wherein the hydroxyl group of the tocopherol is coupled with the nucleotide at the 5'-end or 3'-end of the single-stranded oligonucleotide represented by the formula (I) through a group represented by the following formula (III)

[Formula 10]

(III)

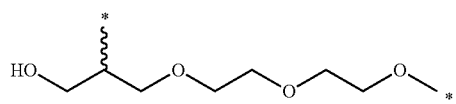

(wherein, one asterisk (*) represents a bonding site (an atom that composes a nucleotide) with a group derived from an oligonucleotide, while the other asterisk (*) represents a bonding site (an atom that composes a group derived from a functional molecule) with a group derived from a functional molecule).

84) The single-stranded oligonucleotide described in any one of 73) to 79), wherein the above-mentioned functional molecule is a sugar derivative that interacts with an asialoglycoprotein receptor.

85) The single-stranded oligonucleotide described in any one of 73) to 79), wherein the above-mentioned functional molecule is a peptide or protein selected from the group consisting of receptor ligands and antibodies.

B-1) The single-stranded oligonucleotide described in 1), wherein it is represented by the formula:

[Formula 11]

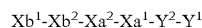

(wherein, $Xb^1$ represents a group derived from an oligonucleotide $Xb^1$ that is composed of 2 or 3 sugar-modified nucleotides, $Xb^2$ represents a group derived from an oligonucleotide $Xb^2$ that is composed of 6 to 8 deoxyribonucleotides, $Xa^2$ represents a group derived from an oligonucleotide $Xa^2$ that is composed of 1 to 3 deoxyribonucleotides, $Xa^1$ represents a group derived from an oligonucleotide $Xa^1$ that is composed of 2 or 3 sugar-modified nucleotides, $Y^2$ represents a group derived from an oligonucleotide $Y^2$ that is composed of 6 to 8 ribonucleotides, and $Y^1$ represents a group derived from an oligonucleotide $Y^1$ that is composed of 2 or 3 sugar-modified nucleotides.

B-2) The single-stranded oligonucleotide described in 73), wherein it is represented by the formula

[Formula 12]

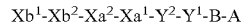

(wherein, $Xb^1$ represents a group derived from an oligonucleotide that is composed of 2 or 3 sugar-modified nucleotides, $Xb^2$ represents a group derived from an oligonucleotide that is composed of 6 to 8 deoxyribonucleotides, $Xa^2$ represents a group derived from an oligonucleotide $Xa^2$ that is composed of 1 to 3 deoxyribonucleotides, $Xa^1$ represents a group derived from an oligonucleotide that is composed of 2 or 3 sugar-modified nucleotides, $Y^2$ represents a group derived from an oligonucleotide that is composed of 6 to 8 ribonucleotides, $Y^1$ represents a group derived from an oligonucleotide that is composed of 2 or 3 sugar-modified nucleotides, B represents a $C_{2-20}$ alkylene group or a $C_{2-20}$ alkenylene group (the methylene groups contained in the alkylene group and the alkenylene group are each independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are each independently not replaced, or replaced with —O—, —$NR^B$— ($R^B$ represents a hydrogen atom, a $C_{1-6}$ alkyl group or a halo-$C_{1-6}$ alkyl group), —S—, —S(O)— or —S(O)$_2$—), and A represents a group derived from a functional molecule).

B-3) The single-stranded oligonucleotide described in B-2), wherein B represents a $C_{2-20}$ alkylene group (the methylene groups of the alkylene group are each independently not replaced, or replaced with —O—. The methylene groups not replaced are each independently unsubstituted, or substituted with a hydroxyl group), and A represents a group derived from tocopherol.

B-4) The single-stranded oligonucleotide described in B-2) or B-3), wherein B is coupled with the terminal nucleotide of $Y^1$ through a phosphodiester bond.

B-5) The single-stranded oligonucleotide described in any one of B-1) to B-4), wherein $Xa^2$ represents a group derived from an oligonucleotide $Xa^2$ composed of 2 or 3 deoxyribonucleotides.

B-6) The single-stranded oligonucleotide described in any one of B-1) to B-5), wherein the sugar-modified nucleotides are each independently selected from the group consisting of LNA, 2'-O-methyl nucleotides, 2'-O-methoxyethyl nucleotides and 2'-O-methylcarbamoylethyl nucleotides.

B-7) The single-stranded oligonucleotide described in any one of B-1) to B-6), wherein the sugar-modified nucleotides contained in $Xb^1$ and $Xa^2$ are LNA.

B-8) The single-stranded oligonucleotide described in any one of B-1) to B-7), wherein the sugar-modified nucleotide contained in $Y^1$ is 2'-O-methyl nucleotide.

B-9) The single-stranded oligonucleotide described in any one of B-1) to B-8), wherein the nucleotides contained in $Xb^1$, $Xb^2$, $Xa^1$, $Xa^2$ and $Y^1$ are mutually coupled through a phosphorothioate bond, and the nucleotides contained in $Y^2$ are mutually coupled through a phosphodiester bond.

B-10) The single-stranded oligonucleotide described in any one of B-1) to B-9), wherein the respective terminal nucleotides of $Xb^1$ and $Xb^2$, $Xb^2$ and $Xa^1$, $Xa^1$ and $Xa^2$, and $Y^2$ and $Y^1$ are coupled through a phosphorothioate bond, and the respective terminal nucleotides of $Xa^2$ and $Y^2$ are coupled through a phosphodiester bond.

In the above-mentioned B-1) to B-10), the oligonucleotide Xb is represented by $Xb^1$-$Xb^2$, the oligonucleotide Xa is represented by $Xa^2$-$Xa^1$, and the oligonucleotide Y is represented by $Y^2$-$Y^1$.

B-11) The single-stranded oligonucleotide described in 1), it is represented by the formula

[Formula 13]

$$Xb^1\text{-}Xb^2\text{-}Xa\text{-}Y^2\text{-}Y^1$$

(wherein, $Xb^1$ represents a group derived from an oligonucleotide $Xb^1$ composed of 4 or 5 sugar-modified nucleotides, $Xb^2$ represents a group derived from an oligonucleotide $Xb^2$ composed of 8 to 10 deoxyribonucleotides, Xa is composed of 4 or 5 sugar-modified nucleotides, $Y^2$ represents a group derived from an oligonucleotide $Y^2$ composed of 8 to 10 ribonucleotides, $Y^1$ represents a group derived from an oligonucleotide $Y^1$ composed of 4 or 5 sugar-modified nucleotides).

B-12) The single-stranded oligonucleotide described in 73), it is represented by the formula

[Formula 14]

$$Xb^1\text{-}Xb^2\text{-}Xa\text{-}Y^2\text{-}Y^1\text{-}B\text{-}A$$

(wherein, $Xb^1$ represents a group derived from an oligonucleotide $Xb^1$ that is composed of 4 or 5 sugar-modified nucleotides, $Xb^2$ represents a group derived from an oligonucleotide $Xb^2$ that is composed of 8 to 10 deoxyribonucleotides, Xa is composed of 4 or 5 sugar-modified nucleotides, $Y^2$ represents a group derived from an oligonucleotide $Y^2$ that is composed of 8 to 10 ribonucleotides, $Y^1$ represents a group derived from an oligonucleotide $Y^1$ that is composed of 4 or 5 sugar-modified nucleotides.

B represents a $C_{2\text{-}20}$ alkylene group or a $C_{2\text{-}20}$ alkenylene group (the methylene groups contained in the alkylene group and the alkenylene group are each independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are each independently not replaced, or replaced with —O—, —$NR^B$— ($R^B$ represents a hydrogen atom, a $C_{1\text{-}6}$ alkyl group or a halo-$C_{1\text{-}6}$ alkyl group), —S—, —S(O)— or —S(O)$_2$—), and A represents a group derived from a functional molecule).

B-13) The single-stranded oligonucleotide described in B-12), wherein B represents a $C_{2\text{-}20}$ alkylene group (the methylene groups of the alkylene group are each independently not replaced, or replaced with —O—. The methylene groups not replaced are each independently unsubstituted, or substituted with a hydroxyl group), and A represents a group derived from tocopherol.

B-14) The single-stranded oligonucleotide described in B-12) or B-13), wherein B is coupled with $Y^1$ the terminal nucleotide through a phosphodiester bond.

B-15) The single-stranded oligonucleotide described in any one of B-11) to B-14), wherein the sugar-modified nucleotides are each independently selected from the group consisting of LNA, 2'-O-methyl nucleotides, 2'-O-methoxyethyl nucleotides and 2'-O-methylcarbamoylethyl nucleotides.

B-16) The single-stranded oligonucleotide described in any one of B-11) to B-15), wherein the sugar-modified nucleotides contained in $Xb^1$ and Xa are each independently LNA or 2'-O-methoxyethyl nucleotide.

B-17) The single-stranded oligonucleotide described in any one of B-11) to B-16), wherein the sugar-modified nucleotides contained in $Y^1$ are 2'-O-methyl nucleotide.

B-18) The single-stranded oligonucleotide described in any one of B-11) to B-17), wherein the nucleotides contained in $Xb^1$, $Xb^2$, Xa and $Y^1$ are mutually coupled through a phosphorothioate bond, and the nucleotides contained in $Y^2$ are mutually coupled through a phosphodiester bond.

B-19) The single-stranded oligonucleotide described in any one of B-11) to B-18), wherein the respective terminal nucleotides of $Xb^1$ and $Xb^2$, $Xb^2$ and Xa, and $Y^2$ and $Y^1$ are coupled through a phosphorothioate bond, and the respective terminal nucleotides of Xa and $Y^2$ are coupled through a phosphodiester bond.

In the above-mentioned B-11) to B-19), the oligonucleotide Xb is represented by $Xb^1$-$Xb^2$, and the oligonucleotide Y is represented by $Y^2$—$Y^1$.

B-20) The single-stranded oligonucleotide described in 1), it is represented by the formula

[Formula 15]

$$Xb^1\text{-}Xb^2\text{-}Xb^3\text{-}Xa\text{-}Y^2\text{-}Y^1$$

(wherein, $Xb^1$ represents a group derived from an oligonucleotide $Xb^1$ that is composed of 4 to 6 sugar-modified nucleotides, $Xb^2$ represents a group derived from an oligonucleotide $Xb^2$ that is composed of 8 to 10 deoxyribonucleotides, $Xb^3$ represents a group derived from an oligonucleotide $Xb^1$ that is composed of 1 or 2 sugar-modified nucleotides, Xa is composed of 3 or 4 sugar-modified nucleotides, $Y^2$ represents a group derived from an oligonucleotide $Y^2$ that is composed of 9 to 12 ribonucleotides, and Y¹ represents a group derived from an oligonucleotide Y¹ that is composed of 4 to 6 sugar-modified nucleotides).

B-21) The single-stranded oligonucleotide described in 73), it is represented by the formula

[Formula 16]

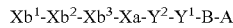

Xb¹-Xb²-Xb³-Xa-Y²-Y¹-B-A (wherein, Xb¹ represents a group derived from an oligonucleotide Xb¹ that is composed of 4 to 6 sugar-modified nucleotides, Xb² represents a group derived from an oligonucleotide Xb² that is composed of 8 to 10 deoxyribonucleotides, Xb³ represents a group derived from an oligonucleotide Xb¹ that is composed of 1 or 2 sugar-modified nucleotides, Xa is composed of 3 or 4 sugar-modified nucleotides, Y² represents a group derived from an oligonucleotide Y² that is composed of 9 to 12 ribonucleotides, Y¹ represents a group derived from an oligonucleotide Y¹ that is composed of 4 to 6 sugar-modified nucleotides.

B represents a $C_{2-20}$ alkylene group or a $C_{2-20}$ alkenylene group (the methylene groups contained in the alkylene group and the alkenylene group are each independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are each independently not replaced, or replaced with —O—, —NR$^B$— (R$^B$ represents a hydrogen atom, a $C_{1-6}$ alkyl group or a halo-$C_{1-6}$ alkyl group), —S—, —S(O)— or —S(O)$_2$—), and A represents a group derived from a functional molecule).

B-22) The single-stranded oligonucleotide described in B-21), wherein B represents a $C_{2-20}$ alkylene group (the methylene groups of the alkylene group are each independently not replaced, or replaced with —O—. The methylene groups not replaced are each independently unsubstituted, or substituted with a hydroxyl group), and A represents a group derived from tocopherol.

B-23) The single-stranded oligonucleotide described in B-21) or B-22), wherein B is coupled with the terminal nucleotide of Y¹ through a phosphodiester bond.

B-24) The single-stranded oligonucleotide described in any one of B-20) to B-23), wherein the sugar-modified nucleotide is each independently selected from the group consisting of LNA, 2'-O-methyl nucleotides, 2'-O-methoxyethyl nucleotides and 2'-O-methylcarbamoylethyl nucleotides.

B-25) The single-stranded oligonucleotide described in any one of B-20) to B-24), wherein the sugar-modified nucleotides contained in Xb¹, Xb³ and Xa are each independently LNA or 2'-O-methoxyethyl nucleotides.

B-26) The single-stranded oligonucleotide described in any one of B-20) to B-25), wherein the sugar-modified nucleotides contained in Y¹ are 2'-O-methyl nucleotides.

B-27) The single-stranded oligonucleotide described in any one of B-20) to B-26), wherein the nucleotides contained in Xb¹, Xb², Xb³, Xa and Y¹ are mutually coupled with each other through a phosphorothioate bond, and the nucleotides contained in Y² are mutually coupled with each other through a phosphodiester bond.

B-28) The single-stranded oligonucleotide described in any one of B-20) to B-27), wherein the respective terminal nucleotides of Xb¹ and Xb², Xb² and Xb³, Xb³ and Xa, and Y² and Y¹ are coupled with each other through a phosphorothioate bond, and the respective terminal nucleotides of Xa and Y² are coupled through a phosphodiester bond.

In the above-mentioned B-20) to B-28), the oligonucleotide Xb is represented by Xb¹-Xb²-Xb³, and the oligonucleotide Y is represented by Y²-Y¹.

B-29) The single-stranded oligonucleotide described in 73), it is represented by the formula

[Formula 17]

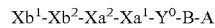

Xb¹-Xb²-Xa²-Xa¹-Y⁰-B-A (wherein, Xb¹ represents a group derived from an oligonucleotide that is composed of 2 or 3 sugar-modified nucleotides, Xb² represents a group derived from an oligonucleotide that is composed of 6 to 8 deoxyribonucleotides, Xa² represents a group derived from an oligonucleotide Xa² that is composed of 1 to 3 deoxyribonucleotides, Xa¹ represents a group derived from an oligonucleotide that is composed of 2 or 3 sugar-modified nucleotides, Y⁰ represents a group derived from an oligonucleotide that is composed of 8 to 11 ribonucleotides, B represents a $C_{2-20}$ alkylene group or a $C_{2-20}$ alkenylene group (the methylene groups contained in the alkylene group and the alkenylene group are each independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are each independently not replaced, or replaced with —O—, —NR$^B$— (R$^B$ represents a hydrogen atom, a $C_{1-6}$ alkyl group or a halo-$C_{1-6}$ alkyl group), —S—, —S(O)— or —S(O)$_2$—), and A represents a group derived from a functional molecule).

B-30) The single-stranded oligonucleotide described in B-28), wherein B represents a $C_{2-20}$ alkylene group (the methylene groups of the alkylene group are each independently not replaced, or replaced with —O—. The methylene groups not replaced are each independently unsubstituted, or substituted with a hydroxyl group), and A represents a group derived from tocopherol.

B-31) The single-stranded oligonucleotide described in B-29) or B-30), wherein B is coupled with the terminal nucleotide of Y⁰ through a phosphodiester bond.

B-32) The single-stranded oligonucleotide described in any one of B-29) to B-31), wherein Xa² is a group derived from an oligonucleotide Xa² composed of 2 or 3 deoxyribonucleotides.

B-33) The single-stranded oligonucleotide described in any one of B-29) to B-32), wherein the sugar-modified nucleotide is each independently selected from the group consisting of LNA, 2'-O-methyl nucleotides, 2'-O-methoxyethyl nucleotides and 2'-O-methylcarbamoylethyl nucleotides.

B-34) The single-stranded oligonucleotide described in any one of B-29) to B-33), wherein sugar-modified nucleotides contained in Xb¹ and Xa² are LNA, 2'-O-methoxyethyl nucleotides or 2'-O-methylcarbamoylethyl nucleotides.

B-35) The single-stranded oligonucleotide described in any one of B-29) to B-34), wherein the nucleotides contained in Xb¹, Xb², Xa¹ and Xa² are mutually coupled through a phosphorothioate bond, and the nucleotides contained in Y⁰ are mutually coupled through a phosphodiester bond.

B-36) The single-stranded oligonucleotide described in any one of B-29) to B-35), wherein the respective terminal nucleotides of Xb¹ and Xb², Xb² and Xa¹, and Xa¹ and Xa² are each coupled through a phosphorothioate bond, and the terminal nucleotides of $Xa^2$ and $Y^0$ are each coupled through a phosphodiester bond.

In the above-mentioned B-29) to B-36), the oligonucleotide Xb is represented by $Xb^1$-$Xb^2$, the oligonucleotide Xa is represented by $Xa^2$-$Xa^1$, and the oligonucleotide Y is represented by $Y^0$.

B-37) The single-stranded oligonucleotide described in 73), it is represented by the formula

[Formula 18]

$Xb^1$-$Xb^2$-Xa-$Y^0$-B-A (wherein, $Xb^1$ represents a group derived from an oligonucleotide $Xb^1$ that is composed of 4 or 5 sugar-modified nucleotides, $Xb^2$ represents a group derived from an oligonucleotide $Xb^2$ that is composed of 8 to 10 deoxyribonucleotides, Xa is composed of 4 or 5 sugar-modified nucleotides, $Y^0$ represents a group derived from oligonucleotide $Y^0$ that is composed of 12 to 15 ribonucleotides, B represents a $C_{2-20}$ alkylene group or a $C_{2-20}$ alkenylene group (the methylene groups contained in the alkylene group and the alkenylene group are each independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are each independently not replaced, or replaced with —O—, —NR$^B$— (R$^B$ represents a hydrogen atom, a $C_{1-6}$ alkyl group or a halo-$C_{1-6}$ alkyl group), —S—, —S(O)— or —S(O)$_2$—), and A represents a group derived from a functional molecule).

B-38) The single-stranded oligonucleotide described in B-37), wherein B represents a $C_{2-20}$ alkylene group (the methylene groups of the alkylene group are each independently not replaced, or replaced with —O—. The methylene groups not replaced are each independently unsubstituted, or substituted with a hydroxyl group), and A represents a group derived from tocopherol.

B-39) The single-stranded oligonucleotide described in B-37) or B-38), wherein B is coupled with the terminal nucleotide of $Y^0$ through a phosphodiester bond.

B-40) The single-stranded oligonucleotide described in any one of B-37) to B-39), wherein the sugar-modified nucleotides are each independently selected from the group consisting of LNA, 2'-O-methyl nucleotides, 2'-O-methoxyethyl nucleotides and 2'-O-methylcarbamoylethyl nucleotides.

B-41) The single-stranded oligonucleotide described in any one of B-37) to B-40), wherein the sugar-modified nucleotides contained in $Xb^1$ and Xa are each independently LNA, 2'-O-methoxyethyl nucleotide or 2'-O-methylcarbamoylethyl nucleotide.

B-42) The single-stranded oligonucleotide described in any one of B-37) to B-41), wherein the nucleotides contained in $Xb^1$, $Xb^2$, and Xa are mutually coupled through a phosphorothioate bond, and the nucleotides contained in $Y^0$ are mutually coupled through a phosphodiester bond.

B-43) The single-stranded oligonucleotide described in any one of B-37) to B-42), wherein the respective terminal nucleotides of $Xb^1$ and $Xb^2$, and $Xb^2$ and Xa are mutually coupled through a phosphorothioate bond, and the respective terminal nucleotides of Xa and $Y^0$ are mutually coupled through a phosphodiester bond.

In the above-mentioned B-37) to B-43), the oligonucleotide Xb is represented by $Xb^1$-$Xb^2$, and the oligonucleotide Y is represented by $Y^0$.

B-44) The single-stranded oligonucleotide described in 73), it is represented by the formula

[Formula 19]

$Xb^1$-$Xb^2$-$Xb^3$-Xa-$Y^0$-B-A (wherein, $Xb^1$ represents a group derived from an oligonucleotide $Xb^1$ that is composed of 4 to 6 sugar-modified nucleotides, $Xb^2$ represents a group derived from an oligonucleotide $Xb^2$ that is composed of 8 to 10 deoxyribonucleotides, $Xb^3$ represents a group derived from an oligonucleotide $Xb^1$ that is composed of 1 or 2 sugar-modified nucleotides, Xa is composed of 3 or 4 sugar-modified nucleotides, $Y^0$ represents a group derived from oligonucleotide $Y^0$ that is composed of 13 to 18 ribonucleotides, B represents a $C_{2-20}$ alkylene group or a $C_{2-20}$ alkenylene group (the methylene groups contained in the alkylene group and the alkenylene group are each independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are each independently not replaced, or replaced with —O—, —NR$^B$— (R$^B$ represents a hydrogen atom, a $C_{1-6}$ alkyl group or a halo-$C_{1-6}$ alkyl group), —S—, —S(O)— or —S(O)$_2$—), and A represents a group derived from a functional molecule).

B-45) The single-stranded oligonucleotide described in B-42), wherein B represents a $C_{2-20}$ alkylene group (the methylene groups of the alkylene group are each independently not replaced, or replaced with —O—. The methylene groups not replaced are each independently unsubstituted, or substituted with a hydroxyl group), and A represents a group derived from tocopherol.

B-46) The single-stranded oligonucleotide described in B-44) or B-45), wherein B is coupled with the terminal nucleotide of $Y^0$ through a phosphodiester bond.

B-47) The single-stranded oligonucleotide described in any one of B-44) to B-46), wherein the sugar-modified nucleotide is each independently selected from the group consisting of LNA, 2'-O-methyl nucleotides, 2'-O-methoxyethyl nucleotides and 2'-O-methylcarbamoylethyl nucleotides.

B-48) The single-stranded oligonucleotide described in any one of B-44) to B-47), wherein the sugar-modified nucleotides contained in $Xb^1$, $Xb^3$ and Xa are each independently LNA, 2'-O-methoxyethyl nucleotide or 2'-O-methylcarbamoylethyl nucleotide.

B-49) The single-stranded oligonucleotide described in any one of B-44) to B-47), wherein the sugar-modified nucleotides contained in $Xb^1$, $Xb^3$ and Xa are 2'-O-methylcarbamoylethyl nucleotide.

B-50) The single-stranded oligonucleotide described in any one of B-44) to B-48), wherein the nucleotides contained in $Xb^1$, $Xb^2$, $Xb^3$, and Xa are mutually coupled through a phosphorothioate bond, and the nucleotides contained in $Y^0$ are mutually coupled through a phosphodiester bond.

B-51) The single-stranded oligonucleotide described in any one of B-44) to B-50), wherein the respective terminal nucleotides of $Xb^1$ and $Xb^2$, $Xb^2$ and $Xb^3$, and $Xb^3$ and Xa are coupled through a phosphorothioate bond, and the respective terminal nucleotides of Xa and $Y^0$ are coupled through a phosphodiester bond.

In the above-mentioned B-44) to B-51), the oligonucleotide Xb is represented by $Xb^1$-$Xb^2$-$Xb^3$, and the oligonucleotide Y is represented by $Y^0$.

B-52) The single-stranded oligonucleotide in any one of 1) to 85) and B-1) to B-51), wherein the base moiety of deoxyribonucleotides, ribonucleotides and sugar-modified nucleotides is at least one kind selected from the group consisting of adenine (A), guanine (G), thymine (T), cytosine (C), uracil (U) and 5-methylcytosine (5-me-C).

D-1) A pharmaceutical containing as an active ingredient thereof the single-stranded oligonucleotide described in any one of 1) to 85) and B-1) to B-52).

A conceptual diagram of the single-stranded oligonucleotide described in B-1), in which the portion represented by $Xb^1$-$Xb^2$-$Xa^2$-$Xa^1$ is an antisense sequence portion, and the portion represented by $Xb^1$-$Xb^2$ and the portion represented by $Y^2$—$Y^1$ hybridize within the molecule thereof, is shown in FIG. 1. In the single-stranded oligonucleotide shown in FIG. 1, $Xb^1$ composed of 2 or 3 sugar-modified nucleotides, $Xb^2$ composed of 6 to 8 deoxyribonucleotides, $Xa^1$ composed of 1 to 3 deoxyribonucleotides, $Xa^2$ composed of 2 or 3 sugar-modified nucleotides, $Y^2$ composed of 6 to 8 ribonucleotides and $Y^1$ composed of 2 or 3 sugar-modified nucleotides are bound in this order. The direction of bonding from $Xb^1$ to $Y^1$ may be in the 5' to 3' direction or in the 3' to 5' direction. In FIG. 1, $Xb^2$ and $Y^2$ form a double strand. $Xb^1$ and $Y^1$ form a double strand.

Figure 2:
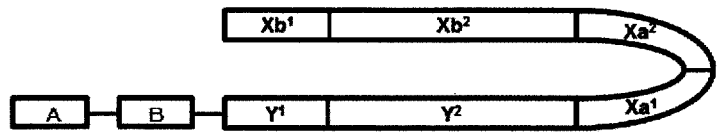
FIG. 2 is a conceptual diagram representing one aspect in which Xb and Y of an example of the present embodiment in the form of a single-stranded oligonucleotide hybridize within the molecule thereof.

A conceptual diagram of the single-stranded oligonucleotide described in B-2), in which the portion represented by $Xb^1$-$Xb^2$-$Xa^2$-$Xa^1$ is an antisense sequence portion, and the portion represented by $Xb^1$-$Xb^2$ and the portion represented by $Y^2$—$Y^1$ hybridize within the molecule thereof, is shown in FIG. 2. In the single-stranded oligonucleotide shown in FIG. 2, $Xb^1$ composed of 2 or 3 sugar-modified nucleotides, $Xb^2$ composed of 6 to 8 deoxyribonucleotides, $Xa^1$ composed of 1 to 3 deoxyribonucleotides, $Xa^2$ composed of 2 or 3 sugar-modified nucleotides, $Y^2$ composed of 6 to 8 ribonucleotides, $Y^1$ composed of 2 or 3 sugar-modified nucleotides, B which is a $C_{2-20}$ alkylene group and the like, and A which is a group derived from a functional molecule, are bound in this order. The direction of bonding from $Xb^1$ to $Y^1$ may be in the 5' to 3' direction or in the 3' to 5' direction. In FIG. 2, $Xb^2$ and $Y^2$ form a double strand. $Xb^1$ and $Y^1$ form a double strand.

Figure 3:
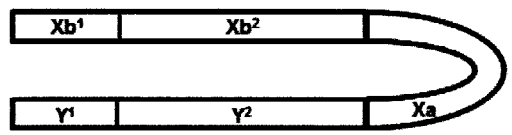
FIG. 3 is a conceptual diagram representing one aspect in which Xb and Y of an example of the present embodiment in the form of a single-stranded oligonucleotide hybridize within the molecule thereof.

A conceptual diagram of the single-stranded oligonucleotide described in B-11), in which the portion represented by $Xb^1$-$Xb^2$-Xa is an antisense sequence portion, and the portion represented by $Xb^1$-$Xb^2$ and the portion represented by $Y^2$—$Y^1$ hybridize within the molecule thereof, is shown in FIG. 3. In the single-stranded oligonucleotide shown in FIG. 3, $Xb^1$ composed of 4 or 5 sugar-modified nucleotides, $Xb^2$ composed of 8 to 10 deoxyribonucleotides, Xa composed of 4 or 5 sugar-modified nucleotides, $Y^2$ composed of 8 to 10 ribonucleotides, and $Y^1$ composed of 4 or 5 sugar-modified nucleotides, are bound in this order. The direction of bonding from $Xb^1$ to $Y^1$ may be in the 5' to 3' direction or in the 3' to 5' direction. In FIG. 3, $Xb^2$ and $Y^2$ form a double strand. $Xb^1$ and $Y^1$ form a double strand.

Figure 4:
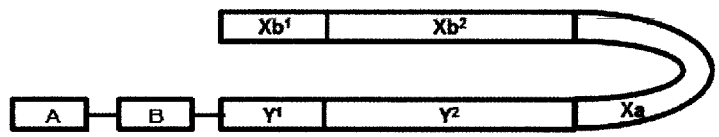
FIG. 4 is a conceptual diagram representing one aspect in which Xb and Y of an example of the present embodiment in the form of a single-stranded oligonucleotide hybridize within the molecule thereof.

A conceptual diagram of the single-stranded oligonucleotide described in B-12), in which the portion represented by $Xb^1$-$Xb^2$-Xa is an antisense sequence portion, and the portion represented by $Xb^1$-$Xb^2$ and the portion represented by $Y^2$-$Y^1$ hybridize within the molecule thereof, is shown in FIG. 4. In the single-stranded oligonucleotide shown in FIG. 4, $Xb^1$ composed of 4 or 5 sugar-modified nucleotides, $Xb^2$ composed of 8 to 10 deoxyribonucleotides, Xa composed of 4 or 5 sugar-modified nucleotides, $Y^2$ composed of 8 to 10 ribonucleotides, $Y^1$ composed of 4 or 5 sugar-modified nucleotides, B which is a $C_{2-20}$ alkylene group and the like, and A which is a group derived from a functional molecule, are bound in this order. The direction of bonding from $Xb^1$ to $Y^1$ may be in the 5' to 3' direction or in the 3' to 5' direction. In FIG. 4, $Xb^2$ and $Y^2$ form a double strand. $Xb^1$ and $Y^1$ form a double strand.

Figure 5:
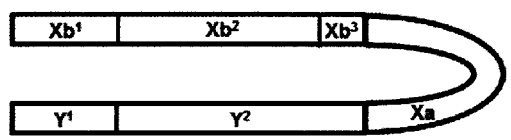
FIG. 5 is a conceptual diagram representing one aspect in which Xb and Y of an example of the present embodiment in the form of a single-stranded oligonucleotide hybridize within the molecule thereof.

A conceptual diagram of the single-stranded oligonucleotide described in B-20), in which the portion represented by $Xb^1$-$Xb^2$-$Xb^3$-Xa is an antisense sequence portion, and the portion represented by $Xb^1$-$Xb^2$-$Xb^3$ and the portion represented by $Y^2$—$Y^1$ hybridize within the molecule thereof, is shown in FIG. 5. In the single-stranded oligonucleotide shown in FIG. 5, $Xb^1$ composed of 4 to 6 sugar-modified nucleotides, $Xb^2$ composed of 8 to 10 deoxyribonucleotides, $Xb^3$ composed of 1 or 2 sugar-modified nucleotides, Xa composed of 3 or 4 sugar-modified nucleotides, $Y^2$ composed of 9 to 12 ribonucleotides, and $Y^1$ composed of 4 to 6 sugar-modified nucleotide, are bound in this order. The direction of bonding from $Xb^1$ to $Y^1$ may be in the 5' to 3' direction or in the 3' to 5' direction. In FIG. 5, $Xb^2$ and $Y^2$ form a double strand. $Xb^1$ and $Y^1$ form a double strand.

Figure 6:
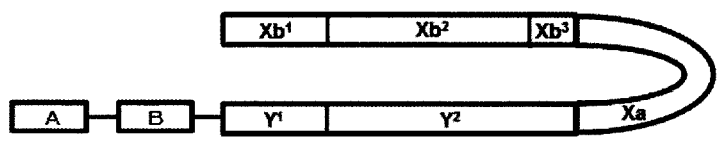
FIG. 6 is a conceptual diagram representing one aspect in which Xb and Y of an example of the present embodiment in the form of a single-stranded oligonucleotide hybridize within the molecule thereof.

A conceptual diagram of the single-stranded oligonucleotide described in B-21), in which the portion represented by $Xb^1$-$Xb^2$-$Xb^3$-Xa is an antisense sequence portion, and the portion represented by $Xb^1$-$Xb^2$-$Xb^3$ and the portion represented by $Y^2$-$Y^1$ hybridize within the molecule thereof, is shown in FIG. 6. In the single-stranded oligonucleotide shown in FIG. 6, $Xb^1$ composed of 4 to 6 sugar-modified nucleotides, $Xb^2$ composed of 8 to 10 deoxyribonucleotides, $Xb^3$ composed of 1 or 2 sugar-modified nucleotides, Xa composed of 3 or 4 sugar-modified nucleotides, $Y^2$ composed of 9 to 12 ribonucleotides, $Y^1$ composed of 4 to 6 sugar-modified nucleotides, B which is a $C_{2-20}$ alkylene group and the like, and A which is a group derived from a functional molecule, are bound in this order. The direction of bonding from $Xb^1$ to $Y^1$ may be in the 5' to 3' direction or in the 3' to 5' direction. In FIG. 6, $Xb^2$ and $Y^2$ form a double strand. $Xb^1$ and $Y^1$ form a double strand.

Figure 7:
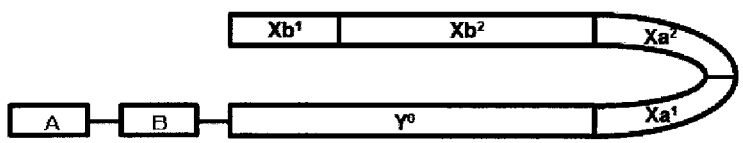
FIG. 7 is a conceptual diagram representing one aspect in which Xb and Y of an example of the present embodiment in the form of a single-stranded oligonucleotide hybridize within the molecule thereof.

A conceptual diagram of the single-stranded oligonucleotide described in B-29), in which the portion represented by $Xb^1$-$Xb^2$-$Xa^2$-$Xa^1$ is an antisense sequence portion, and the portion represented by $Xb^1$-$Xb^2$ and the portion represented by $Y^0$ hybridize within the molecule thereof, is shown in FIG. 7. In the single-stranded oligonucleotide shown in FIG. 7, $Xb^1$ composed of 2 or 3 sugar-modified nucleotides, $Xb^2$ composed of 6 to 8 deoxyribonucleotides, $Xa^1$ composed of 1 to 3 deoxyribonucleotides, $Xa^2$ composed of 2 or 3 sugar-modified nucleotides, $Y^0$ composed of 8 to 11 ribonucleotide, B which is a $C_{2-20}$ alkylene group and the like, and A which is a group derived from a functional molecule, are bound in this order. The direction of bonding from $Xb^1$ to $Y^0$ may be in the 5' to 3' direction or in the 3' to 5' direction. In FIG. 7, $Xb^2$ and $Y^0$ form a double strand. $Xb^1$ and $Y^0$ form a double strand.

Figure 8:
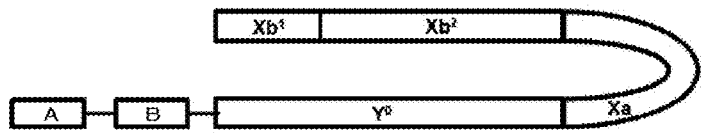
FIG. 8 is a conceptual diagram representing one aspect in which Xb and Y of an example of the present embodiment in the form of a single-stranded oligonucleotide hybridize within the molecule thereof.

A conceptual diagram of the single-stranded oligonucleotide described in B-37), in which the portion represented by $Xb^1$-$Xb^2$-Xa is an antisense sequence portion, and the portion represented by $Xb^1$-$Xb^2$ and the portion represented by $Y^0$ hybridize within the molecule thereof, is shown in FIG. 8. In the single-stranded oligonucleotide shown in FIG. 8, $Xb^1$ composed of 4 or 5 sugar-modified nucleotides, $Xb^2$ composed of 8 to 10 deoxyribonucleotides, Xa composed of 4 or 5 sugar-modified nucleotides, $Y^0$ composed of 12 to 15 ribonucleotides, B which is a $C_{2-20}$ alkylene group and the like, and A which is a group derived from a functional molecule, are bound in this order. The direction of bonding from $Xb^1$ to $Y^0$ may be in the 5' to 3' direction or in the 3' to 5' direction. In FIG. 8, $Xb^2$ and $Y^0$ form a double strand. $Xb^1$ and $Y^0$ form a double strand.

Figure 9:
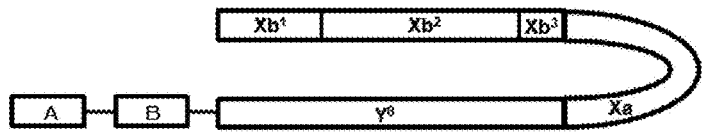
FIG. 9 is a conceptual diagram representing one aspect in which Xb and Y of an example of the present embodiment in the form of a single-stranded oligonucleotide hybridize within the molecule thereof.

A conceptual diagram of the single-stranded oligonucleotide described in B-44), in which the portion represented by $Xb^1$-$Xb^2$-$Xb^3$-Xa is an antisense sequence portion, and the portion represented by $Xb^1$-$Xb^2$-$Xb^3$ and the portion represented by $Y^0$ hybridize within the molecule thereof, is shown in FIG. 9. In the single-stranded oligonucleotide shown in FIG. 9, $Xb^1$ composed of 4 to 6 sugar-modified nucleotides, $Xb^2$ composed of 8 to 10 deoxyribonucleotides, $Xb^3$ composed of 1 or 2 sugar-modified nucleotides, Xa composed of 3 or 4 sugar-modified nucleotides, $Y^0$ composed of 13 to 18 ribonucleotides, B which is a $C_{2-20}$ alkylene group and the like, and A which is a group derived from a functional molecule, are bound in this order. The direction of bonding from $Xb^1$ to $Y^0$ may be in the 5' to 3' direction or in the 3' to 5' direction. In FIG. 9, $Xb^2$ and $Y^0$ form a double strand. $Xb^1$ and $Y^0$ form a double strand.

The following lists examples of preferable methods for using the single-stranded oligonucleotide of the present invention.

E-1) A method for controlling a function of a target RNA, comprising a step for contacting the single-stranded nucleotide described in any one of 1) to 85) and B-1) to B-52) with a cell.

E-2) A method for controlling a function of a target RNA in a mammal, comprising a step for administering a pharmaceutical composition containing the single-stranded oligonucleotide described in any one of 1) to 85) and B-1) to B-52) to the mammal.

E-3) The method described in E-2), wherein the mammal is a human.

E-4) The method described in E-2) or E-3), wherein an administration route is enteral.

E-5) The method described in E-2) or E-3), wherein an administration route is parenteral.

E-6) A use of the single-stranded oligonucleotide described in any one of 1) to 85) and B-1) to B-52) for controlling a function of a target RNA in a mammal.

E-7) A use of the single-stranded oligonucleotide described in any one of 1) to 85) and B-1) to B-52) for producing a drug for controlling a target RNA in a mammal.

E-8) The use described in E-6) or E-7), wherein the mammal is a human.

Control of the function of a target RNA in the present invention refers to suppressing translation or regulating or converting a splicing function such as exon splicing that occurs by covering a portion of a target RNA due to hybridization by an antisense sequence portion, or suppressing a function of a target RNA by degrading the above-mentioned target RNA that is able to occur as a result of recognition of a hybridized portion of an antisense sequence portion and a part of the target RNA.

E-9) A method for controlling an expression of a target gene, comprising a step for contacting the single-stranded oligonucleotide described in any one of 1) to 85) and B-1) to B-52) with a cell.

E-10) A method for controlling an expression of a target gene in a mammal, comprising a step for administering a pharmaceutical composition containing the single-stranded oligonucleotide described in any one of 1) to 85) and B-1) to B-52) to the mammal.

E-11) The method described in E-10), wherein the mammal is a human.

E-12) The method described in E-10) or E-11), wherein an administration route is enteral.

E-13) The method described in E-10) or E-11), wherein an administration route is parenteral.

E-14) A use of the single-stranded oligonucleotide described in any one of 1) to 85) and B-1) to B-52) for controlling an expression of a target gene in a mammal.

E-15) A use of the single-stranded oligonucleotide described in any one of 1) to 85) and B-1) to B-52) for producing a drug for controlling an expression of a target gene in a mammal.

E-16) The use described in E-14) or E-15), wherein the mammal is a human.

Although the above has provided an explanation of preferable aspects of the single-stranded oligonucleotides, the single-stranded oligonucleotide of the present invention is not limited to the above-mentioned aspects. The single-stranded oligonucleotide includes, for example that included therein which is present after having undergone tautomerism or geometrical isomerism regardless of whether endocyclic or exocyclic, as well as that present as mixtures thereof or as mixtures of respective isomers thereof. In addition, in the case of the presence of an asymmetric center or in the case of generating an asymmetric center as a result of isomerization, the single-stranded oligonucleotide includes that which is present as respective optical isomers thereof and mixtures of arbitrary ratios. In addition, in the case of a compound having two or more asymmetric centers, diastereomers are also present due to their respective optical isomers. The present invention includes all of these forms in optional ratio thereof.

The present invention also includes a pharmaceutically acceptable salt of the single-stranded nucleotide represented by the formula (I).

The single-stranded oligonucleotide represented by the formula (I) can also be converted to a pharmaceutically acceptable salt or released from a formed salt as necessary. Examples of the pharmaceutically acceptable salt of the single-stranded oligonucleotide represented by the formula (I) include a salt formed with an alkaline metal (such as lithium, sodium and potassium), an alkaline earth metal (such as magnesium and calcium), ammonium, an organic base (such as triethylamine and trimethylamine), an amino acid (such as glycine, lysine and glutamic acid), inorganic acids (such as hydrochloric acid, hydrobromic acid, phosphoric acid and sulfuric acid), and an organic acid (such as acetic acid, citric acid, maleic acid, fumaric acid, tartaric acid, benzenesulfonic acid, methanesulfonic acid and p-toluenesulfonic acid).

In particular, a partial structure represented by —P(=O)(OH)— may be converted to an anionic partial structure represented by —P(=O)(O⁻)— to form a salt with an alkaline metal (such as lithium, sodium and potassium), an alkaline earth metal (such as magnesium and calcium) or ammonium. In addition, a partial structure represented by —P(=O)(SH)—, which forms a phosphorothioate bond, may be converted to an anionic partial structure represented by —P(=O)(S⁻)— to similarly form a salt with an alkaline metal, an alkaline earth metal or ammonium.

The present invention also includes a prodrug of the single-stranded oligonucleotide represented by the formula (I).

A prodrug refers to a derivative of a pharmaceutical compound having a group that can be chemically or metabolically degraded, and is a compound that is degraded by solvolysis or in vivo under physiological conditions and derived to a pharmacologically active pharmaceutical compound. Suitable methods for selecting and producing prodrug derivatives are described in, for example, Design of Prodrugs, (Elsevier, Amsterdam, 1985). In the case of the present invention, and in the case of having a hydroxyl group, an example of the prodrug is an acyloxy derivative produced by reacting the compound with a suitable acyl halide, a suitable acid anhydride or a suitable halogenated alkyloxycarbonyl compound. Particularly preferable examples of the structures of the prodrug include —O—$COC_2H_5$, —O—CO(t-Bu), —O—$COC_{15}H_{31}$, —O—CO(m-$CO_2$Na-Ph), —O—$COCH_2CH_2CO_2$Na— $OCOCH(NH_2)CH_3$, —O—$COCH_2N(CH_3)_2$ or —O—$CH_2OC(=O)CH_3$. In the case the single-stranded oligonucleotide that forms the present invention has an amino group, examples of the prodrug include those produced by reacting the compound having an amino group with a suitable acid halide, a suitable mixed acid anhydride or a suitable halogenated alkyloxycarbonyl compound. Particularly preferable examples of the structure of the prodrug include —NH—$CO(CH_2)_{20}OCH_3$, —NH—$COCH(NH_2)$ $CH_3$, —NH—$CH_2OC(=O)CH_3$ and the like.

Although the single-stranded oligonucleotide indicated in the formula (I) of the present invention, or a pharmaceutically acceptable salt thereof, can be present in an arbitrary crystalline form or arbitrary hydrate according to the production conditions, these crystalline forms, hydrates and mixtures thereof are included within the scope of the present invention. In addition, it can also be present as a solvate of an organic solvent such as acetone, ethanol, 1-propanol, 2-propanol and the like, and all of these forms are also included within the scope of the present invention.

The single-stranded oligonucleotide can be produced by suitably selecting a method known among persons with ordinary skill in the art. For example, a person with ordinary skill in the art is able to synthesize the single-stranded oligonucleotide by designing the nucleotide sequence of the single-stranded oligonucleotide based on nucleotide sequence data of a target RNA and then synthesizing the single-stranded oligonucleotide using a commercially available automated nucleic acid synthesizer (such as that manufactured by Applied Biosystems, Beckman or GeneDesign Inc.). In addition, it can also be synthesized by a reaction using enzymes. Examples of the above-mentioned enzymes include, but are not limited to, polymerases, ligases and restriction enzymes. Namely, a method for producing the single-stranded oligonucleotide according to the present embodiment can comprise a step for extending a nucleotide strand at the 3'-end or 5'-end of an oligonucleotide containing at least one of X, Y, Xz, Yz, Lx and Ly (among them, an oligonucleotide containing at least one of X and Y).

Numerous methods are known in the art for bonding functional molecules with the oligonucleotide, and examples thereof can be referred to in, for example, European Journal of Pharmaceuticals and Biopharmaceutics, Vol. 107, pp. 321-340 (2016), Advanced Drug Delivery Reviews, Vol. 104, pp. 78-92 (2016), or Expert Opinion on Drug Delivery, Vol. 11, pp. 791-822 (2014). For example, after bonding a functional molecule and a linker according to a known method, the resulting material is derived to an amidite with an amiditation reagent or derived to an H-phosphonate form with an H-phosphonate reagent followed by bonding to the oligonucleotide.

A single-stranded oligonucleotide can be prepared by purifying the resulting oligonucleotide by reversed phase column chromatography and the like. A single-stranded oligonucleotide that has hybridized within a molecule thereof can be prepared by mixing the prepared single-stranded oligonucleotide in a suitable buffer solution and denaturing for several minutes (such as 5 minutes) at 90° C. to 98° C. followed by hybridizing over the course of 1 to 8 hours at 30° C. to 70° C. There are cases in which the intramolecular hybridization step can be omitted.

The single-stranded oligonucleotide is able to effectively control expression of a target gene. Thus, the present invention is able to provide a composition containing the single-stranded oligonucleotide as an active ingredient thereof for, for example, controlling expression of a target gene based on an antisense effect. In particular, since the single-stranded oligonucleotide allows the obtaining of high pharmacological efficacy by administering at a low concentration, pharmaceutical compositions for the treatment, prevention and improvement of diseases such as metabolic diseases, tumors or infections associated with overexpression of a target gene can also be provided in several embodiments.

A composition containing the single-stranded oligonucleotide can be formulated according to a known pharmaceutical preparation method. For example, a composition containing the single-stranded oligonucleotide can be used either enterally (such as orally) or parenterally as a capsule, tablet, pill, liquid, powder, granule, fine granule, film-coated preparation, pellet, troche, sublingual preparation, chewed preparation, buccal preparation, paste, syrup, suspension, elixir, emulsion, coating preparation, ointment, plaster, poultice, transcutaneously absorbed preparation, lotion, inhalant, aerosol, injection preparation or suppository.

These preparations can be suitably combined with a pharmaceutically acceptable carrier or a carrier in the form of a food or beverage, specific examples of which include sterile water or physiological saline, vegetable oil, solvent, base, emulsifier, suspending agent, surfactant, pH adjuster, stabilizer, flavoring agent, fragrance, excipient, vehicle, preservative, binder, diluent, isotonic agent, analgesic, filler, disintegration agent, buffer, coating agent, lubricant, colorant, sweetener, thickening agents, corrective, solubilizing aid and other additives.

There are no particular limitations on the administration form of the composition containing the single-stranded oligonucleotide, and examples thereof include enteral (oral and the like) and parenteral administration. More preferably, examples of administration forms include intravenous administration, intraarterial administration, intraperitoneal administration, subcutaneous administration, intradermal administration, intratracheal administration, rectal administration, intramuscular administration, intrathecal administration, intraventricular administration, transnasal administration and intravitreal administration, and administration by infusion.

There are no particular limitations on the disease able to be treated, prevented or improved by using the single-stranded oligonucleotide, and examples thereof include metabolic diseases, circulatory diseases, tumors, infections, ophthalmic diseases, inflammatory diseases, autoimmune diseases, hereditary rare diseases, and diseases caused by expression of a gene. Specific examples include hypercholesterolemia, hypertriglyceridemia, spinal muscular atrophy, muscular dystrophy (such as Duchenne muscular dystrophy, myotonic dystrophy, congenital muscular dystrophy (such as Fukuyama-type congenital muscular dystrophy, Ullrich-type congenital muscular dystrophy, merosin-deficient congenital muscular dystrophy, integrin deficiency or Walker Warburg syndrome), Becker muscular dystrophy, limb-girdle muscular dystrophy, Miyoshi muscular dystrophy or facioscapulohumeral muscular dystrophy), Huntington's disease, Alzheimer's disease, transthyretin amyloidosis, familial amyloid cardiomyopathy, multiple sclerosis, Crohn's disease, inflammatory bowel disease, acromegaly, type 2 diabetes, chronic nephropathy, RS virus infection, Ebola hemorrhagic fever, Marburg virus, HIV, influenza, hepatitis B, hepatitis C, cirrhosis, chronic cardiac insufficiency, myocardial fibrosis, atrial fibrillation, prostate cancer, melanoma, breast cancer, pancreatic cancer, colorectal cancer, renal cell carcinoma, cholangiocarcinoma, cervical cancer, liver cancer, lung cancer, leukemia, non-Hodgkin's lymphoma, atopic dermatitis, glaucoma and age-related macular degeneration. The gene causing the above-mentioned disease can be set for the above-mentioned target gene corresponding to the type of the disease, and the above-mentioned expression control sequence (such as an antisense sequence) can be suitably set corresponding to the sequence of the above-mentioned target gene.

In addition to primates such as humans, a variety of other mammalian diseases can be treated, prevented, ameliorated by compositions comprising single-stranded oligonucleotides. For example, although not limited thereto, various diseases of species of mammals, including cows, sheep, goats, horses, dogs, cats, guinea pigs and other bovines, ovines, equines, canines, felines and species of rodents such as mice can be treated. In addition, a composition containing the single-stranded oligonucleotide can also be applied to other species such as birds (such as chickens).

When a composition containing a single-stranded oligonucleotide is administered or fed to animals including humans, the administration dose or ingested amount thereof can be suitably selected depending on the age, body weight, symptoms or health status of the subject or the type of the composition (pharmaceuticals, food and drink) and the like, and the administration dose or ingested amount is preferably 0.0001 mg/kg/day to 100 mg/kg/day as the amount of the single-stranded oligonucleotide.

The single-stranded oligonucleotide is able to control expression of a target gene extremely effectively. Thus, a method for controlling expression of a target gene by an antisense effect can be provided by administering the single-stranded oligonucleotide to animals, including humans. In addition, a method for treating, preventing or improving various diseases associated with overexpression of a target gene can be also provided, which comprises administrating a composition containing the single-stranded oligonucleotide to animals, including humans.

EXAMPLE

Although the following provides a more detailed explanation of the present invention based on Examples and Comparative Examples, embodiments of the present invention are not limited to the following Examples. In the following Example and FIGS. 10, 12 and 14, "Example" refers to Example, "Comparative" refers to Comparative Example, and "control" refers to control.

Example 1, Comparative Example 1

The oligonucleotides described in Table 1 were prepared using Automated Nucleic Acid Synthesizer nS-8II (manufactured by GeneDesign). The target gene is mouse scavenger receptor class B member 1 (SRB1). Incidentally, in the sequence notations shown in Table 1, "(L)" refers to LNA, "(M)" refers to 2'-O-methyl nucleotide, alphabets of lower case refer to deoxyribonucleotide, alphabets of upper case (except for the above-mentioned alphabets attached with (L) and (M)) refers to ribonucleotide, "^" refers to a phosphorothioate bond, "5" indicates that the base of the nucleotide is 5-methylcytosine. "Toc-TEG-" indicates that a moiety obtained by removing a hydrogen atom from the hydroxyl group of the tocopherol represented by the following formula (IV) is bound to a single oxygen atom of the phosphate group on the 5'-end through a group represented by the following formula (III-2):

[Formula 20]

(III-2)

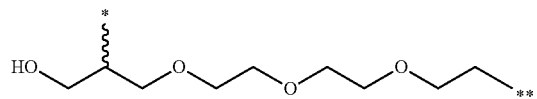

(wherein, one asterisk (*) represents a bonding site with the oligonucleotide Y, while two asterisks (**) represent a bonding site with tocopherol).

[Formula 21]

(IV)

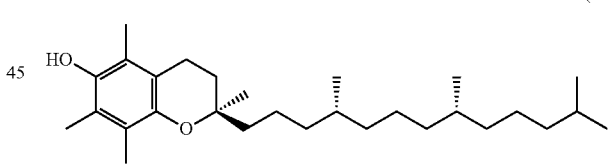

TABLE 1

| | Sequence (left side represents 5'-side and right side represents 3'-side) | Remarks |
|---|---|---|
| Example 1 (SEQ ID NO: 1) | Toc-TEG-G(M)^A(M)^AGUCAUGAT (L)^5(L)^a^g^t^c^a^t^g^a^c^t^T(L)^5(L) | Bases 1-10: Y Bases 11-24: X (Bases 11-14: Xa, Bases 15-24: Xb) |
| Comparative Example 1 (SEQ ID NO: 2, 3) | T(L)^5(L)^a^g^t^c^a^t^g^a^c^t^T(L)^5(L) Toc-TEG-G(M)^A(M)^AGUCAUGACU^G(M)^A(M) | Functional molecule is bound |

Intramolecular hybridization in Example 1 and intermolecular hybridization between two oligonucleotides in Comparative Example 1 were carried out by heating for 5 minutes at 95° C. followed by allowing to stand for 1 hour at 37° C. with a constant temperature. Hybridization was confirmed by nondenaturing polyacrylamide gel electrophoresis.

Evaluation Example 1

Example 1 and Comparative Example 1 each dissolved in physiological saline (Otsuka Normal Saline, Otsuka Pharmaceutical Factory) were intravenously administered to C57BL/6J mouse (male, five-weeks old, Japan Charles River) so that the dosage per mouse body weight was 40 nmol/kg in terms of the amount of the antisense oligonucleotide. Only physiological saline (Otsuka Normal Saline, Otsuka Pharmaceutical Factory) was administrated as a control. After collecting blood from the orbital venous plexus 3 days after administration, liver tissue was removed under isoflurane anesthesia. Extraction of RNA from the liver was carried out using the RNeasy Mini Kit (manufactured by Qiagen) according to the recommended protocol of Qiagen. cDNA was obtained from total RNA using the PrimeScript RT Master Mix (manufactured by Takara Bio Inc.). Real-time PCR was then carried out with the 7500 Real-Time PCR System (manufactured by Applied Biosystems) using the resulting cDNA and TaqMan® Gene Expression ID (manufactured by Applied Biosystems) to determine the amount of mRNA of SRB1. During real-time PCR, the amount of mRNA of a housekeeping gene in the form of Cyclophilin was simultaneously assayed, and the amount of mRNA of SRB1 relative to the amount of mRNA of Cyclophilin was evaluated as the expression level of SRB1. The results are shown in FIG. 10.

Incidentally, the primer used was TaqMan Gene Expression Assay (manufactured by Applied Biosystems), and the Assay ID was as follows:

Mouse SRB1 assay: Mm00450234_m1
Mouse Cyclophilin assay: Mm0234230_g1

Figure 10:
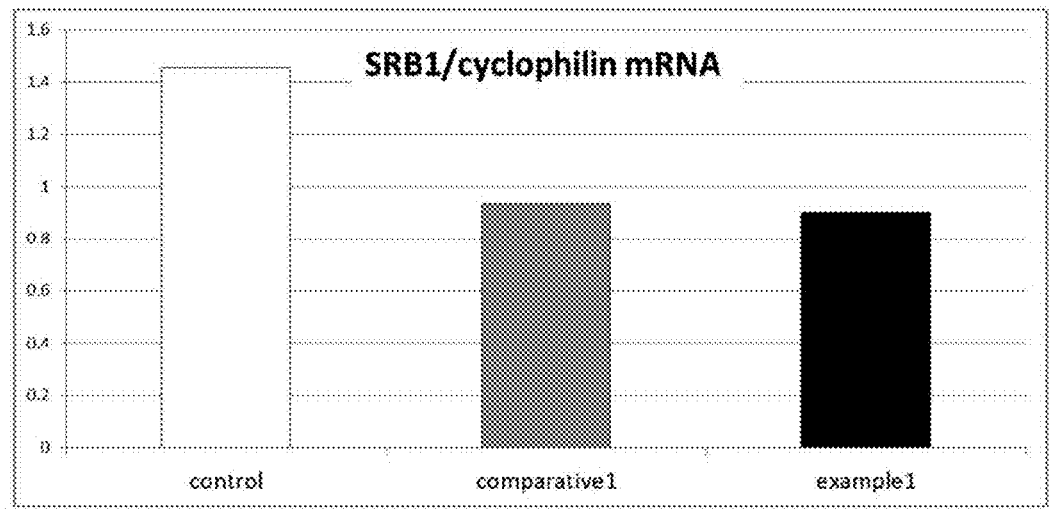
FIG. 10 is a graph indicating the effects on the expression level of SRB1 in the liver of C57BL/6J mice administered a single-stranded oligonucleotide according to the present embodiment.

As is clear from FIG. 10, the single-stranded oligonucleotide (Example 1) according to the present invention were confirmed to demonstrate a similar antisense effect in comparison with HDO (Comparative Example 1).

Evaluation Example 2

Figure 11:
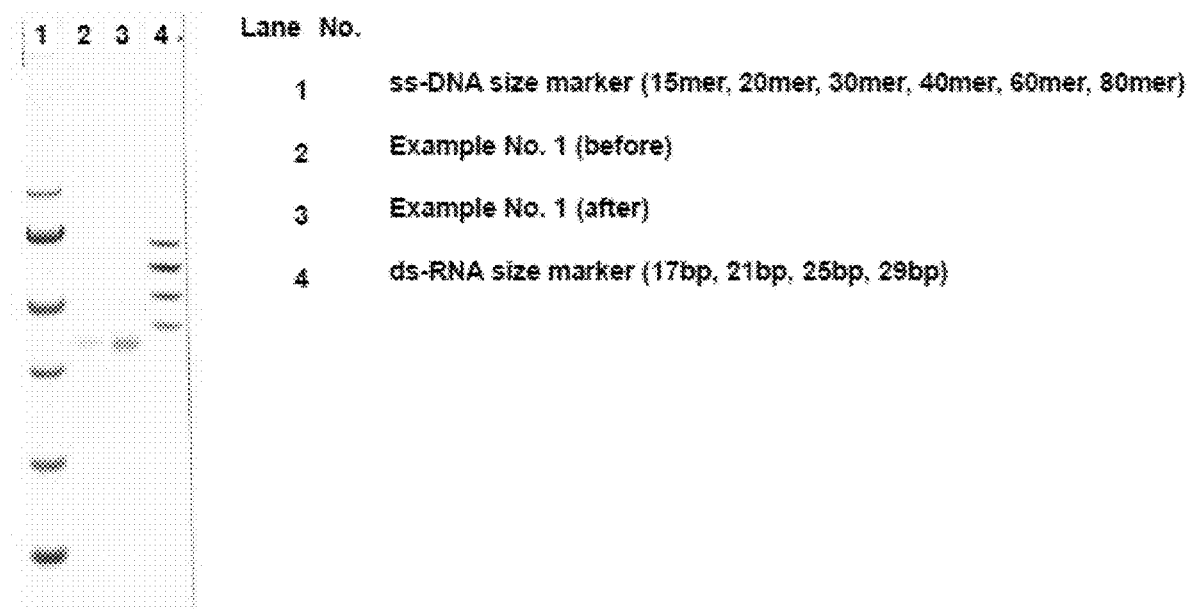
FIG. 11 indicates the results of gel electrophoresis of single-stranded nucleotides according to the present embodiment before and after hybridization treatment.

The results of nondenaturing polyacrylamide gel electrophoresis before and after the above-mentioned intramolecular hybridization treatment in Example 1 are shown in FIG. 11. Single-stranded DNA size markers for electrophoresis, manufactured by GeneDesign Inc., were used as size markers of the single-stranded DNA. This contains single-stranded DNA having a number of nucleotides of 15, 20, 30, 40, 50, 60 and 80. Double-stranded RNA size markers for electrophoresis, manufactured by GeneDesign Inc., were used as size markers of the double-stranded RNA. This contains double-stranded RNA having a number of base pairs of 17, 21, 25 and 29. Incidentally, in FIG. 11, "Lane No." indicates lane numbers in the above-mentioned electrophoresis test, "Example No." indicates the number of Examples, "before" indicates the results prior to the above-mentioned hybridization treatment, "after" indicates the results after the above-mentioned hybridization treatment, "ss-DNA size marker" indicates size markers of the single-stranded DNA, "ds-RNA size marker" indicates size markers of the double-stranded RNA, "mer" indicates the number of bases, and "bp" indicates the number of base pairs.

As is clear from FIG. 11, it was confirmed that the single-stranded oligonucleotide according to the present invention adopts the structure of intramolecular hybridization without passing through a special hybridization step or by simple heating and cooling operations.

Example 2, Comparative Example 2

The oligonucleotides described in Table 2 were prepared using Automated Nucleic Acid Synthesizer nS-8II (manufactured by GeneDesign). The target gene is human Phosphatase and Tensin Homolog Deleted from Chromosome 10 (PTEN). Incidentally, in the sequence notations shown in Table 2, "(m)" indicates 2'-O-methoxyethyl nucleotide, "5" indicates that the base of the nucleotide is 5-methylcytosine, "5(x)" indicates that the base of the deoxyribonucleotide is 5-methylcytosine, and the other sequence indications are the same as those of Table 1.

TABLE 2

| | Sequence (left side represents 5'-side and right side represents 3'-side) | Remarks |
|---|---|---|
| Example 2 (SEQ ID NO: 4) | U(M)^C(M)^A(M)^A(M)^A(M)^UCCAGAGGCUA 5(m)^T(m)^G(M)^5(m)^T(m)^a^g^5(x)^5(x)^ t^5(x)^t^g^g^a^T(m)^T(m)^T(m)^G(m)^A(m) | Bases 1-16: Y Bases 17-36: X (Bases 17-20: Xa, Bases 21-36: Xb) |
| Comparative Example 2 (SEQ ID NO: 5) | 5(m)^T(m)^G(m)^5(m)^T(m)^a^g^5(x)^5 (x)^t^5(x)^t^g^g^a^T(m)^T(m)^T(m)^G(m)^ A(m) | |
| Comparative Example 3 (SEQ ID NO: 6) | U(M)^C(M)^A(M)^A(M)^A(M)^UCCAGAGGCUAGCA GAAAA5(m)^T(m)^G(m)^5(m)^T(m)^a^g^5(x)^ 5(x)^t^5(x)^t^g^g^a^T(m)^T(m)^T(m)^G(m)^ A(m) | |

Intramolecular hybridization in Example 2 and Comparative Example 3 were carried out by heating for 5 minutes at 95° C. followed by allowing to stand for 1 hour at 37° C. with a constant temperature. Hybridization was confirmed by nondenaturing polyacrylamide gel electrophoresis.

Evaluation Example 3

Cells of human hepatoma-derived cell line HuH-7 were seeded on a 96-well plate so as to be 3,000 cells/well, and cultured at 37° C. under 5% $CO_2$ for 24 hours. Each oligonucleotide in Table 2 was added to each well using Lipofectamine® RNAiMax (manufactured by Thermo Fisher Scientific) such that the final concentration was to be 1 nM (transfection). After 4 hours, the medium was changed, and after an additional 20 hours, cells were collected, and total RNA was extracted from the cells using RNeasy mini kit (manufactured by QIAGEN).

cDNA was obtained from the total RNA using PrimeScript RT Master Mix (manufactured by Takara Bio Inc.). Using the obtained cDNA and TaqMan® Gene Expression ID (manufactured by Applied Biosystems), real-time PCR was performed by 7500 Real-Time PCR System (manufactured by Applied Biosystems) to determine the amount of mRNA of PTEN. In the real-time PCR, the amount of mRNA of a housekeeping gene GAPDH (Glyceraldehyde-3-Phosphate Dehydrogenase) was also determined simultaneously, and the amount of mRNA of PTEN relative to the amount of mRNA of GAPDH was evaluated as the expression level of PTEN, respectively. Cells not subjected to the transfection procedure were used as a control. The results are shown in FIG. 12.

Incidentally, primers used are TaqMan Gene Expression Assay (manufactured by Applied Biosystems), and the Assay ID was as follows:

Human PTEN assay: Hs02621230
Human GAPDH assay: Hs99999905_m1

Figure 12:
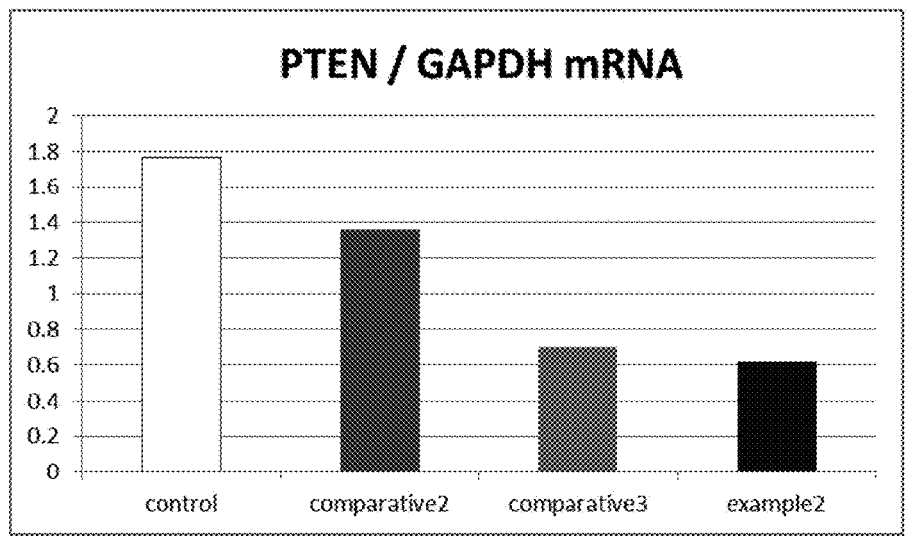
FIG. 12 is a graph indicating the effects of single-stranded oligonucleotides according to the present embodiment on the expression level of PTEN in human hepatoma-derived cells.

As is clear from FIG. 12, the single-stranded oligonucleotide (Example 2) according to the present invention was confirmed to demonstrate a higher antisense effect in comparison with ASO (Comparative Example 2). In addition, the single-stranded oligonucleotide (Example 2) according to the present invention was confirmed to demonstrate an antisense effect equal to or more than that of HDO (Comparative Example 3) which was coupled with the oligonucleotide.

Evaluation Example 4

Figure 13:
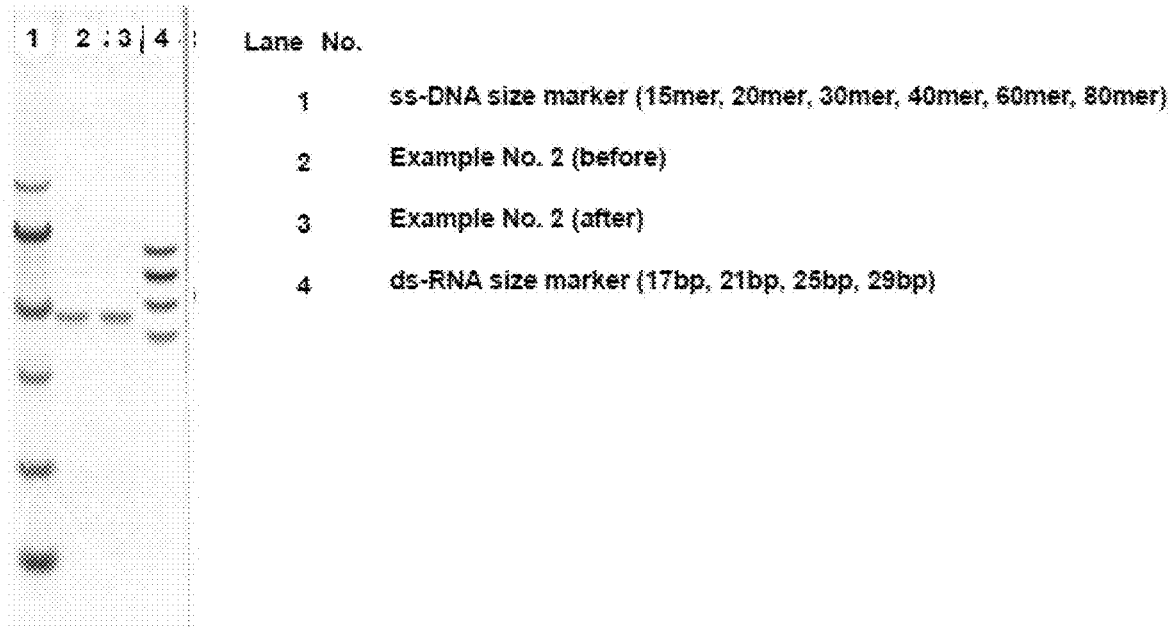
FIG. 13 indicates the results of gel electrophoresis of single-stranded oligonucleotides according to the present embodiment before and after hybridization treatment.

The results of nondenaturing polyacrylamide gel electrophoresis before and after the above-mentioned intramolecular hybridization treatment in Example 2 are shown in FIG. 13. Single-stranded DNA size markers for electrophoresis, manufactured by GeneDesign Inc., were used as size markers of the single-stranded DNA. Double-stranded RNA size markers for electrophoresis, manufactured by GeneDesign Inc., were used as size markers of the double-stranded RNA. Incidentally, abbreviations in FIG. 13 are the same as those in FIG. 11.

As is clear from FIG. 13, it was confirmed that the single-stranded oligonucleotide according to the present invention adopts the structure of intramolecular hybridization without passing through a special hybridization step or by simple heating and cooling operations.

Example 3, Comparative Examples 4 and 5

The oligonucleotides described in Table 3 were prepared using Automated Nucleic Acid Synthesizer nS-8II (manufactured by GeneDesign). The target gene is mouse scavenger receptor class B member 1 (SRB1). Incidentally, in the sequence notations in Table 3, "(V)" indicates 2'-O-methylcarbamoylethyl nucleotide, and the other sequence notations are the same as those in Table 1 and Table 2.

TABLE 3

| | Sequence (left side represents 5'-side and right side represents 3'-side) | Remarks |
|---|---|---|
| Example 3 (SEQ ID NO: 7) | Toc-TEG-AAGGAAGUCAUGACUGG (V)^5(V)^T(V)^T(V)^5(V)^a^g^t^c^ a^t^g^a^c^t^T(V)^5(V)^5(V)^T(V)^T(V) | Bases 1-16: Y Bases 17-36: X (Bases 17-20: Xa, Bases 21-36: Xb) |
| Comparative Example 4 (SEQ ID NO: 8) | G(V)^5(V)^T(V)^T(V)^5(V)^a^g^t^c^a^ t^g^a^c^t^T(V)^5(V)^5(V)^T(V)^T(V) | |
| Comparative Example 5 (SEQ ID NO: 9) | Toc-TEG-AAGGAAGUCAUGACUGAAGCAAAAG(V)^ 5(V)^T(V)^T(V)^5(V)^a^g^t^c^a^t^g^a^c^ t^T(V)^5(V)^5(V)^T(V)^T(V) | Functional molecule is bound |

Intramolecular hybridization in Example 3 and Comparative Example 5 were carried out by heating for 5 minutes at 95° C. followed by allowing to stand for 1 hour at 37° C. with a constant temperature. Hybridization was confirmed by nondenaturing polyacrylamide gel electrophoresis.

Evaluation Example 5

The same evaluation method as in Evaluation Example 1 was used. Each oligonucleotide of Example 3 and Comparative Example 5 in Table 3 was intravenously administered so that the dosage was 0.7 µmol/kg per mouse individual body in terms of the amount of the antisense oligonucleotides, and the oligonucleotide of Comparative Example 4 so that the dosage was 1.4 µmol/kg per mouse individual body in terms of the amount of the antisense oligonucleotides. Administration of physiological saline only (Otsuka Normal Saline, Otsuka Pharmaceutical Factory) was used as a control. The amount of mRNA of SRB1 relative to the amount of mRNA of Cyclophilin at liver tissue three days after the administration was evaluated as the expression level of SRB1. The results are shown in FIG. 14.

Figure 14:
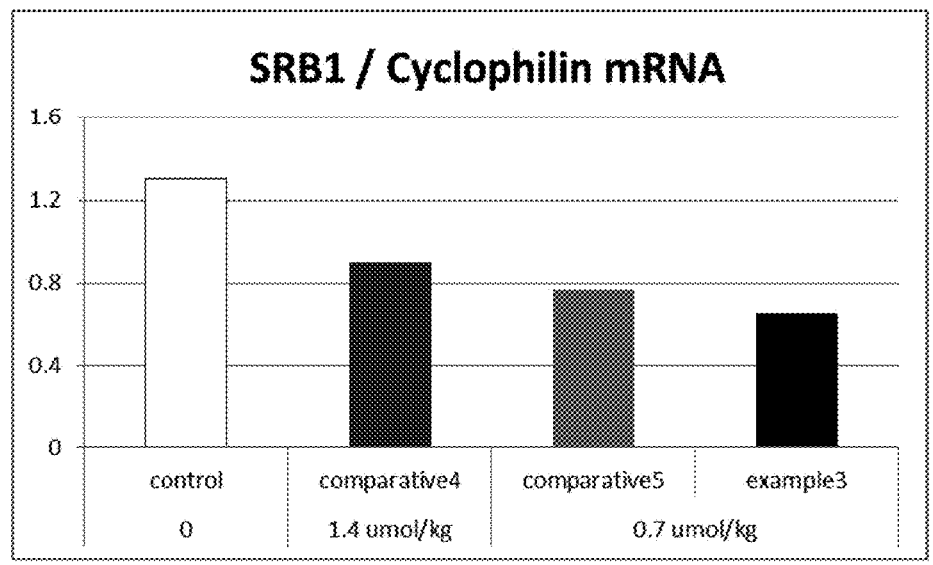
FIG. 14 is a graph indicating the effects on the expression level of SRB1 in the liver of C57BL/6J mice administered a single-stranded oligonucleotide according to the present embodiment.

As is clear from FIG. 14, the single-stranded oligonucleotide (Example 3) according to the present invention were confirmed to demonstrate a higher antisense effect in comparison with ASO (Comparative Example 4). In addition, the single-stranded oligonucleotide (Example 3) according to the present invention were confirmed to demonstrate an antisense effect equal to or more than that of HDO (Comparative Example 5) which was coupled with the oligonucleotide.

Evaluation Example 6

Figure 15:
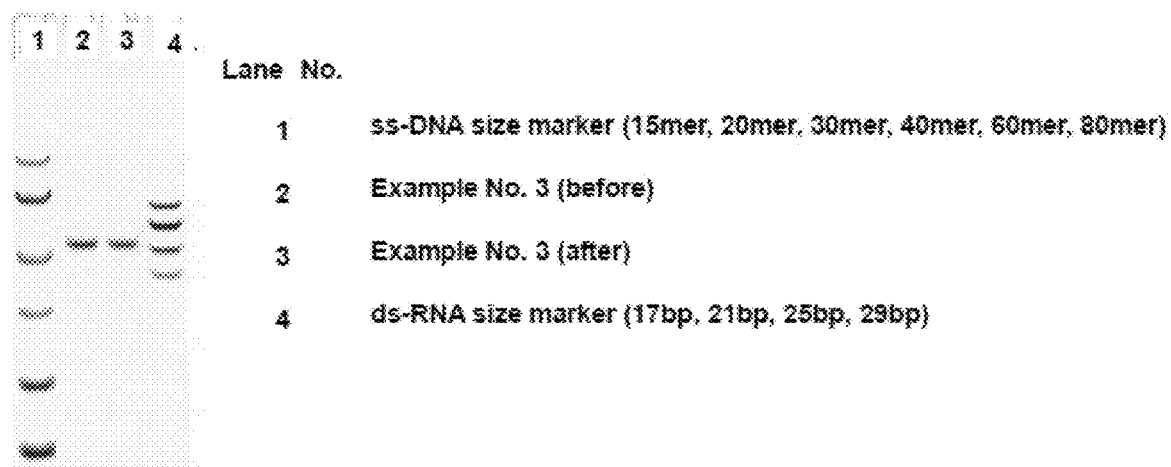
FIG. 15 indicates the results of gel electrophoresis of single-stranded nucleotides according to the present embodiment before and after hybridization treatment.

The results of nondenaturing polyacrylamide gel electrophoresis before and after the above-mentioned intramolecular hybridization treatment in Example 3 are shown in FIG. 15. Single-stranded DNA size markers for electrophoresis, manufactured by GeneDesign Inc., were used as size markers of the single-stranded DNA. Double-stranded RNA size markers for electrophoresis, manufactured by GeneDesign Inc., were used as size markers of the double-stranded RNA. Incidentally, abbreviations in FIG. 15 are the same as those in FIG. 11.

As is clear from FIG. 15, it was confirmed that the single-stranded oligonucleotide according to the present invention adopts the structure of intramolecular hybridization without passing through a special hybridization step or by simple heating and cooling operations.

INDUSTRIAL APPLICABILITY

Use of the single-stranded oligonucleotide of the present invention makes it possible to efficiently deliver an antisense nucleic acid to a specific organ (or cell) with high specificity, effectively control the function of a target RNA with that nucleic acid, and/or effectively suppress expression of a target gene. In addition, since the single-stranded oligonucleotide of the present invention is able to apply various molecules such as lipids (such as tocopherol and cholesterol), sugars (such as glucose and sucrose), protein, peptides or antibodies as functional molecules for delivering to a specific organ, the single-stranded oligonucleotide of the present invention is able to target various organs, tissues and cells. Moreover, since the antisense effect thereof does not decrease even if the single-stranded oligonucleotide of the present invention is modified in order to impart resistance to RNase and the like, it can also be used in an aspect of enteral administration.

Thus, the single-stranded oligonucleotide of the present invention allows the obtaining of high pharmacological efficacy by administering at a low concentration, and since it is also superior in terms of reducing adverse side effects as a result of suppressing distribution in organs other than the target of the antisense nucleic acid, it is useful as a pharmaceutical composition and the like for treating and preventing diseases associated with function of a target RNA and/or overexpression of a target gene, such as metabolic diseases, tumors or infections.

SEQUENCE LISTING

FP4314PCT_ST25.txt

The invention claimed is:

1. A single-stranded oligonucleotide represented by the following formula (I):

$$[Xz\text{-}Lx]_m\text{-}X\text{-}Y\text{-}[Ly\text{-}Yz]_n \quad (I)$$

wherein,

Y represents a group derived from an oligonucleotide Y composed of 4 to 40 nucleotides containing at least one ribonucleotide that are independently selected from the group consisting of deoxyribonucleotides, ribonucleotides and sugar-modified nucleotides, X represents a group derived from an oligonucleotide X composed of 5 to 80 nucleotides represented by the formula:

Xb-Xa wherein,

Xb represents a group derived from an oligonucleotide Xb composed of 4 to 40 nucleotides containing at least one sugar-modified nucleotides that are independently selected from the group consisting of deoxyribonucleotides, ribonucleotides and sugar-modified nucleotides, Xa represents a group derived from an oligonucleotide Xa composed of 1 to 40 nucleotides containing at least one sugar-modified nucleotides that are independently selected from the group consisting of deoxyribonucleotides, ribonucleotides and sugar-modified nucleotides, and Xa is bonded with the oligonucleotide Y and the oligonucleotide Xb at both ends respectively, Xz represents a group derived from an oligonucleotide Xz composed of 5 to 40 nucleotides containing at least one sugar-modified nucleotides that are independently selected from the group consisting of deoxyribonucleotides, ribonucleotides and sugar-modified nucleotides, Yz represents a group derived from an oligonucleotide Yz composed of 5 to 40 nucleotides containing at least one sugar-modified nucleotides that are independently selected from the group consisting of deoxyribonucleotides, ribonucleotides and sugar-modified nucleotides, Lx represents a group derived from an oligonucleotide Lx composed of 0 to 20 nucleotides that are independently selected from the group consisting of deoxyribonucleotides, ribonucleotides and sugar-modified nucleotides, and is bonded with the Xb, Ly represents a group derived from an oligonucleotide Ly composed of 0 to 20 nucleotides that are independently selected from the group consisting of deoxyribonucleotides, ribonucleotides and sugar-modified nucleotides, m represents 0 or 1, when m represents 0, n represents 0 or 1, when m represents 1, n represents 0, the oligonucleotide X has a nucleotide sequence X, the oligonucleotide Xa has a nucleotide sequence Xa, the oligonucleotide Xb has a nucleotide sequence Xb, the oligonucleotide Y has a nucleotide sequence Y, the oligonucleotide Xz has a nucleotide sequence Xz, the oligonucleotide Yz has a nucleotide sequence Yz, the oligonucleotide Lx has a nucleotide sequence Lx, and the oligonucleotide Ly has a nucleotide sequence Ly, the nucleotide sequence Xb is complementary to the nucleotide sequence Y, the nucleotide sequence X contains an antisense sequence that is capable of hybridizing with a target RNA, when m represents 1 and n represents 0, the nucleotide sequence Xz contains an antisense sequence that is capable of hybridizing with a target RNA, when m represents 0 and n represents 1, the nucleotide sequence Yz contains an antisense sequence that is capable of hybridizing with a target RNA, and in the case of having two or more of the antisense sequences, the target RNA hybridized by each antisense sequence portion may each be the same or different, and Xb and Y hybridize.

2. The single-stranded oligonucleotide according to claim 1, wherein Xb bonds to Xa on the 3'-side and Y bonds to Xa on the 5'-side.

3. The single-stranded oligonucleotide according to claim 1, wherein Xb bonds to Xa on the 5'-side and Y bonds to Xa on the 3'-side.

4. The single-stranded oligonucleotide according to claim 1, wherein the antisense sequence is a sequence each independently containing at least four contiguous nucleotides recognized by RNase H, or a sequence containing at least one sugar-modified nucleotide, and not containing four contiguous deoxyribonucleotides.

5. The single-stranded oligonucleotide according to claim 4, wherein at least one of the antisense sequence is a sequence containing at least four contiguous nucleotides recognized by RNase H, and the antisense sequence portion contains a sugar-modified nucleotide bound adjacent to the 5'-side and the 3'-side of the sequence portion containing the above-mentioned at least four contiguous nucleotides recognized by RNase H.

6. The single-stranded oligonucleotide according to claim 1, wherein the antisense sequence portion contains a phosphorothioate bond.

7. The single-stranded oligonucleotide according to claim 1, wherein the antisense sequence is a sequence composed of 10 to 30 nucleotides containing at least one deoxyribonucleotide.

8. The single-stranded oligonucleotide according to claim 1, wherein the nucleotide sequence Y is a sequence containing at least four contiguous nucleotides cleaved by RNase H.

9. The single-stranded oligonucleotide according to claim 1, wherein the oligonucleotide Y contains one or a plurality of sugar-modified nucleotides on at least one of the 5'-side and the 3'-side of the oligonucleotide Y.

10. The single-stranded oligonucleotide according to claim 1, wherein m is 0 and n is 0.

11. The single-stranded oligonucleotide according to claim 1, wherein m is 0 and n is 1.

12. The single-stranded oligonucleotide according to claim 11, wherein the nucleotides contained in the oligonucleotide Ly are mutually coupled through a phosphodiester bond.

13. The single-stranded oligonucleotide according to claim 11, wherein the oligonucleotide Ly is DNA or RNA.

14. The single-stranded oligonucleotide according to claim 1, wherein m is 1 and n is 0.

15. The single-stranded oligonucleotide according to claim 14, wherein the nucleotides contained in the oligonucleotide Lx are mutually coupled through a phosphodiester bond.

16. The single-stranded oligonucleotide according to claim 14, wherein the oligonucleotide Lx is DNA or RNA.

17. The single-stranded oligonucleotide according to claim 1, which further contains a group derived from a functional molecule having at least one function selected from the group consisting of a labeling function, a purifying function and a target site delivery function.

18. The single-stranded oligonucleotide according to claim 17, wherein the functional molecule is selected from the group consisting of sugars, lipids, peptides, proteins and derivatives thereof.

19. The single-stranded oligonucleotide according to claim 17, wherein the functional molecule is a lipid selected from the group consisting of cholesterol, tocopherol and tocotrienol.

20. The single-stranded oligonucleotide according to claim 17, wherein the functional molecule is a sugar derivative that interacts with an asialoglycoprotein receptor.

21. The single-stranded oligonucleotide according to claim 17, wherein the functional molecule is a peptide or protein selected from the group consisting of receptor ligands and antibodies.

22. A pharmaceutical composition containing the single-stranded oligonucleotide according to claim 1 and a pharmacologically acceptable carrier.

23. A method for controlling a function of a target RNA which hybridizes with a single-stranded oligonucleotide according to claim 1, including a step for contacting the single-stranded oligonucleotide with a cell, wherein a portion of the target RNA hybridizes with an antisense sequence portion of the single-stranded oligonucleotide as a result of the contacting.

24. A method for controlling a function of a target RNA which hybridizes with a single-stranded oligonucleotide according to claim 1 in a mammal, including a step for administering a pharmaceutical composition containing the single-stranded oligonucleotide to the mammal, wherein a portion of the target RNA hybridizes with an antisense sequence portion of the single-stranded oligonucleotide as a result of the administering.

25. A method for controlling expression of a target gene corresponding to a target RNA which hybridizes with a single-stranded oligonucleotide according to claim 1, including a step for contacting the single-stranded oligonucleotide with a cell, wherein a portion of the target RNA hybridizes with an antisense sequence portion of the single-stranded oligonucleotide as a result of the contacting.

26. A method for controlling expression of a target gene corresponding to a target RNA which hybridizes with a single-stranded oligonucleotide according to claim 1 in a mammal, including a step for administering a pharmaceutical composition containing the single-stranded oligonucleotide to the mammal, wherein a portion of the target RNA hybridizes with an antisense sequence portion of the single-stranded oligonucleotide as a result of the administering.

27. A method for producing the single-stranded oligonucleotide according to claim 1, including a step for elongating the nucleotide strand at the 3'-end or 5'-end of an oligonucleotide containing at least one of X and Y.

28. The single-stranded oligonucleotide according to claim 1, wherein the sugar-modified nucleotide is at least one selected from the group consisting of hexitol nucleotides, cyclohexene nucleotides, peptide nucleic acids, glycol nucleic acids, threose nucleotides, morpholine nucleic acids, tricyclo-DNA, 2'-O-methyl nucleotides, 2'-O-methoxyethyl nucleotides, 2'-O-aminopropyl nucleotide, 2'-fluoronucleotide, 2'-F-arabinonucleotides, bridged nucleotides, and 2'-O-methylcarbamoylethyl nucleotides.

* * * * *

SEQUENCE LISTING

```
<160> NUMBER OF SEQ ID NOS: 9

<210> SEQ ID NO 1
<211> LENGTH: 24
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (1)..(1)
<223> OTHER INFORMATION: modified with tocopheryl group via
      (hydroxymethyl)tetraethylene glycol
<220> FEATURE:
<221> NAME/KEY: modified_base
<222> LOCATION: (1)..(3)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(10)
<223> OTHER INFORMATION: ribonucleoside
<220> FEATURE:
<221> NAME/KEY: modified_base
<222> LOCATION: (11)..(12)
<223> OTHER INFORMATION: LNA
<220> FEATURE:
<221> NAME/KEY: modified_base
<222> LOCATION: (11)..(24)
<223> OTHER INFORMATION: phosphorothioate bond between nucleic acids
<220> FEATURE:
<221> NAME/KEY: modified_base
<222> LOCATION: (12)..(12)
<223> OTHER INFORMATION: m5c
<220> FEATURE:
<221> NAME/KEY: modified_base
<222> LOCATION: (23)..(24)
<223> OTHER INFORMATION: LNA
<220> FEATURE:
<221> NAME/KEY: modified_base
<222> LOCATION: (24)..(24)
```

<223> OTHER INFORMATION: m5c

<400> SEQUENCE: 1
gaagucauga tcagtcatga cttc                                              24

<210> SEQ ID NO 2
<211> LENGTH: 14
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(14)
<223> OTHER INFORMATION: phosphorothioate bond between nucleic acids
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (2)..(2)
<223> OTHER INFORMATION: m5c
<220> FEATURE:
<221> NAME/KEY: modified_base
<222> LOCATION: (13)..(14)
<223> OTHER INFORMATION: LNA
<220> FEATURE:
<221> NAME/KEY: modified_base
<222> LOCATION: (14)..(14)
<223> OTHER INFORMATION: m5c

<400> SEQUENCE: 2
tcagtcatga cttc                                                         14

<210> SEQ ID NO 3
<211> LENGTH: 14
<212> TYPE: RNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (1)..(1)
<223> OTHER INFORMATION: modified with tocopheryl group via
      (hydroxymethyl)tetraethylene glycol
<220> FEATURE:
<221> NAME/KEY: modified_base
<222> LOCATION: (1)..(3)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (12)..(14)
<223> OTHER INFORMATION: phosphorothioate bond between nucleic acids
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: 2'-O-methyladenosine

<400> SEQUENCE: 3
gaagucauga cuga                                                         14

```
<210> SEQ ID NO 4
<211> LENGTH: 36
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (1)..(6)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(5)
<223> OTHER INFORMATION: 2'-O-methyladenosine
<220> FEATURE:
<221> NAME/KEY: modified_base
<222> LOCATION: (6)..(16)
<223> OTHER INFORMATION: ribonucleoside
<220> FEATURE:
<221> NAME/KEY: modified_base
<222> LOCATION: (17)..(17)
<223> OTHER INFORMATION: m5c
<220> FEATURE:
<221> NAME/KEY: modified_base
<222> LOCATION: (17)..(21)
<223> OTHER INFORMATION: modified with methoxyethyl at 2'-OH
<220> FEATURE:
<221> NAME/KEY: modified_base
<222> LOCATION: (17)..(36)
<223> OTHER INFORMATION: phosphorothioate bond between nucleic acids
<220> FEATURE:
<221> NAME/KEY: modified_base
<222> LOCATION: (20)..(20)
<223> OTHER INFORMATION: m5c
<220> FEATURE:
<221> NAME/KEY: modified_base
<222> LOCATION: (24)..(25)
<223> OTHER INFORMATION: m5c
<220> FEATURE:
<221> NAME/KEY: modified_base
<222> LOCATION: (27)..(27)
<223> OTHER INFORMATION: m5c
<220> FEATURE:
<221> NAME/KEY: modified_base
<222> LOCATION: (32)..(36)
<223> OTHER INFORMATION: modified with methoxyethyl at 2'-OH

<400> SEQUENCE: 4
ucaaauccag aggcuactgc tagcctctgg atttga                            36

<210> SEQ ID NO 5
<211> LENGTH: 20
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(5)
<223> OTHER INFORMATION: modified with methoxyethyl at 2'-OH
<220> FEATURE:
<221> NAME/KEY: modified_base
<222> LOCATION: (1)..(20)
<223> OTHER INFORMATION: phosphorothioate bond between nucleic acids
```

-continued

```
<220> FEATURE:
<221> NAME/KEY: modified_base
<222> LOCATION: (4)..(4)
<223> OTHER INFORMATION: m5c
<220> FEATURE:
<221> NAME/KEY: modified_base
<222> LOCATION: (8)..(9)
<223> OTHER INFORMATION: m5c
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (16)..(20)
<223> OTHER INFORMATION: modified with methoxyethyl at 2'-OH

<400> SEQUENCE: 5
ctgctagcct ctggatttga                                            20

<210> SEQ ID NO 6
<211> LENGTH: 44
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (1)..(6)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(5)
<223> OTHER INFORMATION: 2'-O-methyladenosine
<220> FEATURE:
<221> NAME/KEY: modified_base
<222> LOCATION: (6)..(24)
<223> OTHER INFORMATION: ribonucleoside
<220> FEATURE:
<221> NAME/KEY: modified_base
<222> LOCATION: (25)..(25)
<223> OTHER INFORMATION: m5c
<220> FEATURE:
<221> NAME/KEY: modified_base
<222> LOCATION: (25)..(29)
<223> OTHER INFORMATION: modified with methoxyethyl at 2'-OH
<220> FEATURE:
<221> NAME/KEY: modified_base
<222> LOCATION: (25)..(44)
<223> OTHER INFORMATION: phosphorothioate bond between nucleic acids
<220> FEATURE:
<221> NAME/KEY: modified_base
<222> LOCATION: (28)..(28)
<223> OTHER INFORMATION: m5c
<220> FEATURE:
<221> NAME/KEY: modified_base
<222> LOCATION: (32)..(33)
<223> OTHER INFORMATION: m5c
<220> FEATURE:
<221> NAME/KEY: modified_base
<222> LOCATION: (35)..(35)
<223> OTHER INFORMATION: m5c
<220> FEATURE:
<221> NAME/KEY: modified_base
<222> LOCATION: (40)..(44)
<223> OTHER INFORMATION: modified with methoxyethyl at 2'-OH
```

<400> SEQUENCE: 6
ucaaauccag aggcuagcag aaaactgcta gcctctggat ttga            44

<210> SEQ ID NO 7
<211> LENGTH: 36
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: modified with tocopheryl group via
      (hydroxymethyl)tetraethylene glycol
<220> FEATURE:
<221> NAME/KEY: modified_base
<222> LOCATION: (1)..(16)
<223> OTHER INFORMATION: ribonucleoside
<220> FEATURE:
<221> NAME/KEY: modified_base
<222> LOCATION: (17)..(21)
<223> OTHER INFORMATION: modified with methylcarbamoylethyl at 2'-OH
<220> FEATURE:
<221> NAME/KEY: modified_base
<222> LOCATION: (17)..(36)
<223> OTHER INFORMATION: phosphorothioate bond between nucleic acids
<220> FEATURE:
<221> NAME/KEY: modified_base
<222> LOCATION: (18)..(18)
<223> OTHER INFORMATION: m5c
<220> FEATURE:
<221> NAME/KEY: modified_base
<222> LOCATION: (21)..(21)
<223> OTHER INFORMATION: m5c
<220> FEATURE:
<221> NAME/KEY: modified_base
<222> LOCATION: (32)..(36)
<223> OTHER INFORMATION: modified with methylcarbamoylethyl at 2'-OH
<220> FEATURE:
<221> NAME/KEY: modified_base
<222> LOCATION: (33)..(34)
<223> OTHER INFORMATION: m5c

<400> SEQUENCE: 7
aaggaaguca ugacuggctt cagtcatgac ttcctt            36

<210> SEQ ID NO 8
<211> LENGTH: 20
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(5)
<223> OTHER INFORMATION: modified with methylcarbamoylethyl at 2'-OH
<220> FEATURE:
<221> NAME/KEY: modified_base
<222> LOCATION: (1)..(20)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: m5c
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (16)..(20)
<223> OTHER INFORMATION: modified with methylcarbamoylethyl at 2'-OH
<220> FEATURE:
<221> NAME/KEY: modified_base

```
<222> LOCATION: (17)..(18)
<223> OTHER INFORMATION: m5c

<400> SEQUENCE: 8
gcttcagtca tgacttcctt                                               20

<210> SEQ ID NO 9
<211> LENGTH: 44
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: modified with tocopheryl group via
      (hydroxymethyl)tetraethylene glycol
<220> FEATURE:
<221> NAME/KEY: modified_base
<222> LOCATION: (1)..(24)
<223> OTHER INFORMATION: ribonucleoside
<220> FEATURE:
<221> NAME/KEY: modified_base
<222> LOCATION: (25)..(29)
<223> OTHER INFORMATION: modified with methylcarbamoylethyl at 2'-OH
<220> FEATURE:
<221> NAME/KEY: modified_base
<222> LOCATION: (25)..(44)
<223> OTHER INFORMATION: phosphorothioate bond between nucleic acids
<220> FEATURE:
<221> NAME/KEY: modified_base
<222> LOCATION: (26)..(26)
<223> OTHER INFORMATION: m5c
<220> FEATURE:
<221> NAME/KEY: modified_base
<222> LOCATION: (29)..(29)
<223> OTHER INFORMATION: m5c
<220> FEATURE:
<221> NAME/KEY: modified_base
<222> LOCATION: (40)..(44)
<223> OTHER INFORMATION: modified with methylcarbamoylethyl at 2'-OH
<220> FEATURE:
<221> NAME/KEY: modified_base
<222> LOCATION: (41)..(42)
<223> OTHER INFORMATION: m5c

<400> SEQUENCE: 9
aaggaaguca ugacugaagc aaaagcuuca gtcatgactt cctt                    44
```